US008354381B2

(12) United States Patent
Fahnestock et al.

(10) Patent No.: US 8,354,381 B2
(45) Date of Patent: Jan. 15, 2013

(54) PEPTIDE COMPOSITIONS FOR ORAL CARE SYSTEMS

(75) Inventors: Stephen R. Fahnestock, Wilmington, DE (US); Kari A. Fosser, Wilmington, DE (US); Hong Wang, Kennett Square, PA (US); Pierre E. Rouviere, Wilmington, DE (US); Tanja Maria Gruber, Media, PA (US); Douglas Robert Anton, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 119 days.

(21) Appl. No.: 12/732,248

(22) Filed: Mar. 26, 2010

(65) Prior Publication Data

US 2010/0247589 A1 Sep. 30, 2010

Related U.S. Application Data

(60) Provisional application No. 61/164,476, filed on Mar. 30, 2009.

(51) Int. Cl.
*A61K 38/08* (2006.01)
*A61C 17/00* (2006.01)
*A61C 15/00* (2006.01)

(52) U.S. Cl. ............... 514/21.6; 433/37; 433/217.1
(58) Field of Classification Search ............... None
See application file for complete search history.

(56) References Cited

U.S. PATENT DOCUMENTS

| | | | |
|---|---|---|---|
| 3,961,975 A | 6/1976 | Zannucci et al. | |
| 4,494,994 A | 1/1985 | Cioca et al. | |
| 5,085,698 A | 2/1992 | Ma et al. | |
| 5,124,438 A | 6/1992 | Brueckmann et al. | |
| 5,231,131 A | 7/1993 | Chu et al. | |
| 5,451,390 A | 9/1995 | Hartmann et al. | |
| 5,490,988 A | 2/1996 | Beggs et al. | |
| 5,519,085 A | 5/1996 | Ma et al. | |
| 5,672,330 A | 9/1997 | Hartmann et al. | |
| 5,762,914 A | 6/1998 | Hartmann et al. | |
| 5,801,226 A | 9/1998 | Cummins et al. | |
| 5,962,641 A | 10/1999 | Nelson et al. | |
| 6,264,925 B1 | 7/2001 | Fuglsang et al. | |
| 6,706,256 B2 | 3/2004 | Lawlor | |
| 6,740,311 B2 | 5/2004 | White et al. | |
| 7,220,405 B2 | 5/2007 | Huang et al. | |
| 7,285,264 B2 | 10/2007 | O'Brien et al. | |
| 7,309,482 B2 | 12/2007 | Buse-Williams et al. | |
| 7,341,604 B2 | 3/2008 | Rothe et al. | |
| 7,807,141 B2 * | 10/2010 | Huang et al. ............... | 424/49 |
| 2002/0098524 A1 | 7/2002 | Murray et al. | |
| 2003/0152976 A1 | 8/2003 | Janssen et al. | |
| 2003/0185870 A1 | 10/2003 | Grinstaff et al. | |
| 2004/0232377 A1 | 11/2004 | Nigam | |
| 2005/0054752 A1 | 3/2005 | O'Brien et al. | |
| 2005/0069501 A1 | 3/2005 | Ibrahim et al. | |
| 2005/0107256 A1 | 5/2005 | Barnwell et al. | |
| 2005/0226839 A1 | 10/2005 | Huang et al. | |
| 2006/0073111 A1 | 4/2006 | O'Brien et al. | |
| 2006/0140889 A1 | 6/2006 | Houtzager et al. | |
| 2006/0199206 A1 | 9/2006 | Wang et al. | |
| 2006/0222609 A1 | 10/2006 | O'Brien et al. | |
| 2007/0065387 A1 | 3/2007 | Beck et al. | |
| 2007/0110686 A1 | 5/2007 | Lowe et al. | |
| 2007/0141628 A1 | 6/2007 | Cunningham et al. | |
| 2007/0141629 A1 | 6/2007 | Cunningham et al. | |
| 2007/0196305 A1 | 8/2007 | Wang et al. | |
| 2007/0261775 A1 | 11/2007 | Cunningham et al. | |
| 2007/0264720 A1 | 11/2007 | Cunningham et al. | |
| 2007/0265431 A1 | 11/2007 | Cunningham et al. | |
| 2008/0107614 A1 | 5/2008 | Fahnestock et al. | |
| 2008/0152600 A1 | 6/2008 | Huang et al. | |
| 2008/0175798 A1 | 7/2008 | Beck et al. | |
| 2008/0207872 A1 | 8/2008 | Cunningham et al. | |
| 2008/0279908 A1 | 11/2008 | Bertozzi et al. | |
| 2008/0280810 A1 * | 11/2008 | O'Brien et al. ............... | 514/2 |
| 2009/0029902 A1 | 1/2009 | Cunningham et al. | |
| 2009/0043075 A1 | 2/2009 | Alsop et al. | |
| 2009/0070944 A1 | 3/2009 | Benson et al. | |
| 2009/0136433 A1 | 5/2009 | Subkowski et al. | |
| 2010/0158822 A1 | 6/2010 | Fahnestock et al. | |
| 2010/0158823 A1 | 6/2010 | Cheng et al. | |

FOREIGN PATENT DOCUMENTS

| | | |
|---|---|---|
| EP | 0453097 A2 | 10/1991 |
| EP | 0736544 B1 | 10/1996 |
| JP | 02311412 A | 12/1990 |
| JP | 02616786 B2 | 6/1997 |
| JP | 2002363026 A | 12/2002 |
| WO | 0107009 A1 | 2/2001 |
| WO | 2004048399 A2 | 6/2004 |
| WO | 2006068011 A1 | 6/2006 |
| WO | 2007038683 A2 | 4/2007 |
| WO | WO-2007/038683 * | 4/2007 |

OTHER PUBLICATIONS

Bihari, Peter et al. (2008) Particle and Fibre Toxicology 5, 1-14.
Notice of Transmittal of the International Search Report and Written Opinion of the International Searching Authority, Published Oct. 14, 2010, International Application No. PCT/US 10/29139.
Birren et al. Predicted Protein [*Coprinosis cinerea* Okayama7#130] Genbank Accession No. XP_001839209 Version (XP_001839209.1 GI:169865211) Apr. 3, 2008.
Binz, H. Kaspar et al. (2005) Nature Biotechnology 23, 1257-1268.
Adey, Nils B. (1995) Gene 156, 27-31.
U.S. Appl. No. 61/164,476, filed Mar. 30, 2009 to Fahnestock et al.
U.S. Appl. No. 12/698,172, filed Feb. 2, 2010 to Anton et al.
Bio Conference, San Francisco, CA, Meeting Presentation by Genencor International, Jun. 8, 2004.
Muyldermans, Serge. (Jun. 25, 2001) Reviews in Molecular Biotechnology, 74, 277-302.
Invitation to Pay Additional Fees, Form PCT/ISA/206 (Apr. 2005), from the PCT International Search Authority, USA (ISA/US), Mailed Aug. 4, 2010, for International Application No. PCT/US 10/29139.

* cited by examiner

*Primary Examiner* — Karlheinz R Skowronek
*Assistant Examiner* — Satyanarayana R Gudibande

(57) ABSTRACT

Oral care compositions, oral care systems, oral surface-binding peptides, and a method for applying particles to an oral surface are provided. The oral care system comprises at least one peptidic component comprising a first binding element having affinity for an oral surface and a second binding element having affinity for a ligand property of a particle.

21 Claims, No Drawings

SEQUENCE LISTING

<160> NUMBER OF SEQ ID NOS: 168

<210> SEQ ID NO 1
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 1

Ala His Pro Glu Ser Leu Gly Ile Lys Tyr Ala Leu Asp Gly Asn Ser
1               5                   10                  15

Asp Pro His Ala
            20

<210> SEQ ID NO 2
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 2

Ala Ser Val Ser Asn Tyr Pro Pro Ile His His Leu Ala Thr Ser Asn
1               5                   10                  15

Thr Thr Val Asn
            20

<210> SEQ ID NO 3
<211> LENGTH: 14
<212> TYPE: PRT
<213> ORGANISM: Artificial Sequence
<220> FEATURE:
<223> OTHER INFORMATION: Synthetic oral-surface binding peptide

<400> SEQUENCE: 3

Asp Glu Cys Met Glu Pro Leu Asn Ala Ala His Cys Trp Arg
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic oral-surface binding peptide

<400> SEQUENCE: 4

Asp Glu Cys Met His Gly Ser Asp Val Glu Phe Cys Thr Ser
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetic oral-surface binding peptide

<400> SEQUENCE: 5

Asp Leu Cys Ser Met Gln Met Met Asn Thr Gly Cys His Tyr
1               5                   10

<210> SEQ ID NO 6
<211> LENGTH: 14
<212> TYPE: PRT
<213> ORGANISM: Artificial Sequence

```
<220> FEATURE:
<223> OTHER INFORMATION: Synthetic oral-surface binding peptide

<400> SEQUENCE: 6

Asp Leu Cys Ser Ser Pro Ser Thr Trp Gly Ser Cys Ile Arg
1               5                   10

<210> SEQ ID NO 7
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 7

Asp Pro Asn Glu Ser Asn Tyr Glu Asn Ala Thr Thr Val Ser Gln Pro
1               5                   10                  15

Thr Arg His Leu
            20

<210> SEQ ID NO 8
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 8

Glu Pro Thr His Pro Thr Met Arg Ala Gln Met His Gln Ser Leu Arg
1               5                   10                  15

Ser Ser Ser Pro
            20

<210> SEQ ID NO 9
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 9

Gly Asn Thr Asp Thr Thr Pro Pro Asn Ala Val Met Glu Pro Thr Val
1               5                   10                  15

Gln His Lys Trp
            20

<210> SEQ ID NO 10
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 10

Asn Gly Pro Asp Met Val Gln Ser Val Gly Lys His Lys Asn Ser
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 11

Asn Gly Pro Glu Val Arg Gln Ile Pro Ala Asn Phe Glu Lys Leu
```

```
<210> SEQ ID NO 12
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 12

Asn Asn Thr Ser Ala Asp Asn Pro Pro Glu Thr Asp Ser Lys His His
1               5                   10                  15

Leu Ser Met Ser
            20

<210> SEQ ID NO 13
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 13

Asn Asn Thr Trp Pro Glu Gly Ala Gly His Thr Met Pro Ser Thr Asn
1               5                   10                  15

Ile Arg Gln Ala
            20

<210> SEQ ID NO 14
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 14

Asn Pro Thr Ala Thr Pro His Met Lys Asp Pro Met His Ser Asn Ala
1               5                   10                  15

His Ser Ser Ala
            20

<210> SEQ ID NO 15
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 15

Asn Pro Thr Asp His Ile Pro Ala Asn Ser Thr Asn Ser Arg Val Ser
1               5                   10                  15

Lys Gly Asn Thr
            20

<210> SEQ ID NO 16
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 16

Asn Pro Thr Asp Ser Thr His Met Met His Ala Arg Asn His Glu
1               5                   10                  15
```

```
<210> SEQ ID NO 17
<211> LENGTH: 14
<212> TYPE: PRT
<213> ORGANISM: Artificial Sequence
<220> FEATURE:
<223> OTHER INFORMATION: Synthetic oral-surface binding peptide

<400> SEQUENCE: 17

Gln His Cys Ile Thr Glu Arg Leu His Pro Pro Cys Thr Lys
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Synthetic oral-surface binding peptide

<400> SEQUENCE: 18

Thr Pro Cys Ala Pro Ala Ser Phe Asn Pro His Cys Ser Arg
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Synthetic oral-surface binding peptide

<400> SEQUENCE: 19

Thr Pro Cys Ala Thr Tyr Pro His Phe Ser Gly Cys Arg Ala
1               5                   10

<210> SEQ ID NO 20
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 20

Trp Cys Thr Asp Phe Cys Thr Arg Ser Thr Pro Thr Ser Thr Ser Arg
1               5                   10                  15

Ser Thr Thr Ser
            20

<210> SEQ ID NO 21
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 21

Ala Pro Pro Leu Lys Thr Tyr Met Gln Glu Arg Glu Leu Thr Met Ser
1               5                   10                  15

Gln Asn Lys Asp
            20

<210> SEQ ID NO 22
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 22
```

```
Glu Pro Pro Thr Arg Thr Arg Val Asn Asn His Thr Val Thr Val Gln
1               5                   10                  15

Ala Gln Gln His
            20

<210> SEQ ID NO 23
<211> LENGTH: 14
<212> TYPE: PRT
<213> ORGANISM: Artificial Sequence
<220> FEATURE:
<223> OTHER INFORMATION: Synthetic oral-surface binding peptide

<400> SEQUENCE: 23

Gly Tyr Cys Leu Arg Gly Asp Glu Pro Ala Val Cys Ser Gly
1               5                   10

<210> SEQ ID NO 24
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 24

Leu Ser Ser Lys Asp Phe Gly Val Thr Asn Thr Asp Gln Arg Thr Tyr
1               5                   10                  15

Asp Tyr Thr Thr
            20

<210> SEQ ID NO 25
<211> LENGTH: 14
<212> TYPE: PRT
<213> ORGANISM: Artificial Sequence
<220> FEATURE:
<223> OTHER INFORMATION: Synthetic oral-surface binding peptide

<400> SEQUENCE: 25

Asn Phe Cys Glu Thr Gln Leu Asp Leu Ser Val Cys Thr Val
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Synthetic oral-surface binding peptide

<400> SEQUENCE: 26

Asn Thr Cys Gln Pro Thr Lys Asn Ala Thr Pro Cys Ser Ala
1               5                   10

<210> SEQ ID NO 27
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 27

Pro Ser Glu Pro Glu Arg Arg Asp Arg Asn Ile Ala Ala Asn Ala Gly
1               5                   10                  15

Arg Phe Asn Thr
            20

<210> SEQ ID NO 28
<211> LENGTH: 18
```

```
<212> TYPE: PRT
<213> ORGANISM: Artificial Sequence
<220> FEATURE:
<223> OTHER INFORMATION: Synthetic oral-surface binding peptide

<400> SEQUENCE: 28

Thr His Asn Met Ser His Phe Pro Pro Ser Gly His Pro Lys Arg Thr
1               5                   10                  15

Ala Thr

<210> SEQ ID NO 29
<211> LENGTH: 14
<212> TYPE: PRT
<213> ORGANISM: Artificial Sequence
<220> FEATURE:
<223> OTHER INFORMATION: Synthetic oral-surface binding peptide

<400> SEQUENCE: 29

Thr Thr Cys Pro Thr Met Gly Thr Tyr His Val Cys Trp Leu
1               5                   10

<210> SEQ ID NO 30
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 30

Tyr Cys Ala Asp His Thr Pro Asp Pro Ala Asn Pro Asn Lys Ile Cys
1               5                   10                  15

Gly Tyr Ser His
            20

<210> SEQ ID NO 31
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 31

Ala Ala Asn Pro His Thr Glu Trp Asp Arg Asp Ala Phe Gln Leu Ala
1               5                   10                  15

Met Pro Pro Lys
            20

<210> SEQ ID NO 32
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 32

Asp Leu His Pro Met Asp Pro Ser Asn Lys Arg Pro Asp Asn Pro Ser
1               5                   10                  15

Asp Leu His Thr
            20

<210> SEQ ID NO 33
<211> LENGTH: 14
<212> TYPE: PRT
<213> ORGANISM: Artificial Sequence
<220> FEATURE:
<223> OTHER INFORMATION: Synthetic oral-surface binding peptide
```

```
<400> SEQUENCE: 33

Glu Ser Cys Val Ser Asn Ala Leu Met Asn Gln Cys Ile Tyr
1               5                   10

<210> SEQ ID NO 34
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 34

His Asn Lys Ala Asp Ser Trp Asp Pro Asp Leu Pro Pro His Ala Gly
1               5                   10                  15

Met Ser Leu Gly
            20

<210> SEQ ID NO 35
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 35

Leu Asn Asp Gln Arg Lys Pro Gly Pro Pro Thr Met Pro Thr His Ser
1               5                   10                  15

Pro Ala Val Gly
            20

<210> SEQ ID NO 36
<211> LENGTH: 14
<212> TYPE: PRT
<213> ORGANISM: Artificial Sequence
<220> FEATURE:
<223> OTHER INFORMATION: Synthetic oral-surface binding peptide

<400> SEQUENCE: 36

Asn Thr Cys Ala Thr Ser Pro Asn Ser Tyr Thr Cys Ser Asn
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Synthetic oral-surface binding peptide

<400> SEQUENCE: 37

Ser Asp Cys Thr Ala Gly Leu Val Pro Pro Leu Cys Ala Thr
1               5                   10

<210> SEQ ID NO 38
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 38

Thr Ile Glu Ser Ser Gln His Ser Arg Thr His Gln Gln Asn Tyr Gly
1               5                   10                  15

Ser Thr Lys Thr
            20
```

```
<210> SEQ ID NO 39
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 39

Val Gly Thr Met Lys Gln His Pro Thr Thr Thr Gln Pro Pro Arg Val
1               5                   10                  15

Ser Ala Thr Asn
            20

<210> SEQ ID NO 40
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 40

Tyr Ser Glu Thr Pro Asn Asp Gln Lys Pro Asn Pro His Tyr Lys Val
1               5                   10                  15

Ser Gly Thr Lys
            20

<210> SEQ ID NO 41
<211> LENGTH: 8
<212> TYPE: PRT
<213> ORGANISM: Artificial Sequence
<220> FEATURE:
<223> OTHER INFORMATION: Synthetic peptide linker

<400> SEQUENCE: 41

Leu Glu Ser Gly Asp Glu Val Asp
1               5

<210> SEQ ID NO 42
<211> LENGTH: 37
<212> TYPE: PRT
<213> ORGANISM: Artificial Sequence
<220> FEATURE:
<223> OTHER INFORMATION: Synthetic peptide linker

<400> SEQUENCE: 42

Thr Ser Thr Ser Lys Ala Ser Thr Thr Thr Ser Ser Lys Thr Thr
1               5                   10                  15

Thr Thr Ser Ser Lys Thr Thr Thr Thr Thr Ser Lys Thr Ser Thr Thr
                20                  25                  30

Ser Ser Ser Ser Thr
            35

<210> SEQ ID NO 43
<211> LENGTH: 22
<212> TYPE: PRT
<213> ORGANISM: Artificial Sequence
<220> FEATURE:
<223> OTHER INFORMATION: Synthetic peptide linker

<400> SEQUENCE: 43

Gly Gln Gly Gly Tyr Gly Gly Leu Gly Ser Gln Gly Ala Gly Arg Gly
1               5                   10                  15

Gly Leu Gly Gly Gln Gly
            20
```

```
<210> SEQ ID NO 44
<211> LENGTH: 10
<212> TYPE: PRT
<213> ORGANISM: Artificial Sequence
<220> FEATURE:
<223> OTHER INFORMATION: Synthetic peptide linker

<400> SEQUENCE: 44

Gly Pro Gly Gly Tyr Gly Pro Gly Gln Gln
1               5                   10

<210> SEQ ID NO 45

<400> SEQUENCE: 45

000

<210> SEQ ID NO 46
<211> LENGTH: 9
<212> TYPE: PRT
<213> ORGANISM: Artificial Sequence
<220> FEATURE:
<223> OTHER INFORMATION: Synthetic peptide linker

<400> SEQUENCE: 46

Gly Gly Ser Gly Pro Gly Ser Gly Gly
1               5

<210> SEQ ID NO 47

<400> SEQUENCE: 47

000

<210> SEQ ID NO 48
<211> LENGTH: 5
<212> TYPE: PRT
<213> ORGANISM: Artificial Sequence
<220> FEATURE:
<223> OTHER INFORMATION: Synthetic linker

<400> SEQUENCE: 48

Gly Gly Pro Lys Lys
1               5

<210> SEQ ID NO 49

<400> SEQUENCE: 49

000

<210> SEQ ID NO 50
<211> LENGTH: 5
<212> TYPE: PRT
<213> ORGANISM: Artificial Sequence
<220> FEATURE:
<223> OTHER INFORMATION: Synthetic peptide linker

<400> SEQUENCE: 50

Gly Pro Gly Val Gly
1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic peptide linker
```

```
<400> SEQUENCE: 51

Gly Gly Gly Cys Gly Gly Gly
1               5

<210> SEQ ID NO 52
<211> LENGTH: 4
<212> TYPE: PRT
<213> ORGANISM: Artificial Sequence
<220> FEATURE:
<223> OTHER INFORMATION: Synthetic peptide linker

<400> SEQUENCE: 52

Gly Gly Gly Cys
1

<210> SEQ ID NO 53
<211> LENGTH: 14
<212> TYPE: PRT
<213> ORGANISM: Artificial Sequence
<220> FEATURE:
<223> OTHER INFORMATION: Synthetic peptide linker

<400> SEQUENCE: 53

Pro His Met Ala Ser Met Thr Gly Gly Gln Gln Met Gly Ser
1               5                   10

<210> SEQ ID NO 54
<211> LENGTH: 16
<212> TYPE: PRT
<213> ORGANISM: Artificial Sequence
<220> FEATURE:
<223> OTHER INFORMATION: Synthetic peptide linker

<400> SEQUENCE: 54

Gly Pro Glu Glu Ala Ala Lys Lys Glu Glu Ala Ala Lys Lys Pro Ala
1               5                   10                  15

<210> SEQ ID NO 55
<211> LENGTH: 14
<212> TYPE: PRT
<213> ORGANISM: Artificial Sequence
<220> FEATURE:
<223> OTHER INFORMATION: Synthetic peptide linker

<400> SEQUENCE: 55

Gly Ser Gly Gly Gly Gly Ser Gly Ser Gly Gly Gly Gly Ser
1               5                   10

<210> SEQ ID NO 56
<211> LENGTH: 37
<212> TYPE: PRT
<213> ORGANISM: Artificial Sequence
<220> FEATURE:
<223> OTHER INFORMATION: Synthetic peptide linker

<400> SEQUENCE: 56

Gly Pro Glu Pro Glu Pro Glu Pro Glu Pro Ile Pro Glu Pro Pro Lys
1               5                   10                  15

Glu Ala Pro Val Val Ile Glu Lys Pro Lys Pro Lys Pro Lys Pro Lys
            20                  25                  30

Pro Lys Pro Pro Ala
        35

<210> SEQ ID NO 57
<211> LENGTH: 60
```

```
<212> TYPE: PRT
<213> ORGANISM: artificial sequence
<220> FEATURE:
<223> OTHER INFORMATION: synthetic alpha helix forming sequence
<220> FEATURE:
<221> NAME/KEY: MISC_FEATURE
<222> LOCATION: (1)..(1)
<223> OTHER INFORMATION: Xaa = Glu or Asp
<220> FEATURE:
<221> NAME/KEY: MISC_FEATURE
<222> LOCATION: (1)..(2)
<223> OTHER INFORMATION: Xaa of residue positions 1 and 2 have opposite
      charge of Xaa at positions 5 and 6
<220> FEATURE:
<221> NAME/KEY: MISC_FEATURE
<222> LOCATION: (2)..(2)
<223> OTHER INFORMATION: Xaa = Glu or Asp
<220> FEATURE:
<221> NAME/KEY: MISC_FEATURE
<222> LOCATION: (5)..(5)
<223> OTHER INFORMATION: Xaa = Lys or Arg
<220> FEATURE:
<221> NAME/KEY: MISC_FEATURE
<222> LOCATION: (6)..(6)
<223> OTHER INFORMATION: Xaa = Lys or Arg
<220> FEATURE:
<221> NAME/KEY: MISC_FEATURE
<222> LOCATION: (7)..(8)
<223> OTHER INFORMATION: Xaa of residue positions 7 and 8 have opposite
      charge of Xaa at positions 11 and 12
<220> FEATURE:
<221> NAME/KEY: MISC_FEATURE
<222> LOCATION: (7)..(7)
<223> OTHER INFORMATION: Xaa = Glu or Asp
<220> FEATURE:
<221> NAME/KEY: MISC_FEATURE
<222> LOCATION: (8)..(8)
<223> OTHER INFORMATION: Xaa = Glu or Asp
<220> FEATURE:
<221> NAME/KEY: MISC_FEATURE
<222> LOCATION: (11)..(11)
<223> OTHER INFORMATION: Xaa = Lys or Arg
<220> FEATURE:
<221> NAME/KEY: MISC_FEATURE
<222> LOCATION: (12)..(12)
<223> OTHER INFORMATION: Xaa = Lys or Arg
<220> FEATURE:
<221> NAME/KEY: MISC_FEATURE
<222> LOCATION: (13)..(13)
<223> OTHER INFORMATION: Xaa = Glu or Asp
<220> FEATURE:
<221> NAME/KEY: MISC_FEATURE
<222> LOCATION: (13)..(14)
<223> OTHER INFORMATION: Xaa of residue positions 13 and 14 have
      opposite charge of Xaa at positions 17 and 18
<220> FEATURE:
<221> NAME/KEY: MISC_FEATURE
<222> LOCATION: (13)..(18)
<223> OTHER INFORMATION: optionally present
<220> FEATURE:
<221> NAME/KEY: MISC_FEATURE
<222> LOCATION: (14)..(14)
<223> OTHER INFORMATION: Xaa = Glu or Asp
<220> FEATURE:
<221> NAME/KEY: MISC_FEATURE
<222> LOCATION: (17)..(17)
<223> OTHER INFORMATION: Xaa = Lys or Arg
<220> FEATURE:
<221> NAME/KEY: MISC_FEATURE
<222> LOCATION: (18)..(18)
<223> OTHER INFORMATION: Xaa = Lys or Arg
<220> FEATURE:
<221> NAME/KEY: MISC_FEATURE
<222> LOCATION: (19)..(19)
<223> OTHER INFORMATION: Xaa = Glu or Asp
<220> FEATURE:
<221> NAME/KEY: MISC_FEATURE
<222> LOCATION: (19)..(20)
<223> OTHER INFORMATION: Xaa of residue positions 19 and 20 have
      opposite charge of Xaa at positions 23 and 24
```

-continued

```
<220> FEATURE:
<221> NAME/KEY: MISC_FEATURE
<222> LOCATION: (19)..(24)
<223> OTHER INFORMATION: optionally present
<220> FEATURE:
<221> NAME/KEY: MISC_FEATURE
<222> LOCATION: (20)..(20)
<223> OTHER INFORMATION: Xaa = Glu or Asp
<220> FEATURE:
<221> NAME/KEY: MISC_FEATURE
<222> LOCATION: (23)..(23)
<223> OTHER INFORMATION: Xaa = Lys or Arg
<220> FEATURE:
<221> NAME/KEY: MISC_FEATURE
<222> LOCATION: (24)..(24)
<223> OTHER INFORMATION: Xaa = Lys or Arg
<220> FEATURE:
<221> NAME/KEY: MISC_FEATURE
<222> LOCATION: (25)..(25)
<223> OTHER INFORMATION: Xaa = Glu or Asp
<220> FEATURE:
<221> NAME/KEY: MISC_FEATURE
<222> LOCATION: (25)..(26)
<223> OTHER INFORMATION: Xaa of residue positions 25 and 26 have
      opposite charge of Xaa at positions 29 and 30
<220> FEATURE:
<221> NAME/KEY: MISC_FEATURE
<222> LOCATION: (25)..(30)
<223> OTHER INFORMATION: optionally present
<220> FEATURE:
<221> NAME/KEY: MISC_FEATURE
<222> LOCATION: (26)..(26)
<223> OTHER INFORMATION: Xaa = Glu or Asp
<220> FEATURE:
<221> NAME/KEY: MISC_FEATURE
<222> LOCATION: (29)..(29)
<223> OTHER INFORMATION: Xaa = Lys or Arg
<220> FEATURE:
<221> NAME/KEY: MISC_FEATURE
<222> LOCATION: (30)..(30)
<223> OTHER INFORMATION: Xaa = Lys or Arg
<220> FEATURE:
<221> NAME/KEY: MISC_FEATURE
<222> LOCATION: (31)..(31)
<223> OTHER INFORMATION: Xaa = Glu or Asp
<220> FEATURE:
<221> NAME/KEY: MISC_FEATURE
<222> LOCATION: (31)..(32)
<223> OTHER INFORMATION: Xaa of residue positions 31 and 32 have
      opposite charge of Xaa at positions 35 and 36
<220> FEATURE:
<221> NAME/KEY: MISC_FEATURE
<222> LOCATION: (31)..(36)
<223> OTHER INFORMATION: optionally present
<220> FEATURE:
<221> NAME/KEY: MISC_FEATURE
<222> LOCATION: (32)..(32)
<223> OTHER INFORMATION: Xaa = Glu or Asp
<220> FEATURE:
<221> NAME/KEY: MISC_FEATURE
<222> LOCATION: (35)..(35)
<223> OTHER INFORMATION: Xaa = Lys or Arg
<220> FEATURE:
<221> NAME/KEY: MISC_FEATURE
<222> LOCATION: (36)..(36)
<223> OTHER INFORMATION: Xaa = Lys or Arg
<220> FEATURE:
<221> NAME/KEY: MISC_FEATURE
<222> LOCATION: (37)..(37)
<223> OTHER INFORMATION: Xaa = Glu or Asp
<220> FEATURE:
<221> NAME/KEY: MISC_FEATURE
<222> LOCATION: (37)..(38)
<223> OTHER INFORMATION: Xaa of residue positions 37 and 38 have
      opposite charge of Xaa at positions 41 and 42
<220> FEATURE:
<221> NAME/KEY: MISC_FEATURE
<222> LOCATION: (37)..(42)
<223> OTHER INFORMATION: optionally present
<220> FEATURE:
```

```
<221> NAME/KEY: MISC_FEATURE
<222> LOCATION: (38)..(38)
<223> OTHER INFORMATION: Xaa = Glu or Asp
<220> FEATURE:
<221> NAME/KEY: MISC_FEATURE
<222> LOCATION: (41)..(41)
<223> OTHER INFORMATION: Xaa = Lys or Arg
<220> FEATURE:
<221> NAME/KEY: MISC_FEATURE
<222> LOCATION: (42)..(42)
<223> OTHER INFORMATION: Xaa = Lys or Arg
<220> FEATURE:
<221> NAME/KEY: MISC_FEATURE
<222> LOCATION: (43)..(43)
<223> OTHER INFORMATION: Xaa = Glu or Asp
<220> FEATURE:
<221> NAME/KEY: MISC_FEATURE
<222> LOCATION: (43)..(44)
<223> OTHER INFORMATION: Xaa of residue positions 43 and 44 have
      opposite charge of Xaa at positions 47 and 48
<220> FEATURE:
<221> NAME/KEY: MISC_FEATURE
<222> LOCATION: (43)..(48)
<223> OTHER INFORMATION: optionally present
<220> FEATURE:
<221> NAME/KEY: MISC_FEATURE
<222> LOCATION: (44)..(44)
<223> OTHER INFORMATION: Xaa = Glu or Asp
<220> FEATURE:
<221> NAME/KEY: MISC_FEATURE
<222> LOCATION: (47)..(47)
<223> OTHER INFORMATION: Xaa = Lys or Arg
<220> FEATURE:
<221> NAME/KEY: MISC_FEATURE
<222> LOCATION: (48)..(48)
<223> OTHER INFORMATION: Xaa = Lys or Arg
<220> FEATURE:
<221> NAME/KEY: MISC_FEATURE
<222> LOCATION: (49)..(49)
<223> OTHER INFORMATION: Xaa = Glu or Asp
<220> FEATURE:
<221> NAME/KEY: MISC_FEATURE
<222> LOCATION: (49)..(50)
<223> OTHER INFORMATION: Xaa of residue positions 49 and 50 have
      opposite charge of Xaa at positions 53 and 54
<220> FEATURE:
<221> NAME/KEY: MISC_FEATURE
<222> LOCATION: (49)..(54)
<223> OTHER INFORMATION: optionally present
<220> FEATURE:
<221> NAME/KEY: MISC_FEATURE
<222> LOCATION: (50)..(50)
<223> OTHER INFORMATION: Xaa = Glu or Asp
<220> FEATURE:
<221> NAME/KEY: MISC_FEATURE
<222> LOCATION: (53)..(53)
<223> OTHER INFORMATION: Xaa = Lys or Arg
<220> FEATURE:
<221> NAME/KEY: MISC_FEATURE
<222> LOCATION: (54)..(54)
<223> OTHER INFORMATION: Xaa = Lys or Arg
<220> FEATURE:
<221> NAME/KEY: MISC_FEATURE
<222> LOCATION: (55)..(55)
<223> OTHER INFORMATION: Xaa = Glu or Asp
<220> FEATURE:
<221> NAME/KEY: MISC_FEATURE
<222> LOCATION: (55)..(56)
<223> OTHER INFORMATION: Xaa of residue positions 55 and 56 have
      opposite charge of Xaa at positions 59 and 60
<220> FEATURE:
<221> NAME/KEY: MISC_FEATURE
<222> LOCATION: (55)..(60)
<223> OTHER INFORMATION: optionally present
<220> FEATURE:
<221> NAME/KEY: MISC_FEATURE
<222> LOCATION: (56)..(56)
<223> OTHER INFORMATION: Xaa = Glu or Asp
<220> FEATURE:
<221> NAME/KEY: MISC_FEATURE
```

```
<222> LOCATION: (59)..(59)
<223> OTHER INFORMATION: Xaa = Lys or Arg
<220> FEATURE:
<221> NAME/KEY: MISC_FEATURE
<222> LOCATION: (60)..(60)
<223> OTHER INFORMATION: Xaa = Lys or Arg

<400> SEQUENCE: 57

Xaa Xaa Ala Ala Xaa Xaa Xaa Xaa Ala Ala Xaa Xaa Xaa Xaa Ala Ala
1               5                   10                  15

Xaa Xaa Xaa Xaa Ala Ala Xaa Xaa Xaa Xaa Ala Ala Xaa Xaa Xaa Xaa
                20                  25                  30

Ala Ala Xaa Xaa Xaa Xaa Ala Ala Xaa Xaa Xaa Xaa Ala Ala Xaa Xaa
        35                  40                  45

Xaa Xaa Ala Ala Xaa Xaa Xaa Xaa Ala Ala Xaa Xaa
    50                  55                  60

<210> SEQ ID NO 58
<211> LENGTH: 55
<212> TYPE: PRT
<213> ORGANISM: artificial sequence
<220> FEATURE:
<223> OTHER INFORMATION: synthetic alpha helix forming sequence
<220> FEATURE:
<221> NAME/KEY: MISC_FEATURE
<222> LOCATION: (1)..(1)
<223> OTHER INFORMATION: Xaa = Glu or Asp
<220> FEATURE:
<221> NAME/KEY: MISC_FEATURE
<222> LOCATION: (1)..(1)
<223> OTHER INFORMATION: Xaa of residue position 1 is oppositely charged
      from Xaa of residue position 5.
<220> FEATURE:
<221> NAME/KEY: MISC_FEATURE
<222> LOCATION: (5)..(5)
<223> OTHER INFORMATION: Xaa = Lys or Arg
<220> FEATURE:
<221> NAME/KEY: MISC_FEATURE
<222> LOCATION: (6)..(6)
<223> OTHER INFORMATION: Xaa = Glu or Asp
<220> FEATURE:
<221> NAME/KEY: MISC_FEATURE
<222> LOCATION: (6)..(6)
<223> OTHER INFORMATION: Xaa of residue position 6 is oppositely charged
      from Xaa of residue position 10.
<220> FEATURE:
<221> NAME/KEY: MISC_FEATURE
<222> LOCATION: (10)..(10)
<223> OTHER INFORMATION: Xaa = Lys or Arg
<220> FEATURE:
<221> NAME/KEY: MISC_FEATURE
<222> LOCATION: (11)..(11)
<223> OTHER INFORMATION: Xaa = Glu or Asp
<220> FEATURE:
<221> NAME/KEY: MISC_FEATURE
<222> LOCATION: (11)..(11)
<223> OTHER INFORMATION: Xaa of residue position 11 is oppositely
      charged from Xaa of residue position 15.
<220> FEATURE:
<221> NAME/KEY: MISC_FEATURE
<222> LOCATION: (11)..(15)
<223> OTHER INFORMATION: optionally present
<220> FEATURE:
<221> NAME/KEY: MISC_FEATURE
<222> LOCATION: (15)..(15)
<223> OTHER INFORMATION: Xaa = Lys or Arg
<220> FEATURE:
<221> NAME/KEY: MISC_FEATURE
<222> LOCATION: (16)..(16)
<223> OTHER INFORMATION: Xaa = Glu or Asp
<220> FEATURE:
<221> NAME/KEY: MISC_FEATURE
<222> LOCATION: (16)..(16)
<223> OTHER INFORMATION: Xaa of residue position 16 is oppositely
      charged from Xaa of residue position 20.
```

```
<220> FEATURE:
<221> NAME/KEY: MISC_FEATURE
<222> LOCATION: (16)..(20)
<223> OTHER INFORMATION: optionally present
<220> FEATURE:
<221> NAME/KEY: MISC_FEATURE
<222> LOCATION: (20)..(20)
<223> OTHER INFORMATION: Xaa = Lys or Arg
<220> FEATURE:
<221> NAME/KEY: MISC_FEATURE
<222> LOCATION: (21)..(21)
<223> OTHER INFORMATION: Xaa = Glu or Asp
<220> FEATURE:
<221> NAME/KEY: MISC_FEATURE
<222> LOCATION: (21)..(21)
<223> OTHER INFORMATION: Xaa of residue position 21 is oppositely
      charged from Xaa of residue position 25.
<220> FEATURE:
<221> NAME/KEY: MISC_FEATURE
<222> LOCATION: (21)..(25)
<223> OTHER INFORMATION: optionally present
<220> FEATURE:
<221> NAME/KEY: MISC_FEATURE
<222> LOCATION: (25)..(25)
<223> OTHER INFORMATION: Xaa = Lys or Arg
<220> FEATURE:
<221> NAME/KEY: MISC_FEATURE
<222> LOCATION: (26)..(26)
<223> OTHER INFORMATION: Xaa = Glu or Asp
<220> FEATURE:
<221> NAME/KEY: MISC_FEATURE
<222> LOCATION: (26)..(26)
<223> OTHER INFORMATION: Xaa of residue position 26 is oppositely
      charged from Xaa of residue position 30.
<220> FEATURE:
<221> NAME/KEY: MISC_FEATURE
<222> LOCATION: (26)..(30)
<223> OTHER INFORMATION: optionally present
<220> FEATURE:
<221> NAME/KEY: MISC_FEATURE
<222> LOCATION: (30)..(30)
<223> OTHER INFORMATION: Xaa = Lys or Arg
<220> FEATURE:
<221> NAME/KEY: MISC_FEATURE
<222> LOCATION: (31)..(31)
<223> OTHER INFORMATION: Xaa = Glu or Asp
<220> FEATURE:
<221> NAME/KEY: MISC_FEATURE
<222> LOCATION: (31)..(31)
<223> OTHER INFORMATION: Xaa of residue position 31 is oppositely
      charged from Xaa of residue position 35.
<220> FEATURE:
<221> NAME/KEY: MISC_FEATURE
<222> LOCATION: (31)..(35)
<223> OTHER INFORMATION: optionally present
<220> FEATURE:
<221> NAME/KEY: MISC_FEATURE
<222> LOCATION: (35)..(35)
<223> OTHER INFORMATION: Xaa = Lys or Arg
<220> FEATURE:
<221> NAME/KEY: MISC_FEATURE
<222> LOCATION: (36)..(36)
<223> OTHER INFORMATION: Xaa = Glu or Asp
<220> FEATURE:
<221> NAME/KEY: MISC_FEATURE
<222> LOCATION: (36)..(36)
<223> OTHER INFORMATION: Xaa of residue position 36 is oppositely
      charged from Xaa of residue position 40.
<220> FEATURE:
<221> NAME/KEY: MISC_FEATURE
<222> LOCATION: (36)..(40)
<223> OTHER INFORMATION: optionally present
<220> FEATURE:
<221> NAME/KEY: MISC_FEATURE
<222> LOCATION: (40)..(40)
<223> OTHER INFORMATION: Xaa = Lys or Arg
<220> FEATURE:
<221> NAME/KEY: MISC_FEATURE
<222> LOCATION: (41)..(41)
<223> OTHER INFORMATION: Xaa = Glu or Asp
```

```
<220> FEATURE:
<221> NAME/KEY: MISC_FEATURE
<222> LOCATION: (41)..(41)
<223> OTHER INFORMATION: Xaa of residue position 41 is oppositely
      charged from Xaa of residue position 45.
<220> FEATURE:
<221> NAME/KEY: MISC_FEATURE
<222> LOCATION: (41)..(45)
<223> OTHER INFORMATION: optionally present
<220> FEATURE:
<221> NAME/KEY: MISC_FEATURE
<222> LOCATION: (45)..(45)
<223> OTHER INFORMATION: Xaa = Lys or Arg
<220> FEATURE:
<221> NAME/KEY: MISC_FEATURE
<222> LOCATION: (46)..(46)
<223> OTHER INFORMATION: Xaa = Glu or Asp
<220> FEATURE:
<221> NAME/KEY: MISC_FEATURE
<222> LOCATION: (46)..(46)
<223> OTHER INFORMATION: Xaa of residue position 46 is oppositely
      charged from Xaa of residue position 50.
<220> FEATURE:
<221> NAME/KEY: MISC_FEATURE
<222> LOCATION: (46)..(50)
<223> OTHER INFORMATION: optionally present
<220> FEATURE:
<221> NAME/KEY: MISC_FEATURE
<222> LOCATION: (50)..(50)
<223> OTHER INFORMATION: Xaa = Lys or Arg
<220> FEATURE:
<221> NAME/KEY: MISC_FEATURE
<222> LOCATION: (51)..(51)
<223> OTHER INFORMATION: Xaa = Glu or Asp
<220> FEATURE:
<221> NAME/KEY: MISC_FEATURE
<222> LOCATION: (51)..(51)
<223> OTHER INFORMATION: Xaa of residue position 51 is oppositely
      charged from Xaa of residue position 55.
<220> FEATURE:
<221> NAME/KEY: MISC_FEATURE
<222> LOCATION: (51)..(55)
<223> OTHER INFORMATION: optionally present
<220> FEATURE:
<221> NAME/KEY: MISC_FEATURE
<222> LOCATION: (55)..(55)
<223> OTHER INFORMATION: Xaa = Lys or Arg

<400> SEQUENCE: 58

Xaa Ala Ala Ala Xaa Xaa Ala Ala Ala Xaa Xaa Ala Ala Ala Xaa Xaa
1               5                   10                  15

Ala Ala Ala Xaa Xaa Ala Ala Ala Xaa Xaa Ala Ala Ala Xaa Xaa Ala
                20                  25                  30

Ala Ala Xaa Xaa Ala Ala Ala Xaa Xaa Ala Ala Ala Xaa Xaa Ala Ala
            35                  40                  45

Ala Xaa Xaa Ala Ala Ala Xaa
    50                  55

<210> SEQ ID NO 59
<211> LENGTH: 77
<212> TYPE: PRT
<213> ORGANISM: artificial sequence
<220> FEATURE:
<223> OTHER INFORMATION: synthetic alpha helix forming sequence
<220> FEATURE:
<221> NAME/KEY: MISC_FEATURE
<222> LOCATION: (1)..(1)
<223> OTHER INFORMATION: Xaa = Glu or Asp
<220> FEATURE:
<221> NAME/KEY: MISC_FEATURE
<222> LOCATION: (1)..(1)
<223> OTHER INFORMATION: Xaa of residue position 1 has opposite
      charge from Xaa at residue position 5
<220> FEATURE:
<221> NAME/KEY: MISC_FEATURE
```

```
<222> LOCATION: (5)..(5)
<223> OTHER INFORMATION: Xaa = Lys or Arg
<220> FEATURE:
<221> NAME/KEY: MISC_FEATURE
<222> LOCATION: (6)..(6)
<223> OTHER INFORMATION: Xaa = Leu, Val, Ile, Phe, Trp, Met or Tyr
<220> FEATURE:
<221> NAME/KEY: MISC_FEATURE
<222> LOCATION: (7)..(7)
<223> OTHER INFORMATION: Xaa = Leu, Val, Ile, Phe, Trp, Met or Tyr
<220> FEATURE:
<221> NAME/KEY: MISC_FEATURE
<222> LOCATION: (8)..(8)
<223> OTHER INFORMATION: Xaa = Glu or Asp
<220> FEATURE:
<221> NAME/KEY: MISC_FEATURE
<222> LOCATION: (8)..(8)
<223> OTHER INFORMATION: Xaa of residue position 8 has opposite charge
      from Xaa at residue position 12
<220> FEATURE:
<221> NAME/KEY: MISC_FEATURE
<222> LOCATION: (12)..(12)
<223> OTHER INFORMATION: Xaa = Lys or Arg
<220> FEATURE:
<221> NAME/KEY: MISC_FEATURE
<222> LOCATION: (13)..(13)
<223> OTHER INFORMATION: Xaa = Leu, Val, Ile, Phe, Trp, Met or Tyr
<220> FEATURE:
<221> NAME/KEY: MISC_FEATURE
<222> LOCATION: (14)..(14)
<223> OTHER INFORMATION: Xaa = Leu, Val, Ile, Phe, Trp, Met or Tyr
<220> FEATURE:
<221> NAME/KEY: MISC_FEATURE
<222> LOCATION: (15)..(15)
<223> OTHER INFORMATION: Xaa = Glu or Asp
<220> FEATURE:
<221> NAME/KEY: MISC_FEATURE
<222> LOCATION: (15)..(15)
<223> OTHER INFORMATION: Xaa of residue position 15 has opposite charge
      from Xaa at residue position 19
<220> FEATURE:
<221> NAME/KEY: MISC_FEATURE
<222> LOCATION: (15)..(21)
<223> OTHER INFORMATION: optionally present
<220> FEATURE:
<221> NAME/KEY: MISC_FEATURE
<222> LOCATION: (19)..(19)
<223> OTHER INFORMATION: Xaa = Lys or Arg
<220> FEATURE:
<221> NAME/KEY: MISC_FEATURE
<222> LOCATION: (20)..(20)
<223> OTHER INFORMATION: Xaa = Leu, Val, Ile, Phe, Trp, Met or Tyr
<220> FEATURE:
<221> NAME/KEY: MISC_FEATURE
<222> LOCATION: (21)..(21)
<223> OTHER INFORMATION: Xaa = Leu, Val, Ile, Phe, Trp, Met or Tyr
<220> FEATURE:
<221> NAME/KEY: MISC_FEATURE
<222> LOCATION: (22)..(22)
<223> OTHER INFORMATION: Xaa = Glu or Asp
<220> FEATURE:
<221> NAME/KEY: MISC_FEATURE
<222> LOCATION: (22)..(22)
<223> OTHER INFORMATION: Xaa of residue position 22 has opposite charge
      from Xaa at residue position 26
<220> FEATURE:
<221> NAME/KEY: MISC_FEATURE
<222> LOCATION: (22)..(28)
<223> OTHER INFORMATION: optionally present
<220> FEATURE:
<221> NAME/KEY: MISC_FEATURE
<222> LOCATION: (26)..(26)
<223> OTHER INFORMATION: Xaa = Lys or Arg
<220> FEATURE:
<221> NAME/KEY: MISC_FEATURE
<222> LOCATION: (27)..(27)
<223> OTHER INFORMATION: Xaa = Leu, Val, Ile, Phe, Trp, Met or Tyr
<220> FEATURE:
<221> NAME/KEY: MISC_FEATURE
<222> LOCATION: (28)..(28)
```

```
<223> OTHER INFORMATION: Xaa = Leu, Val, Ile, Phe, Trp, Met or Tyr
<220> FEATURE:
<221> NAME/KEY: MISC_FEATURE
<222> LOCATION: (29)..(29)
<223> OTHER INFORMATION: Xaa = Glu or Asp
<220> FEATURE:
<221> NAME/KEY: MISC_FEATURE
<222> LOCATION: (29)..(29)
<223> OTHER INFORMATION: Xaa of residue position 29 has opposite charge
      from Xaa at residue position 33
<220> FEATURE:
<221> NAME/KEY: MISC_FEATURE
<222> LOCATION: (29)..(35)
<223> OTHER INFORMATION: optionally present
<220> FEATURE:
<221> NAME/KEY: MISC_FEATURE
<222> LOCATION: (33)..(33)
<223> OTHER INFORMATION: Xaa = Lys or Arg
<220> FEATURE:
<221> NAME/KEY: MISC_FEATURE
<222> LOCATION: (34)..(34)
<223> OTHER INFORMATION: Xaa = Leu, Val, Ile, Phe, Trp, Met or Tyr
<220> FEATURE:
<221> NAME/KEY: MISC_FEATURE
<222> LOCATION: (35)..(35)
<223> OTHER INFORMATION: Xaa = Leu, Val, Ile, Phe, Trp, Met or Tyr
<220> FEATURE:
<221> NAME/KEY: MISC_FEATURE
<222> LOCATION: (36)..(36)
<223> OTHER INFORMATION: Xaa = Glu or Asp
<220> FEATURE:
<221> NAME/KEY: MISC_FEATURE
<222> LOCATION: (36)..(36)
<223> OTHER INFORMATION: Xaa of residue position 36 has opposite charge
      from Xaa at residue position 40
<220> FEATURE:
<221> NAME/KEY: MISC_FEATURE
<222> LOCATION: (36)..(42)
<223> OTHER INFORMATION: optionally present
<220> FEATURE:
<221> NAME/KEY: MISC_FEATURE
<222> LOCATION: (40)..(40)
<223> OTHER INFORMATION: Xaa = Lys or Arg
<220> FEATURE:
<221> NAME/KEY: MISC_FEATURE
<222> LOCATION: (41)..(41)
<223> OTHER INFORMATION: Xaa = Leu, Val, Ile, Phe, Trp, Met or Tyr
<220> FEATURE:
<221> NAME/KEY: MISC_FEATURE
<222> LOCATION: (42)..(42)
<223> OTHER INFORMATION: Xaa = Leu, Val, Ile, Phe, Trp, Met or Tyr
<220> FEATURE:
<221> NAME/KEY: MISC_FEATURE
<222> LOCATION: (43)..(43)
<223> OTHER INFORMATION: Xaa = Glu or Asp
<220> FEATURE:
<221> NAME/KEY: MISC_FEATURE
<222> LOCATION: (43)..(43)
<223> OTHER INFORMATION: Xaa of residue position 43 has opposite charge
      from Xaa at residue position 47
<220> FEATURE:
<221> NAME/KEY: MISC_FEATURE
<222> LOCATION: (43)..(49)
<223> OTHER INFORMATION: optionally present
<220> FEATURE:
<221> NAME/KEY: MISC_FEATURE
<222> LOCATION: (47)..(47)
<223> OTHER INFORMATION: Xaa = Lys or Arg
<220> FEATURE:
<221> NAME/KEY: MISC_FEATURE
<222> LOCATION: (48)..(48)
<223> OTHER INFORMATION: Xaa = Leu, Val, Ile, Phe, Trp, Met or Tyr
<220> FEATURE:
<221> NAME/KEY: MISC_FEATURE
<222> LOCATION: (49)..(49)
<223> OTHER INFORMATION: Xaa = Leu, Val, Ile, Phe, Trp, Met or Tyr
<220> FEATURE:
<221> NAME/KEY: MISC_FEATURE
<222> LOCATION: (50)..(50)
<223> OTHER INFORMATION: Xaa = Glu or Asp
```

```
<220> FEATURE:
<221> NAME/KEY: MISC_FEATURE
<222> LOCATION: (50)..(50)
<223> OTHER INFORMATION: Xaa of residue position 50 has opposite charge
      from Xaa at residue position 54
<220> FEATURE:
<221> NAME/KEY: MISC_FEATURE
<222> LOCATION: (50)..(56)
<223> OTHER INFORMATION: optionally present
<220> FEATURE:
<221> NAME/KEY: MISC_FEATURE
<222> LOCATION: (54)..(54)
<223> OTHER INFORMATION: Xaa = Lys or Arg
<220> FEATURE:
<221> NAME/KEY: MISC_FEATURE
<222> LOCATION: (55)..(55)
<223> OTHER INFORMATION: Xaa = Leu, Val, Ile, Phe, Trp, Met or Tyr
<220> FEATURE:
<221> NAME/KEY: MISC_FEATURE
<222> LOCATION: (56)..(56)
<223> OTHER INFORMATION: Xaa = Leu, Val, Ile, Phe, Trp, Met or Tyr
<220> FEATURE:
<221> NAME/KEY: MISC_FEATURE
<222> LOCATION: (57)..(57)
<223> OTHER INFORMATION: Xaa = Glu or Asp
<220> FEATURE:
<221> NAME/KEY: MISC_FEATURE
<222> LOCATION: (57)..(57)
<223> OTHER INFORMATION: Xaa of residue position 57 has opposite charge
      from Xaa at residue position 61
<220> FEATURE:
<221> NAME/KEY: MISC_FEATURE
<222> LOCATION: (57)..(63)
<223> OTHER INFORMATION: optionally present
<220> FEATURE:
<221> NAME/KEY: MISC_FEATURE
<222> LOCATION: (61)..(61)
<223> OTHER INFORMATION: Xaa = Lys or Arg
<220> FEATURE:
<221> NAME/KEY: MISC_FEATURE
<222> LOCATION: (62)..(62)
<223> OTHER INFORMATION: Xaa = Leu, Val, Ile, Phe, Trp, Met or Tyr
<220> FEATURE:
<221> NAME/KEY: MISC_FEATURE
<222> LOCATION: (63)..(63)
<223> OTHER INFORMATION: Xaa = Leu, Val, Ile, Phe, Trp, Met or Tyr
<220> FEATURE:
<221> NAME/KEY: MISC_FEATURE
<222> LOCATION: (64)..(64)
<223> OTHER INFORMATION: Xaa = Glu or Asp
<220> FEATURE:
<221> NAME/KEY: MISC_FEATURE
<222> LOCATION: (64)..(64)
<223> OTHER INFORMATION: Xaa of residue position 64 has opposite charge
      from Xaa at residue position 68
<220> FEATURE:
<221> NAME/KEY: MISC_FEATURE
<222> LOCATION: (64)..(70)
<223> OTHER INFORMATION: optionally present
<220> FEATURE:
<221> NAME/KEY: MISC_FEATURE
<222> LOCATION: (68)..(68)
<223> OTHER INFORMATION: Xaa = Lys or Arg
<220> FEATURE:
<221> NAME/KEY: MISC_FEATURE
<222> LOCATION: (69)..(69)
<223> OTHER INFORMATION: Xaa = Leu, Val, Ile, Phe, Trp, Met or Tyr
<220> FEATURE:
<221> NAME/KEY: MISC_FEATURE
<222> LOCATION: (70)..(70)
<223> OTHER INFORMATION: Xaa = Leu, Val, Ile, Phe, Trp, Met or Tyr
<220> FEATURE:
<221> NAME/KEY: MISC_FEATURE
<222> LOCATION: (71)..(71)
<223> OTHER INFORMATION: Xaa = Glu or Asp
<220> FEATURE:
<221> NAME/KEY: MISC_FEATURE
<222> LOCATION: (71)..(71)
<223> OTHER INFORMATION: Xaa of residue position 71 has opposite charge
      from Xaa at residue position 75
```

```
<220> FEATURE:
<221> NAME/KEY: MISC_FEATURE
<222> LOCATION: (71)..(77)
<223> OTHER INFORMATION: optionally present
<220> FEATURE:
<221> NAME/KEY: MISC_FEATURE
<222> LOCATION: (75)..(75)
<223> OTHER INFORMATION: Xaa = Lys or Arg
<220> FEATURE:
<221> NAME/KEY: MISC_FEATURE
<222> LOCATION: (76)..(76)
<223> OTHER INFORMATION: Xaa = Leu, Val, Ile, Phe, Trp, Met or Tyr
<220> FEATURE:
<221> NAME/KEY: MISC_FEATURE
<222> LOCATION: (77)..(77)
<223> OTHER INFORMATION: Xaa = Leu, Val, Ile, Phe, Trp, Met or Tyr

<400> SEQUENCE: 59

Xaa Ala Ala Ala Xaa Xaa Xaa Xaa Ala Ala Ala Xaa Xaa Xaa Xaa Ala
1               5                   10                  15

Ala Ala Xaa Xaa Xaa Xaa Ala Ala Xaa Xaa Xaa Xaa Ala Ala Ala
            20                  25                  30

Xaa Xaa Xaa Xaa Ala Ala Ala Xaa Xaa Xaa Xaa Ala Ala Ala Xaa Xaa
        35                  40                  45

Xaa Xaa Ala Ala Ala Xaa Xaa Xaa Xaa Ala Ala Ala Xaa Xaa Xaa Xaa
    50                  55                  60

Ala Ala Ala Xaa Xaa Xaa Xaa Ala Ala Ala Xaa Xaa Xaa
65                  70                  75

<210> SEQ ID NO 60
<211> LENGTH: 40
<212> TYPE: PRT
<213> ORGANISM: artificial sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa = Glu, Asp, Lys or Arg
<220> FEATURE:
<221> NAME/KEY: MISC_FEATURE
<222> LOCATION: (3)..(3)
<223> OTHER INFORMATION: Xaa = Glu, Asp, Lys or Arg
<220> FEATURE:
<221> NAME/KEY: MISC_FEATURE
<222> LOCATION: (5)..(5)
<223> OTHER INFORMATION: Xaa = Glu, Asp, Lys or Arg
<220> FEATURE:
<221> NAME/KEY: MISC_FEATURE
<222> LOCATION: (5)..(6)
<223> OTHER INFORMATION: optionally present
<220> FEATURE:
<221> NAME/KEY: MISC_FEATURE
<222> LOCATION: (7)..(7)
<223> OTHER INFORMATION: Xaa = Glu, Asp, Lys or Arg
<220> FEATURE:
<221> NAME/KEY: MISC_FEATURE
<222> LOCATION: (7)..(8)
<223> OTHER INFORMATION: optionally present
<220> FEATURE:
<221> NAME/KEY: MISC_FEATURE
<222> LOCATION: (9)..(9)
<223> OTHER INFORMATION: Xaa = Glu, Asp, Lys or Arg
<220> FEATURE:
<221> NAME/KEY: MISC_FEATURE
<222> LOCATION: (9)..(10)
<223> OTHER INFORMATION: optionally present
<220> FEATURE:
<221> NAME/KEY: MISC_FEATURE
<222> LOCATION: (11)..(11)
<223> OTHER INFORMATION: Xaa = Glu, Asp, Lys or Arg
<220> FEATURE:
<221> NAME/KEY: MISC_FEATURE
<222> LOCATION: (11)..(12)
```

```
<223> OTHER INFORMATION: optionally present
<220> FEATURE:
<221> NAME/KEY: MISC_FEATURE
<222> LOCATION: (13)..(13)
<223> OTHER INFORMATION: Xaa = Glu, Asp, Lys or Arg
<220> FEATURE:
<221> NAME/KEY: MISC_FEATURE
<222> LOCATION: (13)..(14)
<223> OTHER INFORMATION: optionally present
<220> FEATURE:
<221> NAME/KEY: MISC_FEATURE
<222> LOCATION: (15)..(15)
<223> OTHER INFORMATION: Xaa = Glu, Asp, Lys or Arg
<220> FEATURE:
<221> NAME/KEY: MISC_FEATURE
<222> LOCATION: (15)..(16)
<223> OTHER INFORMATION: optionally present
<220> FEATURE:
<221> NAME/KEY: MISC_FEATURE
<222> LOCATION: (17)..(17)
<223> OTHER INFORMATION: Xaa = Glu, Asp, Lys or Arg
<220> FEATURE:
<221> NAME/KEY: MISC_FEATURE
<222> LOCATION: (17)..(18)
<223> OTHER INFORMATION: optionally present
<220> FEATURE:
<221> NAME/KEY: MISC_FEATURE
<222> LOCATION: (19)..(19)
<223> OTHER INFORMATION: Xaa = Glu, Asp, Lys or Arg
<220> FEATURE:
<221> NAME/KEY: MISC_FEATURE
<222> LOCATION: (19)..(20)
<223> OTHER INFORMATION: optionally present
<220> FEATURE:
<221> NAME/KEY: MISC_FEATURE
<222> LOCATION: (21)..(21)
<223> OTHER INFORMATION: Xaa = Glu, Asp, Lys or Arg
<220> FEATURE:
<221> NAME/KEY: MISC_FEATURE
<222> LOCATION: (21)..(22)
<223> OTHER INFORMATION: optionally present
<220> FEATURE:
<221> NAME/KEY: MISC_FEATURE
<222> LOCATION: (23)..(23)
<223> OTHER INFORMATION: Xaa = Glu, Asp, Lys or Arg
<220> FEATURE:
<221> NAME/KEY: MISC_FEATURE
<222> LOCATION: (23)..(24)
<223> OTHER INFORMATION: optionally present
<220> FEATURE:
<221> NAME/KEY: MISC_FEATURE
<222> LOCATION: (25)..(25)
<223> OTHER INFORMATION: Xaa = Glu, Asp, Lys or Arg
<220> FEATURE:
<221> NAME/KEY: MISC_FEATURE
<222> LOCATION: (25)..(26)
<223> OTHER INFORMATION: optionally present
<220> FEATURE:
<221> NAME/KEY: MISC_FEATURE
<222> LOCATION: (27)..(27)
<223> OTHER INFORMATION: Xaa = Glu, Asp, Lys or Arg
<220> FEATURE:
<221> NAME/KEY: MISC_FEATURE
<222> LOCATION: (27)..(28)
<223> OTHER INFORMATION: optionally present
<220> FEATURE:
<221> NAME/KEY: MISC_FEATURE
<222> LOCATION: (29)..(29)
<223> OTHER INFORMATION: Xaa = Glu, Asp, Lys or Arg
<220> FEATURE:
<221> NAME/KEY: MISC_FEATURE
<222> LOCATION: (29)..(30)
<223> OTHER INFORMATION: optionally present
<220> FEATURE:
<221> NAME/KEY: MISC_FEATURE
<222> LOCATION: (31)..(31)
<223> OTHER INFORMATION: Xaa = Glu, Asp, Lys or Arg
<220> FEATURE:
<221> NAME/KEY: MISC_FEATURE
<222> LOCATION: (31)..(32)
```

```
<223> OTHER INFORMATION: optionally present
<220> FEATURE:
<221> NAME/KEY: MISC_FEATURE
<222> LOCATION: (33)..(33)
<223> OTHER INFORMATION: Xaa = Glu, Asp, Lys or Arg
<220> FEATURE:
<221> NAME/KEY: MISC_FEATURE
<222> LOCATION: (33)..(34)
<223> OTHER INFORMATION: optionally present
<220> FEATURE:
<221> NAME/KEY: MISC_FEATURE
<222> LOCATION: (35)..(35)
<223> OTHER INFORMATION: Xaa = Glu, Asp, Lys or Arg
<220> FEATURE:
<221> NAME/KEY: MISC_FEATURE
<222> LOCATION: (35)..(36)
<223> OTHER INFORMATION: optionally present
<220> FEATURE:
<221> NAME/KEY: MISC_FEATURE
<222> LOCATION: (37)..(37)
<223> OTHER INFORMATION: Xaa = Glu, Asp, Lys or Arg
<220> FEATURE:
<221> NAME/KEY: MISC_FEATURE
<222> LOCATION: (37)..(38)
<223> OTHER INFORMATION: optionally present
<220> FEATURE:
<221> NAME/KEY: MISC_FEATURE
<222> LOCATION: (39)..(39)
<223> OTHER INFORMATION: Xaa = Glu, Asp, Lys or Arg
<220> FEATURE:
<221> NAME/KEY: MISC_FEATURE
<222> LOCATION: (39)..(40)
<223> OTHER INFORMATION: optionally present

<400> SEQUENCE: 60

Xaa Pro Xaa Pro Xaa Pro Xaa Pro Xaa Pro Xaa Pro Xaa Pro Xaa Pro
1               5                   10                  15

Xaa Pro Xaa Pro Xaa Pro Xaa Pro Xaa Pro Xaa Pro Xaa Pro Xaa Pro
            20                  25                  30

Xaa Pro Xaa Pro Xaa Pro Xaa Pro
        35                  40

<210> SEQ ID NO 61
<211> LENGTH: 40
<212> TYPE: PRT
<213> ORGANISM: artificial sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa = Glu, Asp, Lys or Arg
<220> FEATURE:
<221> NAME/KEY: MISC_FEATURE
<222> LOCATION: (4)..(4)
<223> OTHER INFORMATION: Xaa = Glu, Asp, Lys or Arg
<220> FEATURE:
<221> NAME/KEY: MISC_FEATURE
<222> LOCATION: (5)..(6)
<223> OTHER INFORMATION: optionally present
<220> FEATURE:
<221> NAME/KEY: MISC_FEATURE
<222> LOCATION: (6)..(6)
<223> OTHER INFORMATION: Xaa = Glu, Asp, Lys or Arg
<220> FEATURE:
<221> NAME/KEY: MISC_FEATURE
<222> LOCATION: (7)..(8)
<223> OTHER INFORMATION: optionally present
<220> FEATURE:
<221> NAME/KEY: MISC_FEATURE
<222> LOCATION: (8)..(8)
<223> OTHER INFORMATION: Xaa = Glu, Asp, Lys or Arg
<220> FEATURE:
<221> NAME/KEY: MISC_FEATURE
<222> LOCATION: (9)..(10)
<223> OTHER INFORMATION: optionally present
```

```
<220> FEATURE:
<221> NAME/KEY: MISC_FEATURE
<222> LOCATION: (10)..(10)
<223> OTHER INFORMATION: Xaa = Glu, Asp, Lys or Arg
<220> FEATURE:
<221> NAME/KEY: MISC_FEATURE
<222> LOCATION: (11)..(12)
<223> OTHER INFORMATION: optionally present
<220> FEATURE:
<221> NAME/KEY: MISC_FEATURE
<222> LOCATION: (12)..(12)
<223> OTHER INFORMATION: Xaa = Glu, Asp, Lys or Arg
<220> FEATURE:
<221> NAME/KEY: MISC_FEATURE
<222> LOCATION: (13)..(14)
<223> OTHER INFORMATION: optionally present
<220> FEATURE:
<221> NAME/KEY: MISC_FEATURE
<222> LOCATION: (14)..(14)
<223> OTHER INFORMATION: Xaa = Glu, Asp, Lys or Arg
<220> FEATURE:
<221> NAME/KEY: MISC_FEATURE
<222> LOCATION: (15)..(16)
<223> OTHER INFORMATION: optionally present
<220> FEATURE:
<221> NAME/KEY: MISC_FEATURE
<222> LOCATION: (16)..(16)
<223> OTHER INFORMATION: Xaa = Glu, Asp, Lys or Arg
<220> FEATURE:
<221> NAME/KEY: MISC_FEATURE
<222> LOCATION: (17)..(18)
<223> OTHER INFORMATION: optionally present
<220> FEATURE:
<221> NAME/KEY: MISC_FEATURE
<222> LOCATION: (18)..(18)
<223> OTHER INFORMATION: Xaa = Glu, Asp, Lys or Arg
<220> FEATURE:
<221> NAME/KEY: MISC_FEATURE
<222> LOCATION: (19)..(20)
<223> OTHER INFORMATION: optionally present
<220> FEATURE:
<221> NAME/KEY: MISC_FEATURE
<222> LOCATION: (20)..(20)
<223> OTHER INFORMATION: Xaa = Glu, Asp, Lys or Arg
<220> FEATURE:
<221> NAME/KEY: MISC_FEATURE
<222> LOCATION: (21)..(22)
<223> OTHER INFORMATION: optionally present
<220> FEATURE:
<221> NAME/KEY: MISC_FEATURE
<222> LOCATION: (22)..(22)
<223> OTHER INFORMATION: Xaa = Glu, Asp, Lys or Arg
<220> FEATURE:
<221> NAME/KEY: MISC_FEATURE
<222> LOCATION: (23)..(24)
<223> OTHER INFORMATION: optionally present
<220> FEATURE:
<221> NAME/KEY: MISC_FEATURE
<222> LOCATION: (24)..(24)
<223> OTHER INFORMATION: Xaa = Glu, Asp, Lys or Arg
<220> FEATURE:
<221> NAME/KEY: MISC_FEATURE
<222> LOCATION: (25)..(26)
<223> OTHER INFORMATION: optionally present
<220> FEATURE:
<221> NAME/KEY: MISC_FEATURE
<222> LOCATION: (26)..(26)
<223> OTHER INFORMATION: Xaa = Glu, Asp, Lys or Arg
<220> FEATURE:
<221> NAME/KEY: MISC_FEATURE
<222> LOCATION: (27)..(28)
<223> OTHER INFORMATION: optionally present
<220> FEATURE:
<221> NAME/KEY: MISC_FEATURE
<222> LOCATION: (28)..(28)
<223> OTHER INFORMATION: Xaa = Glu, Asp, Lys or Arg
<220> FEATURE:
<221> NAME/KEY: MISC_FEATURE
<222> LOCATION: (29)..(30)
<223> OTHER INFORMATION: optionally present
```

```
<220> FEATURE:
<221> NAME/KEY: MISC_FEATURE
<222> LOCATION: (30)..(30)
<223> OTHER INFORMATION: Xaa = Glu, Asp, Lys or Arg
<220> FEATURE:
<221> NAME/KEY: MISC_FEATURE
<222> LOCATION: (31)..(32)
<223> OTHER INFORMATION: optionally present
<220> FEATURE:
<221> NAME/KEY: MISC_FEATURE
<222> LOCATION: (32)..(32)
<223> OTHER INFORMATION: Xaa = Glu, Asp, Lys or Arg
<220> FEATURE:
<221> NAME/KEY: MISC_FEATURE
<222> LOCATION: (33)..(34)
<223> OTHER INFORMATION: optionally present
<220> FEATURE:
<221> NAME/KEY: MISC_FEATURE
<222> LOCATION: (34)..(34)
<223> OTHER INFORMATION: Xaa = Glu, Asp, Lys or Arg
<220> FEATURE:
<221> NAME/KEY: MISC_FEATURE
<222> LOCATION: (35)..(36)
<223> OTHER INFORMATION: optionally present
<220> FEATURE:
<221> NAME/KEY: MISC_FEATURE
<222> LOCATION: (36)..(36)
<223> OTHER INFORMATION: Xaa = Glu, Asp, Lys or Arg
<220> FEATURE:
<221> NAME/KEY: MISC_FEATURE
<222> LOCATION: (37)..(38)
<223> OTHER INFORMATION: optionally present
<220> FEATURE:
<221> NAME/KEY: MISC_FEATURE
<222> LOCATION: (38)..(38)
<223> OTHER INFORMATION: Xaa = Glu, Asp, Lys or Arg
<220> FEATURE:
<221> NAME/KEY: MISC_FEATURE
<222> LOCATION: (39)..(40)
<223> OTHER INFORMATION: optionally present
<220> FEATURE:
<221> NAME/KEY: MISC_FEATURE
<222> LOCATION: (40)..(40)
<223> OTHER INFORMATION: Xaa = Glu, Asp, Lys or Arg

<400> SEQUENCE: 61

Pro Xaa Pro Xaa Pro Xaa Pro Xaa Pro Xaa Pro Xaa Pro Xaa Pro Xaa
1               5                   10                  15

Pro Xaa Pro Xaa Pro Xaa Pro Xaa Pro Xaa Pro Xaa Pro Xaa Pro Xaa
            20                  25                  30

Pro Xaa Pro Xaa Pro Xaa Pro Xaa
            35                  40

<210> SEQ ID NO 62
<211> LENGTH: 280
<212> TYPE: PRT
<213> ORGANISM: artificial sequence
<220> FEATURE:
<223> OTHER INFORMATION: synthetic construct extended proline dipeptide
      linker
<220> FEATURE:
<221> NAME/KEY: MISC_FEATURE
<222> LOCATION: (1)..(1)
<223> OTHER INFORMATION: Xaa = Glu, Asp, Lys, or Arg
<220> FEATURE:
<221> NAME/KEY: MISC_FEATURE
<222> LOCATION: (3)..(3)
<223> OTHER INFORMATION: Xaa = Glu, Asp, Lys, or Arg
<220> FEATURE:
<221> NAME/KEY: MISC_FEATURE
<222> LOCATION: (5)..(5)
<223> OTHER INFORMATION: Xaa = Glu, Asp, Lys, or Arg
<220> FEATURE:
<221> NAME/KEY: MISC_FEATURE
<222> LOCATION: (7)..(7)
<223> OTHER INFORMATION: Xaa = Glu, Asp, Lys, or Arg
```

```
-continued

<220> FEATURE:
<221> NAME/KEY: MISC_FEATURE
<222> LOCATION: (9)..(9)
<223> OTHER INFORMATION: Xaa = Glu, Asp, Lys, or Arg
<220> FEATURE:
<221> NAME/KEY: MISC_FEATURE
<222> LOCATION: (11)..(11)
<223> OTHER INFORMATION: Xaa = Glu, Asp, Lys, or Arg
<220> FEATURE:
<221> NAME/KEY: MISC_FEATURE
<222> LOCATION: (15)..(15)
<223> OTHER INFORMATION: Xaa = Glu, Asp, Lys, or Arg
<220> FEATURE:
<221> NAME/KEY: MISC_FEATURE
<222> LOCATION: (17)..(17)
<223> OTHER INFORMATION: Xaa = Glu, Asp, Lys, or Arg
<220> FEATURE:
<221> NAME/KEY: MISC_FEATURE
<222> LOCATION: (19)..(19)
<223> OTHER INFORMATION: Xaa = Glu, Asp, Lys, or Arg
<220> FEATURE:
<221> NAME/KEY: MISC_FEATURE
<222> LOCATION: (21)..(21)
<223> OTHER INFORMATION: Xaa = Glu, Asp, Lys, or Arg
<220> FEATURE:
<221> NAME/KEY: MISC_FEATURE
<222> LOCATION: (23)..(23)
<223> OTHER INFORMATION: Xaa = Glu, Asp, Lys, or Arg
<220> FEATURE:
<221> NAME/KEY: MISC_FEATURE
<222> LOCATION: (25)..(25)
<223> OTHER INFORMATION: Xaa = Glu, Asp, Lys, or Arg
<220> FEATURE:
<221> NAME/KEY: MISC_FEATURE
<222> LOCATION: (29)..(29)
<223> OTHER INFORMATION: Xaa = Glu, Asp, Lys, or Arg
<220> FEATURE:
<221> NAME/KEY: MISC_FEATURE
<222> LOCATION: (29)..(42)
<223> OTHER INFORMATION: optionally present
<220> FEATURE:
<221> NAME/KEY: MISC_FEATURE
<222> LOCATION: (31)..(31)
<223> OTHER INFORMATION: Xaa = Glu, Asp, Lys, or Arg
<220> FEATURE:
<221> NAME/KEY: MISC_FEATURE
<222> LOCATION: (33)..(33)
<223> OTHER INFORMATION: Xaa = Glu, Asp, Lys, or Arg
<220> FEATURE:
<221> NAME/KEY: MISC_FEATURE
<222> LOCATION: (35)..(35)
<223> OTHER INFORMATION: Xaa = Glu, Asp, Lys, or Arg
<220> FEATURE:
<221> NAME/KEY: MISC_FEATURE
<222> LOCATION: (37)..(37)
<223> OTHER INFORMATION: Xaa = Glu, Asp, Lys, or Arg
<220> FEATURE:
<221> NAME/KEY: MISC_FEATURE
<222> LOCATION: (39)..(39)
<223> OTHER INFORMATION: Xaa = Glu, Asp, Lys, or Arg
<220> FEATURE:
<221> NAME/KEY: MISC_FEATURE
<222> LOCATION: (43)..(43)
<223> OTHER INFORMATION: Xaa = Glu, Asp, Lys, or Arg
<220> FEATURE:
<221> NAME/KEY: MISC_FEATURE
<222> LOCATION: (43)..(56)
<223> OTHER INFORMATION: optionally present
<220> FEATURE:
<221> NAME/KEY: MISC_FEATURE
<222> LOCATION: (45)..(45)
<223> OTHER INFORMATION: Xaa = Glu, Asp, Lys, or Arg
<220> FEATURE:
<221> NAME/KEY: MISC_FEATURE
<222> LOCATION: (47)..(47)
<223> OTHER INFORMATION: Xaa = Glu, Asp, Lys, or Arg
<220> FEATURE:
<221> NAME/KEY: MISC_FEATURE
<222> LOCATION: (49)..(49)
<223> OTHER INFORMATION: Xaa = Glu, Asp, Lys, or Arg
```

```
<220> FEATURE:
<221> NAME/KEY: MISC_FEATURE
<222> LOCATION: (51)..(51)
<223> OTHER INFORMATION: Xaa = Glu, Asp, Lys, or Arg
<220> FEATURE:
<221> NAME/KEY: MISC_FEATURE
<222> LOCATION: (53)..(53)
<223> OTHER INFORMATION: Xaa = Glu, Asp, Lys, or Arg
<220> FEATURE:
<221> NAME/KEY: MISC_FEATURE
<222> LOCATION: (57)..(57)
<223> OTHER INFORMATION: Xaa = Glu, Asp, Lys, or Arg
<220> FEATURE:
<221> NAME/KEY: MISC_FEATURE
<222> LOCATION: (57)..(70)
<223> OTHER INFORMATION: optionally present
<220> FEATURE:
<221> NAME/KEY: MISC_FEATURE
<222> LOCATION: (59)..(59)
<223> OTHER INFORMATION: Xaa = Glu, Asp, Lys, or Arg
<220> FEATURE:
<221> NAME/KEY: MISC_FEATURE
<222> LOCATION: (61)..(61)
<223> OTHER INFORMATION: Xaa = Glu, Asp, Lys, or Arg
<220> FEATURE:
<221> NAME/KEY: MISC_FEATURE
<222> LOCATION: (63)..(63)
<223> OTHER INFORMATION: Xaa = Glu, Asp, Lys, or Arg
<220> FEATURE:
<221> NAME/KEY: MISC_FEATURE
<222> LOCATION: (65)..(65)
<223> OTHER INFORMATION: Xaa = Glu, Asp, Lys, or Arg
<220> FEATURE:
<221> NAME/KEY: MISC_FEATURE
<222> LOCATION: (67)..(67)
<223> OTHER INFORMATION: Xaa = Glu, Asp, Lys, or Arg
<220> FEATURE:
<221> NAME/KEY: MISC_FEATURE
<222> LOCATION: (71)..(71)
<223> OTHER INFORMATION: Xaa = Glu, Asp, Lys, or Arg
<220> FEATURE:
<221> NAME/KEY: MISC_FEATURE
<222> LOCATION: (71)..(84)
<223> OTHER INFORMATION: optionally present
<220> FEATURE:
<221> NAME/KEY: MISC_FEATURE
<222> LOCATION: (73)..(73)
<223> OTHER INFORMATION: Xaa = Glu, Asp, Lys, or Arg
<220> FEATURE:
<221> NAME/KEY: MISC_FEATURE
<222> LOCATION: (75)..(75)
<223> OTHER INFORMATION: Xaa = Glu, Asp, Lys, or Arg
<220> FEATURE:
<221> NAME/KEY: MISC_FEATURE
<222> LOCATION: (77)..(77)
<223> OTHER INFORMATION: Xaa = Glu, Asp, Lys, or Arg
<220> FEATURE:
<221> NAME/KEY: MISC_FEATURE
<222> LOCATION: (79)..(79)
<223> OTHER INFORMATION: Xaa = Glu, Asp, Lys, or Arg
<220> FEATURE:
<221> NAME/KEY: MISC_FEATURE
<222> LOCATION: (81)..(81)
<223> OTHER INFORMATION: Xaa = Glu, Asp, Lys, or Arg
<220> FEATURE:
<221> NAME/KEY: MISC_FEATURE
<222> LOCATION: (85)..(85)
<223> OTHER INFORMATION: Xaa = Glu, Asp, Lys, or Arg
<220> FEATURE:
<221> NAME/KEY: MISC_FEATURE
<222> LOCATION: (85)..(98)
<223> OTHER INFORMATION: optionally present
<220> FEATURE:
<221> NAME/KEY: MISC_FEATURE
<222> LOCATION: (87)..(87)
<223> OTHER INFORMATION: Xaa = Glu, Asp, Lys, or Arg
<220> FEATURE:
<221> NAME/KEY: MISC_FEATURE
<222> LOCATION: (89)..(89)
<223> OTHER INFORMATION: Xaa = Glu, Asp, Lys, or Arg
```

```
<220> FEATURE:
<221> NAME/KEY: MISC_FEATURE
<222> LOCATION: (91)..(91)
<223> OTHER INFORMATION: Xaa = Glu, Asp, Lys, or Arg
<220> FEATURE:
<221> NAME/KEY: MISC_FEATURE
<222> LOCATION: (93)..(93)
<223> OTHER INFORMATION: Xaa = Glu, Asp, Lys, or Arg
<220> FEATURE:
<221> NAME/KEY: MISC_FEATURE
<222> LOCATION: (95)..(95)
<223> OTHER INFORMATION: Xaa = Glu, Asp, Lys, or Arg
<220> FEATURE:
<221> NAME/KEY: MISC_FEATURE
<222> LOCATION: (99)..(99)
<223> OTHER INFORMATION: Xaa = Glu, Asp, Lys, or Arg
<220> FEATURE:
<221> NAME/KEY: MISC_FEATURE
<222> LOCATION: (99)..(112)
<223> OTHER INFORMATION: optionally present
<220> FEATURE:
<221> NAME/KEY: MISC_FEATURE
<222> LOCATION: (101)..(101)
<223> OTHER INFORMATION: Xaa = Glu, Asp, Lys, or Arg
<220> FEATURE:
<221> NAME/KEY: MISC_FEATURE
<222> LOCATION: (103)..(103)
<223> OTHER INFORMATION: Xaa = Glu, Asp, Lys, or Arg
<220> FEATURE:
<221> NAME/KEY: MISC_FEATURE
<222> LOCATION: (105)..(105)
<223> OTHER INFORMATION: Xaa = Glu, Asp, Lys, or Arg
<220> FEATURE:
<221> NAME/KEY: MISC_FEATURE
<222> LOCATION: (107)..(107)
<223> OTHER INFORMATION: Xaa = Glu, Asp, Lys, or Arg
<220> FEATURE:
<221> NAME/KEY: MISC_FEATURE
<222> LOCATION: (109)..(109)
<223> OTHER INFORMATION: Xaa = Glu, Asp, Lys, or Arg
<220> FEATURE:
<221> NAME/KEY: MISC_FEATURE
<222> LOCATION: (113)..(113)
<223> OTHER INFORMATION: Xaa = Glu, Asp, Lys, or Arg
<220> FEATURE:
<221> NAME/KEY: MISC_FEATURE
<222> LOCATION: (113)..(126)
<223> OTHER INFORMATION: optionally present
<220> FEATURE:
<221> NAME/KEY: MISC_FEATURE
<222> LOCATION: (115)..(115)
<223> OTHER INFORMATION: Xaa = Glu, Asp, Lys, or Arg
<220> FEATURE:
<221> NAME/KEY: MISC_FEATURE
<222> LOCATION: (117)..(117)
<223> OTHER INFORMATION: Xaa = Glu, Asp, Lys, or Arg
<220> FEATURE:
<221> NAME/KEY: MISC_FEATURE
<222> LOCATION: (119)..(119)
<223> OTHER INFORMATION: Xaa = Glu, Asp, Lys, or Arg
<220> FEATURE:
<221> NAME/KEY: MISC_FEATURE
<222> LOCATION: (121)..(121)
<223> OTHER INFORMATION: Xaa = Glu, Asp, Lys, or Arg
<220> FEATURE:
<221> NAME/KEY: MISC_FEATURE
<222> LOCATION: (123)..(123)
<223> OTHER INFORMATION: Xaa = Glu, Asp, Lys, or Arg
<220> FEATURE:
<221> NAME/KEY: MISC_FEATURE
<222> LOCATION: (127)..(127)
<223> OTHER INFORMATION: Xaa = Glu, Asp, Lys, or Arg
<220> FEATURE:
<221> NAME/KEY: MISC_FEATURE
<222> LOCATION: (127)..(140)
<223> OTHER INFORMATION: optionally present
<220> FEATURE:
<221> NAME/KEY: MISC_FEATURE
<222> LOCATION: (129)..(129)
<223> OTHER INFORMATION: Xaa = Glu, Asp, Lys, or Arg
```

```
<220> FEATURE:
<221> NAME/KEY: MISC_FEATURE
<222> LOCATION: (131)..(131)
<223> OTHER INFORMATION: Xaa = Glu, Asp, Lys, or Arg
<220> FEATURE:
<221> NAME/KEY: MISC_FEATURE
<222> LOCATION: (133)..(133)
<223> OTHER INFORMATION: Xaa = Glu, Asp, Lys, or Arg
<220> FEATURE:
<221> NAME/KEY: MISC_FEATURE
<222> LOCATION: (135)..(135)
<223> OTHER INFORMATION: Xaa = Glu, Asp, Lys, or Arg
<220> FEATURE:
<221> NAME/KEY: MISC_FEATURE
<222> LOCATION: (137)..(137)
<223> OTHER INFORMATION: Xaa = Glu, Asp, Lys, or Arg
<220> FEATURE:
<221> NAME/KEY: MISC_FEATURE
<222> LOCATION: (141)..(141)
<223> OTHER INFORMATION: Xaa = Glu, Asp, Lys, or Arg
<220> FEATURE:
<221> NAME/KEY: MISC_FEATURE
<222> LOCATION: (141)..(154)
<223> OTHER INFORMATION: optionally present
<220> FEATURE:
<221> NAME/KEY: MISC_FEATURE
<222> LOCATION: (143)..(143)
<223> OTHER INFORMATION: Xaa = Glu, Asp, Lys, or Arg
<220> FEATURE:
<221> NAME/KEY: MISC_FEATURE
<222> LOCATION: (145)..(145)
<223> OTHER INFORMATION: Xaa = Glu, Asp, Lys, or Arg
<220> FEATURE:
<221> NAME/KEY: MISC_FEATURE
<222> LOCATION: (147)..(147)
<223> OTHER INFORMATION: Xaa = Glu, Asp, Lys, or Arg
<220> FEATURE:
<221> NAME/KEY: MISC_FEATURE
<222> LOCATION: (149)..(149)
<223> OTHER INFORMATION: Xaa = Glu, Asp, Lys, or Arg
<220> FEATURE:
<221> NAME/KEY: MISC_FEATURE
<222> LOCATION: (151)..(151)
<223> OTHER INFORMATION: Xaa = Glu, Asp, Lys, or Arg
<220> FEATURE:
<221> NAME/KEY: MISC_FEATURE
<222> LOCATION: (155)..(155)
<223> OTHER INFORMATION: Xaa = Glu, Asp, Lys, or Arg
<220> FEATURE:
<221> NAME/KEY: MISC_FEATURE
<222> LOCATION: (155)..(168)
<223> OTHER INFORMATION: optionally present
<220> FEATURE:
<221> NAME/KEY: MISC_FEATURE
<222> LOCATION: (157)..(157)
<223> OTHER INFORMATION: Xaa = Glu, Asp, Lys, or Arg
<220> FEATURE:
<221> NAME/KEY: MISC_FEATURE
<222> LOCATION: (159)..(159)
<223> OTHER INFORMATION: Xaa = Glu, Asp, Lys, or Arg
<220> FEATURE:
<221> NAME/KEY: MISC_FEATURE
<222> LOCATION: (161)..(161)
<223> OTHER INFORMATION: Xaa = Glu, Asp, Lys, or Arg
<220> FEATURE:
<221> NAME/KEY: MISC_FEATURE
<222> LOCATION: (163)..(163)
<223> OTHER INFORMATION: Xaa = Glu, Asp, Lys, or Arg
<220> FEATURE:
<221> NAME/KEY: MISC_FEATURE
<222> LOCATION: (165)..(165)
<223> OTHER INFORMATION: Xaa = Glu, Asp, Lys, or Arg
<220> FEATURE:
<221> NAME/KEY: MISC_FEATURE
<222> LOCATION: (169)..(169)
<223> OTHER INFORMATION: Xaa = Glu, Asp, Lys, or Arg
<220> FEATURE:
<221> NAME/KEY: MISC_FEATURE
<222> LOCATION: (169)..(182)
<223> OTHER INFORMATION: optionally present
```

```
<220> FEATURE:
<221> NAME/KEY: MISC_FEATURE
<222> LOCATION: (171)..(171)
<223> OTHER INFORMATION: Xaa = Glu, Asp, Lys, or Arg
<220> FEATURE:
<221> NAME/KEY: MISC_FEATURE
<222> LOCATION: (173)..(173)
<223> OTHER INFORMATION: Xaa = Glu, Asp, Lys, or Arg
<220> FEATURE:
<221> NAME/KEY: MISC_FEATURE
<222> LOCATION: (175)..(175)
<223> OTHER INFORMATION: Xaa = Glu, Asp, Lys, or Arg
<220> FEATURE:
<221> NAME/KEY: MISC_FEATURE
<222> LOCATION: (177)..(177)
<223> OTHER INFORMATION: Xaa = Glu, Asp, Lys, or Arg
<220> FEATURE:
<221> NAME/KEY: MISC_FEATURE
<222> LOCATION: (179)..(179)
<223> OTHER INFORMATION: Xaa = Glu, Asp, Lys, or Arg
<220> FEATURE:
<221> NAME/KEY: MISC_FEATURE
<222> LOCATION: (183)..(183)
<223> OTHER INFORMATION: Xaa = Glu, Asp, Lys, or Arg
<220> FEATURE:
<221> NAME/KEY: MISC_FEATURE
<222> LOCATION: (183)..(196)
<223> OTHER INFORMATION: optionally present
<220> FEATURE:
<221> NAME/KEY: MISC_FEATURE
<222> LOCATION: (185)..(185)
<223> OTHER INFORMATION: Xaa = Glu, Asp, Lys, or Arg
<220> FEATURE:
<221> NAME/KEY: MISC_FEATURE
<222> LOCATION: (187)..(187)
<223> OTHER INFORMATION: Xaa = Glu, Asp, Lys, or Arg
<220> FEATURE:
<221> NAME/KEY: MISC_FEATURE
<222> LOCATION: (189)..(189)
<223> OTHER INFORMATION: Xaa = Glu, Asp, Lys, or Arg
<220> FEATURE:
<221> NAME/KEY: MISC_FEATURE
<222> LOCATION: (191)..(191)
<223> OTHER INFORMATION: Xaa = Glu, Asp, Lys, or Arg
<220> FEATURE:
<221> NAME/KEY: MISC_FEATURE
<222> LOCATION: (193)..(193)
<223> OTHER INFORMATION: Xaa = Glu, Asp, Lys, or Arg
<220> FEATURE:
<221> NAME/KEY: MISC_FEATURE
<222> LOCATION: (197)..(197)
<223> OTHER INFORMATION: Xaa = Glu, Asp, Lys, or Arg
<220> FEATURE:
<221> NAME/KEY: MISC_FEATURE
<222> LOCATION: (197)..(210)
<223> OTHER INFORMATION: optionally present
<220> FEATURE:
<221> NAME/KEY: MISC_FEATURE
<222> LOCATION: (199)..(199)
<223> OTHER INFORMATION: Xaa = Glu, Asp, Lys, or Arg
<220> FEATURE:
<221> NAME/KEY: MISC_FEATURE
<222> LOCATION: (201)..(201)
<223> OTHER INFORMATION: Xaa = Glu, Asp, Lys, or Arg
<220> FEATURE:
<221> NAME/KEY: MISC_FEATURE
<222> LOCATION: (203)..(203)
<223> OTHER INFORMATION: Xaa = Glu, Asp, Lys, or Arg
<220> FEATURE:
<221> NAME/KEY: MISC_FEATURE
<222> LOCATION: (205)..(205)
<223> OTHER INFORMATION: Xaa = Glu, Asp, Lys, or Arg
<220> FEATURE:
<221> NAME/KEY: MISC_FEATURE
<222> LOCATION: (207)..(207)
<223> OTHER INFORMATION: Xaa = Glu, Asp, Lys, or Arg
<220> FEATURE:
<221> NAME/KEY: MISC_FEATURE
<222> LOCATION: (211)..(211)
<223> OTHER INFORMATION: Xaa = Glu, Asp, Lys, or Arg
```

```
<220> FEATURE:
<221> NAME/KEY: MISC_FEATURE
<222> LOCATION: (211)..(224)
<223> OTHER INFORMATION: optionally present
<220> FEATURE:
<221> NAME/KEY: MISC_FEATURE
<222> LOCATION: (213)..(213)
<223> OTHER INFORMATION: Xaa = Glu, Asp, Lys, or Arg
<220> FEATURE:
<221> NAME/KEY: MISC_FEATURE
<222> LOCATION: (215)..(215)
<223> OTHER INFORMATION: Xaa = Glu, Asp, Lys, or Arg
<220> FEATURE:
<221> NAME/KEY: MISC_FEATURE
<222> LOCATION: (217)..(217)
<223> OTHER INFORMATION: Xaa = Glu, Asp, Lys, or Arg
<220> FEATURE:
<221> NAME/KEY: MISC_FEATURE
<222> LOCATION: (219)..(219)
<223> OTHER INFORMATION: Xaa = Glu, Asp, Lys, or Arg
<220> FEATURE:
<221> NAME/KEY: MISC_FEATURE
<222> LOCATION: (221)..(221)
<223> OTHER INFORMATION: Xaa = Glu, Asp, Lys, or Arg
<220> FEATURE:
<221> NAME/KEY: MISC_FEATURE
<222> LOCATION: (225)..(225)
<223> OTHER INFORMATION: Xaa = Glu, Asp, Lys, or Arg
<220> FEATURE:
<221> NAME/KEY: MISC_FEATURE
<222> LOCATION: (225)..(238)
<223> OTHER INFORMATION: optionally present
<220> FEATURE:
<221> NAME/KEY: MISC_FEATURE
<222> LOCATION: (227)..(227)
<223> OTHER INFORMATION: Xaa = Glu, Asp, Lys, or Arg
<220> FEATURE:
<221> NAME/KEY: MISC_FEATURE
<222> LOCATION: (229)..(229)
<223> OTHER INFORMATION: Xaa = Glu, Asp, Lys, or Arg
<220> FEATURE:
<221> NAME/KEY: MISC_FEATURE
<222> LOCATION: (231)..(231)
<223> OTHER INFORMATION: Xaa = Glu, Asp, Lys, or Arg
<220> FEATURE:
<221> NAME/KEY: MISC_FEATURE
<222> LOCATION: (233)..(233)
<223> OTHER INFORMATION: Xaa = Glu, Asp, Lys, or Arg
<220> FEATURE:
<221> NAME/KEY: MISC_FEATURE
<222> LOCATION: (235)..(235)
<223> OTHER INFORMATION: Xaa = Glu, Asp, Lys, or Arg
<220> FEATURE:
<221> NAME/KEY: MISC_FEATURE
<222> LOCATION: (239)..(239)
<223> OTHER INFORMATION: Xaa = Glu, Asp, Lys, or Arg
<220> FEATURE:
<221> NAME/KEY: MISC_FEATURE
<222> LOCATION: (239)..(252)
<223> OTHER INFORMATION: optionally present
<220> FEATURE:
<221> NAME/KEY: MISC_FEATURE
<222> LOCATION: (241)..(241)
<223> OTHER INFORMATION: Xaa = Glu, Asp, Lys, or Arg
<220> FEATURE:
<221> NAME/KEY: MISC_FEATURE
<222> LOCATION: (243)..(243)
<223> OTHER INFORMATION: Xaa = Glu, Asp, Lys, or Arg
<220> FEATURE:
<221> NAME/KEY: MISC_FEATURE
<222> LOCATION: (245)..(245)
<223> OTHER INFORMATION: Xaa = Glu, Asp, Lys, or Arg
<220> FEATURE:
<221> NAME/KEY: MISC_FEATURE
<222> LOCATION: (247)..(247)
<223> OTHER INFORMATION: Xaa = Glu, Asp, Lys, or Arg
<220> FEATURE:
<221> NAME/KEY: MISC_FEATURE
<222> LOCATION: (249)..(249)
<223> OTHER INFORMATION: Xaa = Glu, Asp, Lys, or Arg
```

```
<220> FEATURE:
<221> NAME/KEY: MISC_FEATURE
<222> LOCATION: (253)..(253)
<223> OTHER INFORMATION: Xaa = Glu, Asp, Lys, or Arg
<220> FEATURE:
<221> NAME/KEY: MISC_FEATURE
<222> LOCATION: (253)..(266)
<223> OTHER INFORMATION: optionally present
<220> FEATURE:
<221> NAME/KEY: MISC_FEATURE
<222> LOCATION: (255)..(255)
<223> OTHER INFORMATION: Xaa = Glu, Asp, Lys, or Arg
<220> FEATURE:
<221> NAME/KEY: MISC_FEATURE
<222> LOCATION: (257)..(257)
<223> OTHER INFORMATION: Xaa = Glu, Asp, Lys, or Arg
<220> FEATURE:
<221> NAME/KEY: MISC_FEATURE
<222> LOCATION: (259)..(259)
<223> OTHER INFORMATION: Xaa = Glu, Asp, Lys, or Arg
<220> FEATURE:
<221> NAME/KEY: MISC_FEATURE
<222> LOCATION: (261)..(261)
<223> OTHER INFORMATION: Xaa = Glu, Asp, Lys, or Arg
<220> FEATURE:
<221> NAME/KEY: MISC_FEATURE
<222> LOCATION: (263)..(263)
<223> OTHER INFORMATION: Xaa = Glu, Asp, Lys, or Arg
<220> FEATURE:
<221> NAME/KEY: MISC_FEATURE
<222> LOCATION: (267)..(267)
<223> OTHER INFORMATION: Xaa = Glu, Asp, Lys, or Arg
<220> FEATURE:
<221> NAME/KEY: MISC_FEATURE
<222> LOCATION: (267)..(280)
<223> OTHER INFORMATION: optionally present
<220> FEATURE:
<221> NAME/KEY: MISC_FEATURE
<222> LOCATION: (269)..(269)
<223> OTHER INFORMATION: Xaa = Glu, Asp, Lys, or Arg
<220> FEATURE:
<221> NAME/KEY: MISC_FEATURE
<222> LOCATION: (271)..(271)
<223> OTHER INFORMATION: Xaa = Glu, Asp, Lys, or Arg
<220> FEATURE:
<221> NAME/KEY: MISC_FEATURE
<222> LOCATION: (273)..(273)
<223> OTHER INFORMATION: Xaa = Glu, Asp, Lys, or Arg
<220> FEATURE:
<221> NAME/KEY: MISC_FEATURE
<222> LOCATION: (275)..(275)
<223> OTHER INFORMATION: Xaa = Glu, Asp, Lys, or Arg
<220> FEATURE:
<221> NAME/KEY: MISC_FEATURE
<222> LOCATION: (277)..(277)
<223> OTHER INFORMATION: Xaa = Glu, Asp, Lys, or Arg

<400> SEQUENCE: 62

Xaa Pro Xaa Pro Xaa Pro Xaa Pro Xaa Pro Xaa Pro Gly Gly Xaa Pro
1               5                   10                  15

Xaa Pro Xaa Pro Xaa Pro Xaa Pro Xaa Pro Gly Gly Xaa Pro Xaa Pro
            20                  25                  30

Xaa Pro Xaa Pro Xaa Pro Xaa Pro Gly Gly Xaa Pro Xaa Pro Xaa Pro
        35                  40                  45

Xaa Pro Xaa Pro Xaa Pro Gly Gly Xaa Pro Xaa Pro Xaa Pro Xaa Pro
    50                  55                  60

Xaa Pro Xaa Pro Gly Gly Xaa Pro Xaa Pro Xaa Pro Xaa Pro Xaa Pro
65                  70                  75                  80

Xaa Pro Gly Gly Xaa Pro Xaa Pro Xaa Pro Xaa Pro Xaa Pro Xaa Pro
                85                  90                  95

Gly Gly Xaa Pro Xaa Pro Xaa Pro Xaa Pro Xaa Pro Xaa Pro Gly Gly
            100                 105                 110
```

```
Xaa Pro Xaa Pro Xaa Pro Xaa Pro Xaa Pro Gly Gly Xaa Pro
        115                 120                 125

Xaa Pro Xaa Pro Xaa Pro Xaa Pro Gly Gly Xaa Pro Xaa Pro
130                 135                 140

Xaa Pro Xaa Pro Xaa Pro Xaa Pro Gly Gly Xaa Pro Xaa Pro Xaa Pro
145                 150                 155                 160

Xaa Pro Xaa Pro Xaa Pro Gly Gly Xaa Pro Xaa Pro Xaa Pro Xaa Pro
            165                 170                 175

Xaa Pro Xaa Pro Gly Gly Xaa Pro Xaa Pro Xaa Pro Xaa Pro Xaa Pro
        180                 185                 190

Xaa Pro Gly Gly Xaa Pro Xaa Pro Xaa Pro Xaa Pro Xaa Pro Xaa Pro
    195                 200                 205

Gly Gly Xaa Pro Xaa Pro Xaa Pro Xaa Pro Xaa Pro Xaa Pro Gly Gly
    210                 215                 220

Xaa Pro Xaa Pro Xaa Pro Xaa Pro Xaa Pro Gly Gly Xaa Pro
225                 230                 235                 240

Xaa Pro Xaa Pro Xaa Pro Xaa Pro Gly Gly Xaa Pro Xaa Pro
            245                 250                 255

Xaa Pro Xaa Pro Xaa Pro Gly Gly Xaa Pro Xaa Pro Xaa Pro
        260                 265                 270

Xaa Pro Xaa Pro Xaa Pro Gly Gly
    275                 280

<210> SEQ ID NO 63
<211> LENGTH: 20
<212> TYPE: DNA
<213> ORGANISM: Artificial Sequence
<220> FEATURE:
<223> OTHER INFORMATION: Primer

<400> SEQUENCE: 63
ccctcatagt tagcgtaacg                                              20

<210> SEQ ID NO 64
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 64

Asn Gly Asn Asn His Thr Asp Ile Pro Asn Arg Ser Ser Tyr Thr Gly
1               5                   10                  15

Gly Ser Phe Ala
            20

<210> SEQ ID NO 65
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 65

Thr Met Thr Asn His Val Tyr Asn Ser Tyr Thr Glu Lys His Ser Ser
1               5                   10                  15

Thr His Arg Ser
            20

<210> SEQ ID NO 66
<211> LENGTH: 20
```

-continued

```
<212> TYPE: PRT
<213> ORGANISM: Artificial Sequence
<220> FEATURE:
<223> OTHER INFORMATION: Synthetic oral-surface binding peptide

<400> SEQUENCE: 66

Thr Thr Tyr His Tyr Lys Asn Ile Tyr Gln Glu Ser Tyr Gln Gln Arg
1               5                   10                  15

Asn Pro Ala Val
            20

<210> SEQ ID NO 67
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 67

Val Glu Pro Ala Thr Lys Asn Met Arg Glu Ala Arg Ser Ser Thr Gln
1               5                   10                  15

Met Arg Arg Ile
            20

<210> SEQ ID NO 68
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 68

Tyr Leu Leu Pro Lys Asp Gln Thr Thr Ala Pro Gln Val Thr Pro Ile
1               5                   10                  15

Val Gln His Lys
            20

<210> SEQ ID NO 69
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 69

Ala Ser Asn Leu Asp Ser Thr Phe Thr Ala Ile Asn Thr Pro Ala Cys
1               5                   10                  15

Cys Thr

<210> SEQ ID NO 70
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 70

Glu Phe Pro Tyr Tyr Asn Asp Asn Pro Pro Asn Pro Glu Arg His Thr
1               5                   10                  15

Leu Arg

<210> SEQ ID NO 71
<211> LENGTH: 18
<212> TYPE: PRT
<213> ORGANISM: Artificial Sequence
```

```
<220> FEATURE:
<223> OTHER INFORMATION: Synthetic oral-surface binding peptide

<400> SEQUENCE: 71

Gly Met Pro Thr Arg Tyr Tyr His Asn Thr Pro Pro His Leu Thr Pro
1               5                   10                  15

Lys Phe

<210> SEQ ID NO 72
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 72

His Lys Asn Ala Ile Gln Pro Val Asn Asp Ala Thr Thr Leu Asp Thr
1               5                   10                  15

Thr Met

<210> SEQ ID NO 73
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 73

Ala Val Val Pro Ala Asp Leu Asn Asp His Ala Asn His Leu Ser
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 74

Asp Leu Gly Thr Phe Pro Asn Arg Thr Leu Lys Met Ala Ala His
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 75

Phe Asp Gly Ile Gly Leu Gly Thr Ala Thr Arg His Gln Asn Arg
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 76

Gln Ala Ala Gln Val His Met Met Gln His Ser Arg Pro Thr Thr
1               5                   10                  15

<210> SEQ ID NO 77
<211> LENGTH: 18
```

```
<212> TYPE: PRT
<213> ORGANISM: Artificial Sequence
<220> FEATURE:
<223> OTHER INFORMATION: Synthetic oral-surface binding peptide

<400> SEQUENCE: 77

Ser Glu Ala Arg Ala Arg Thr Phe Asn Asp His Thr Thr Pro Met Pro
1               5                   10                  15

Ile Ile

<210> SEQ ID NO 78
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 78

Glu Leu Asp His Asp Ser Arg His Tyr Met Asn Gly Leu Gln Arg Lys
1               5                   10                  15

Val Thr

<210> SEQ ID NO 79
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 79

Gly Pro Gln His Val Leu Met Gln Asp Thr His Gln Gly Tyr Ala Phe
1               5                   10                  15

Asp Asn

<210> SEQ ID NO 80
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 80

Thr Thr Gly Ser Ser Ser Gln Ala Asp Thr Ser Ala Ser Met Ser Ile
1               5                   10                  15

Val Pro Ala His
            20

<210> SEQ ID NO 81
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 81

Lys Ala Pro Ile Ala Asn Met Leu Gln Pro His Ser Tyr Gln Tyr Ser
1               5                   10                  15

Val Ala

<210> SEQ ID NO 82
<211> LENGTH: 18
<212> TYPE: PRT
<213> ORGANISM: Artificial Sequence
<220> FEATURE:
<223> OTHER INFORMATION: Synthetic oral-surface binding peptide
```

-continued

<400> SEQUENCE: 82

Thr Tyr Gln Gly Val Pro Ser Trp Pro Ala Val Ile Asp Asp Ala Ile
1               5                   10                  15

Arg Arg

<210> SEQ ID NO 83
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 83

Val Asn Pro Asn Trp Val Glu Thr Gln Ala Leu His Gln Pro Pro Gly
1               5                   10                  15

Asn Thr

<210> SEQ ID NO 84
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 84

Asp His Asn Asn Arg Gln His Ala Val Glu Val Arg Glu Asn Lys Thr
1               5                   10                  15

His Thr Ala Arg
            20

<210> SEQ ID NO 85
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 85

Ile Tyr Pro Asn Glu Ser Met Ser Thr Ser Asn Val Arg Gly Pro Tyr
1               5                   10                  15

His Pro

<210> SEQ ID NO 86
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 86

His Asp Pro Asn His Leu Thr His Gln Ala Arg Thr Ile Tyr Arg Asn
1               5                   10                  15

Ala Asn His Thr
            20

<210> SEQ ID NO 87
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 87

```
Ser Asn Ala Thr Met Tyr Asn Ile Gln Ser His Ser His His Gln
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 88

Ala Asn Glu Leu Ser Thr Tyr Ala Gln Thr Asn Pro Gly Ser Gly
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 89

Asp Thr Ile His Pro Asn Lys Met Lys Ser Pro Ser Ser Pro Leu
1               5                   10                  15

<210> SEQ ID NO 90
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 90

Ala Pro Pro Thr Tyr Gln Thr Ala Ser Tyr Pro His Asn Leu Pro Ser
1               5                   10                  15

Lys Arg Lys Met
            20

<210> SEQ ID NO 91
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 91

Gln Val Pro Asp Tyr Leu Ser Pro Thr His Gln Lys Lys Ala Phe Leu
1               5                   10                  15

Glu Ile Pro Thr
            20

<210> SEQ ID NO 92
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 92

Thr Asn Asp Leu His Ala Asn Pro Phe Thr Gly Thr Tyr Ile Ala Pro
1               5                   10                  15

Asp Pro Thr Ser
            20

<210> SEQ ID NO 93
<211> LENGTH: 20
```

```
<212> TYPE: PRT
<213> ORGANISM: Artificial Sequence
<220> FEATURE:
<223> OTHER INFORMATION: Synthetic oral-surface binding peptide

<400> SEQUENCE: 93

His Lys Asn Glu Asn Ile Met Gln Tyr Asn Val Asn Asp Arg Trp His
1               5                   10                  15

Ile Thr Pro Ala
            20

<210> SEQ ID NO 94
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 94

Ile Asp Gly Pro His His Ser Pro Val His Arg Tyr His Thr Pro Ser
1               5                   10                  15

Ile Thr

<210> SEQ ID NO 95
<211> LENGTH: 15
<212> TYPE: PRT
<213> ORGANISM: Artificial Sequence
<220> FEATURE:
<223> OTHER INFORMATION: Synthetic peptide

<400> SEQUENCE: 95

Ile Pro Trp Trp Asn Ile Arg Ala Pro Leu Asn Ala Gly Gly Gly
1               5                   10                  15

<210> SEQ ID NO 96
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 96

Ala Ile Glu Tyr Gln His Ser Ala Thr Thr Pro Trp Thr Met Arg Thr
1               5                   10                  15

Arg Leu Pro Pro
            20

<210> SEQ ID NO 97
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 97

Glu Phe Tyr Pro Phe Ala Glu Val Pro Pro Glu Lys Ser Gly Ile Gly
1               5                   10                  15

Arg Gln Val Phe
            20

<210> SEQ ID NO 98
<211> LENGTH: 20
<212> TYPE: PRT
<213> ORGANISM: Artificial Sequence
<220> FEATURE:
<223> OTHER INFORMATION: Synthetic oral-surface binding peptide
```

<400> SEQUENCE: 98

Gly Val His Gln Tyr Ser Arg Pro Thr Val Pro Ser Tyr Leu Trp Thr
1               5                   10                  15
Ser Gly Gln His
            20

<210> SEQ ID NO 99
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 99

Gly Tyr Gln Pro His Tyr Val Asp His Thr Ile Gly Trp Gln Pro Met
1               5                   10                  15
Ile Arg Pro Asn
            20

<210> SEQ ID NO 100
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 100

Gln Phe Asn Gln Thr Ser His Ser Phe Met His Gly Thr Ser Gly Tyr
1               5                   10                  15
Val Pro Gly Lys
            20

<210> SEQ ID NO 101
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 101

Ser Phe Ser Trp His Arg Gly Asp Trp Glu Leu Gly His Gln Ser Lys
1               5                   10                  15
Thr Met Gly Met
            20

<210> SEQ ID NO 102
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 102

Ser Met Trp His Asp Ile Thr Lys Arg Tyr Arg Asn Pro Ser Glu Met
1               5                   10                  15
Val Ser Ala Tyr
            20

<210> SEQ ID NO 103
<211> LENGTH: 20
<212> TYPE: PRT
<213> ORGANISM: Artificial Sequence
<220> FEATURE:
<223> OTHER INFORMATION: Synthetic oral-surface binding peptide

```
<400> SEQUENCE: 103

Thr His Gly Asn Lys His Gln Ser Trp Thr Tyr Pro Ser Glu Ile Asn
1               5                   10                  15

His Lys Asn Tyr
            20

<210> SEQ ID NO 104
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 104

Trp His Glu Pro His Gln Phe Ser Gly Glu Asn Thr Asp Tyr Ser Ser
1               5                   10                  15

Ser Met Gly Thr
            20

<210> SEQ ID NO 105
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 105

Thr His Gly Asn Lys His Gln Ser Trp Thr Tyr Pro Ser Glu Ile Asn
1               5                   10                  15

His Lys Asn Tyr
            20

<210> SEQ ID NO 106
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 106

Asp Gly Tyr Lys Leu Gln Thr Ser Leu Asp Trp Gln Met Trp Asn Pro
1               5                   10                  15

<210> SEQ ID NO 107
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 107

Phe Pro Ser Lys Trp Tyr Asn His His Arg His Ile Thr Gly His Val
1               5                   10                  15

<210> SEQ ID NO 108
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 108

Gly Gly Met Gly Ala Leu Glu Ser Tyr Arg Gln Trp Asn His Leu Ala
1               5                   10                  15
```

```
<210> SEQ ID NO 109
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 109

Gly Ile Asn Lys Gly Gln Arg Pro Pro Trp Glu Ser Trp His Glu Asn
1               5                   10                  15

<210> SEQ ID NO 110
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 110

Gly Tyr Gly Gln Tyr Val Ser Gln Gln Thr Trp Ala His Ser Asn Lys
1               5                   10                  15

<210> SEQ ID NO 111
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 111

His Asp His Leu Ser Trp Trp Gly Gln Phe Asp Arg Gln Asn Leu Leu
1               5                   10                  15

<210> SEQ ID NO 112
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 112

Met Pro Gly His Gln Glu Ser Ile Lys Val Gln Asn Trp Asn Arg Val
1               5                   10                  15

<210> SEQ ID NO 113
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 113

Asn Leu His Ser Pro Trp Pro Ser His Ala Ala His Trp Ser Thr
1               5                   10                  15

<210> SEQ ID NO 114
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 114

Asn Gln Gln Met Lys Leu Val Pro Gln His Trp His Arg Ala Gln Pro
1               5                   10                  15

<210> SEQ ID NO 115
```

```
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 115

Ser Glu Lys Trp Phe Asn Pro Gly Pro Trp Pro Lys Leu Ala Thr Gln
1               5                   10                  15

<210> SEQ ID NO 116
<211> LENGTH: 19
<212> TYPE: PRT
<213> ORGANISM: artificial sequence
<220> FEATURE:
<223> OTHER INFORMATION: Synthetic construct

<400> SEQUENCE: 116

Lys Asp His Leu Ile His Asn Val His Lys Glu Phe His Ala His Ala
1               5                   10                  15

His Asn Lys

<210> SEQ ID NO 117
<211> LENGTH: 4
<212> TYPE: PRT
<213> ORGANISM: artificial sequence
<220> FEATURE:
<223> OTHER INFORMATION: Synthetic construct

<400> SEQUENCE: 117

Lys Gln Pro Asn
1

<210> SEQ ID NO 118
<211> LENGTH: 4
<212> TYPE: PRT
<213> ORGANISM: artificial sequence
<220> FEATURE:
<223> OTHER INFORMATION: Synthetic construct

<400> SEQUENCE: 118

Ser Ser Arg Pro
1

<210> SEQ ID NO 119
<211> LENGTH: 6
<212> TYPE: PRT
<213> ORGANISM: Artificial Sequence
<220> FEATURE:
<223> OTHER INFORMATION: synthetic construct

<400> SEQUENCE: 119

His His His His His His
1               5

<210> SEQ ID NO 120
<211> LENGTH: 75
<212> TYPE: PRT
<213> ORGANISM: Artificial Sequence
<220> FEATURE:
<223> OTHER INFORMATION: Synthetic peptide composition

<400> SEQUENCE: 120

Pro Gly Ser Gly Gly Gly Gly Ser Pro Tyr Ser Glu Thr Pro Asn Asp
1               5                   10                  15

Gln Lys Pro Asn Pro His Tyr Lys Val Ser Gly Thr Lys Gly Pro Glu
                20                  25                  30
```

```
Glu Ala Ala Lys Lys Glu Glu Ala Ala Lys Lys Pro Ala Tyr Ser Glu
            35                  40                  45

Thr Pro Asn Asp Gln Lys Pro Asn Pro His Tyr Lys Val Ser Gly Thr
 50                  55                  60

Lys Gly Pro Gly Gly His His His His His
 65                  70                  75
```

<210> SEQ ID NO 121
<211> LENGTH: 96
<212> TYPE: PRT
<213> ORGANISM: Artificial Sequence
<220> FEATURE:
<223> OTHER INFORMATION: Synthetic peptide composition

<400> SEQUENCE: 121

```
Pro Gly Ser Gly Gly Gly Ser Pro Tyr Ser Glu Thr Pro Asn Asp
 1               5                  10                  15

Gln Lys Pro Asn Pro His Tyr Lys Val Ser Gly Thr Lys Gly Pro Glu
            20                  25                  30

Pro Glu Pro Glu Pro Glu Pro Ile Pro Glu Pro Pro Lys Glu Ala Pro
            35                  40                  45

Val Val Ile Glu Lys Pro Lys Pro Lys Pro Lys Pro Lys Pro Lys Pro
 50                  55                  60

Pro Ala Tyr Ser Glu Thr Pro Asn Asp Gln Lys Pro Asn Pro His Tyr
 65                  70                  75                  80

Lys Val Ser Gly Thr Lys Gly Pro Gly Gly His His His His His
                85                  90                  95
```

<210> SEQ ID NO 122
<211> LENGTH: 85
<212> TYPE: PRT
<213> ORGANISM: Artificial Sequence
<220> FEATURE:
<223> OTHER INFORMATION: Synthetic peptide composition

<400> SEQUENCE: 122

```
Pro Gly Ser Gly Gly Gly Ser Pro Tyr Ser Glu Thr Pro Asn Asp
 1               5                  10                  15

Gln Lys Pro Asn Pro His Tyr Lys Val Ser Gly Thr Lys Gly Gly Gly
            20                  25                  30

Tyr Ser Glu Thr Pro Asn Asp Gln Lys Pro Asn Pro His Tyr Lys Val
            35                  40                  45

Ser Gly Thr Lys Gly Gly Gly Tyr Ser Glu Thr Pro Asn Asp Gln Lys
 50                  55                  60

Pro Asn Pro His Tyr Lys Val Ser Gly Thr Lys Gly Pro Gly Gly His
 65                  70                  75                  80

His His His His His
        85
```

<210> SEQ ID NO 123
<211> LENGTH: 135
<212> TYPE: PRT
<213> ORGANISM: Artificial Sequence
<220> FEATURE:
<223> OTHER INFORMATION: Synthetic peptide composition

<400> SEQUENCE: 123

```
Pro His Met Ala Ser Met Thr Gly Gly Gln Gln Met Gly Ser Tyr Ser
 1               5                  10                  15

Glu Thr Pro Asn Asp Gln Lys Pro Asn Pro His Tyr Lys Val Ser Gly
```

```
                     20                  25                  30
Thr Lys Gly Pro Glu Ala Ala Lys Glu Glu Ala Ala Lys Lys
        35                  40                  45

Pro Ala Tyr Ser Glu Thr Pro Asn Asp Gln Lys Pro Asn His Tyr
 50                  55                  60

Lys Val Ser Gly Thr Lys Gly Ser Gly Gly Gly Ser Gly Ser Gly
 65                  70                  75                  80

Gly Gly Gly Ser Leu Asn Ser Met Ser Asp Lys His His Gly His Gln
                 85                  90                  95

Asn Thr Ala Thr Arg Asn Gln His Gly Gly Gly Leu Asn Ser Met Ser
                100                 105                 110

Asp Lys His His Gly His Gln Asn Thr Ala Thr Arg Asn Gln His Gly
            115                 120                 125

Gly His His His His His His
        130                 135

<210> SEQ ID NO 124
<211> LENGTH: 20
<212> TYPE: PRT
<213> ORGANISM: Artificial Sequence
<220> FEATURE:
<223> OTHER INFORMATION: Synthetic binding peptide

<400> SEQUENCE: 124

Leu Asn Ser Met Ser Asp Lys His His Gly His Gln Asn Thr Ala Thr
 1               5                  10                  15

Arg Asn Gln His
            20

<210> SEQ ID NO 125
<211> LENGTH: 25
<212> TYPE: PRT
<213> ORGANISM: Artificial Sequence
<220> FEATURE:
<223> OTHER INFORMATION: Synthetic peptide-first binding element
<220> FEATURE:
<221> NAME/KEY: MISC_FEATURE
<222> LOCATION: (25)..(25)
<223> OTHER INFORMATION: site of biotin attachment

<400> SEQUENCE: 125

Ser Ser Arg Pro Asn Gly Asn Asn His Thr Asp Ile Pro Asn Arg Ser
 1               5                  10                  15

Ser Tyr Thr Gly Gly Ser Phe Ala Lys
            20                  25

<210> SEQ ID NO 126
<211> LENGTH: 25
<212> TYPE: PRT
<213> ORGANISM: Artificial Sequence
<220> FEATURE:
<223> OTHER INFORMATION: Synthetic peptide-first binding element
<220> FEATURE:
<221> NAME/KEY: MISC_FEATURE
<222> LOCATION: (25)..(25)
<223> OTHER INFORMATION: site of biotin attachment

<400> SEQUENCE: 126

Ser Ser Arg Pro Thr Met Thr Asn His Val Tyr Asn Ser Tyr Thr Glu
 1               5                  10                  15

Lys His Ser Ser Thr His Arg Ser Lys
            20                  25
```

```
<210> SEQ ID NO 127
<211> LENGTH: 25
<212> TYPE: PRT
<213> ORGANISM: Artificial Sequence
<220> FEATURE:
<223> OTHER INFORMATION: Synthetic peptide- first binding element
<220> FEATURE:
<221> NAME/KEY: MISC_FEATURE
<222> LOCATION: (25)..(25)
<223> OTHER INFORMATION: site of biotin attachment

<400> SEQUENCE: 127

Ser Ser Arg Pro Thr Thr Tyr His Tyr Lys Asn Ile Tyr Gln Glu Ser
1               5                   10                  15

Tyr Gln Gln Arg Asn Pro Ala Val Lys
            20                  25

<210> SEQ ID NO 128
<211> LENGTH: 25
<212> TYPE: PRT
<213> ORGANISM: Artificial Sequence
<220> FEATURE:
<223> OTHER INFORMATION: Synthetic peptide- first binding element
<220> FEATURE:
<221> NAME/KEY: MISC_FEATURE
<222> LOCATION: (25)..(25)
<223> OTHER INFORMATION: site of biotin attachment

<400> SEQUENCE: 128

Ser Ser Arg Pro Val Glu Pro Ala Thr Lys Asn Met Arg Glu Ala Arg
1               5                   10                  15

Ser Ser Thr Gln Met Arg Arg Ile Lys
            20                  25

<210> SEQ ID NO 129
<211> LENGTH: 25
<212> TYPE: PRT
<213> ORGANISM: Artificial Sequence
<220> FEATURE:
<223> OTHER INFORMATION: Synthetic peptide- first binding element
<220> FEATURE:
<221> NAME/KEY: MISC_FEATURE
<222> LOCATION: (25)..(25)
<223> OTHER INFORMATION: site of biotin attachment

<400> SEQUENCE: 129

Ser Ser Arg Pro Tyr Leu Leu Pro Lys Asp Gln Thr Thr Ala Pro Gln
1               5                   10                  15

Val Thr Pro Ile Val Gln His Lys Lys
            20                  25

<210> SEQ ID NO 130
<211> LENGTH: 23
<212> TYPE: PRT
<213> ORGANISM: Artificial Sequence
<220> FEATURE:
<223> OTHER INFORMATION: Synthetic peptide-first binding element
<220> FEATURE:
<221> NAME/KEY: MISC_FEATURE
<222> LOCATION: (23)..(23)
<223> OTHER INFORMATION: site of biotin attachment

<400> SEQUENCE: 130

Ser Ser Arg Pro Glu Phe Pro Tyr Tyr Asn Asp Asn Pro Pro Asn Pro
1               5                   10                  15

Glu Arg His Thr Leu Arg Lys
            20
```

```
<210> SEQ ID NO 131
<211> LENGTH: 20
<212> TYPE: PRT
<213> ORGANISM: Artificial Sequence
<220> FEATURE:
<223> OTHER INFORMATION: Synthetic peptide- first binding element
<220> FEATURE:
<221> NAME/KEY: MISC_FEATURE
<222> LOCATION: (20)..(20)
<223> OTHER INFORMATION: site of biotin attachment

<400> SEQUENCE: 131

Ser Ser Arg Pro Asp Leu Gly Thr Phe Pro Asn Arg Thr Leu Lys Met
1               5                   10                  15

Ala Ala His Lys
            20

<210> SEQ ID NO 132
<211> LENGTH: 20
<212> TYPE: PRT
<213> ORGANISM: Artificial Sequence
<220> FEATURE:
<223> OTHER INFORMATION: Synthetic peptide- first binding element
<220> FEATURE:
<221> NAME/KEY: MISC_FEATURE
<222> LOCATION: (20)..(20)
<223> OTHER INFORMATION: site of biotin attachment

<400> SEQUENCE: 132

Ser Ser Arg Pro Phe Asp Gly Ile Gly Leu Gly Thr Ala Thr Arg His
1               5                   10                  15

Gln Asn Arg Lys
            20

<210> SEQ ID NO 133
<211> LENGTH: 20
<212> TYPE: PRT
<213> ORGANISM: Artificial Sequence
<220> FEATURE:
<223> OTHER INFORMATION: Synthetic peptide-first binding element
<220> FEATURE:
<221> NAME/KEY: MISC_FEATURE
<222> LOCATION: (20)..(20)
<223> OTHER INFORMATION: site of biotin attachment

<400> SEQUENCE: 133

Ser Ser Arg Pro Gln Ala Ala Gln Val His Met Met Gln His Ser Arg
1               5                   10                  15

Pro Thr Thr Lys
            20

<210> SEQ ID NO 134
<211> LENGTH: 23
<212> TYPE: PRT
<213> ORGANISM: Artificial Sequence
<220> FEATURE:
<223> OTHER INFORMATION: Synthetic peptide-first binding element
<220> FEATURE:
<221> NAME/KEY: MISC_FEATURE
<222> LOCATION: (23)..(23)
<223> OTHER INFORMATION: site of biotin attachment

<400> SEQUENCE: 134

Ser Ser Arg Pro Ser Glu Ala Arg Ala Arg Thr Phe Asn Asp His Thr
1               5                   10                  15

Thr Pro Met Pro Ile Ile Lys
            20
```

```
<210> SEQ ID NO 135
<211> LENGTH: 23
<212> TYPE: PRT
<213> ORGANISM: Artificial Sequence
<220> FEATURE:
<223> OTHER INFORMATION: Synthetic peptide-first binding element
<220> FEATURE:
<221> NAME/KEY: MISC_FEATURE
<222> LOCATION: (23)..(23)
<223> OTHER INFORMATION: site of biotin attachment

<400> SEQUENCE: 135

Ser Ser Arg Pro Glu Leu Asp His Asp Ser Arg His Tyr Met Asn Gly
1               5                   10                  15

Leu Gln Arg Lys Val Thr Lys
            20

<210> SEQ ID NO 136
<211> LENGTH: 23
<212> TYPE: PRT
<213> ORGANISM: Artificial Sequence
<220> FEATURE:
<223> OTHER INFORMATION: Synthetic peptide-first binding element
<220> FEATURE:
<221> NAME/KEY: MISC_FEATURE
<222> LOCATION: (23)..(23)
<223> OTHER INFORMATION: site of biotin attachment

<400> SEQUENCE: 136

Ser Ser Arg Pro Gly Pro Gln His Val Leu Met Gln Asp Thr His Gln
1               5                   10                  15

Gly Tyr Ala Phe Asp Asn Lys
            20

<210> SEQ ID NO 137
<211> LENGTH: 25
<212> TYPE: PRT
<213> ORGANISM: Artificial Sequence
<220> FEATURE:
<223> OTHER INFORMATION: Synthetic peptide-first binding element
<220> FEATURE:
<221> NAME/KEY: MISC_FEATURE
<222> LOCATION: (25)..(25)
<223> OTHER INFORMATION: site of biotin attachment

<400> SEQUENCE: 137

Ser Ser Arg Pro Thr Thr Gly Ser Ser Ser Gln Ala Asp Thr Ser Ala
1               5                   10                  15

Ser Met Ser Ile Val Pro Ala His Lys
            20                  25

<210> SEQ ID NO 138
<211> LENGTH: 23
<212> TYPE: PRT
<213> ORGANISM: Artificial Sequence
<220> FEATURE:
<223> OTHER INFORMATION: Synthetic peptide-first binding element
<220> FEATURE:
<221> NAME/KEY: MISC_FEATURE
<222> LOCATION: (23)..(23)
<223> OTHER INFORMATION: site of biotin attachment

<400> SEQUENCE: 138

Ser Ser Arg Pro Thr Tyr Gln Gly Val Pro Ser Trp Pro Ala Val Ile
1               5                   10                  15

Asp Asp Ala Ile Arg Arg Lys
            20
```

```
<210> SEQ ID NO 139
<211> LENGTH: 23
<212> TYPE: PRT
<213> ORGANISM: Artificial Sequence
<220> FEATURE:
<223> OTHER INFORMATION: Synthetic peptide-first binding element
<220> FEATURE:
<221> NAME/KEY: MISC_FEATURE
<222> LOCATION: (23)..(23)
<223> OTHER INFORMATION: site of biotin attachment

<400> SEQUENCE: 139

Ser Ser Arg Pro Val Asn Pro Asn Trp Val Glu Thr Gln Ala Leu His
1               5                   10                  15

Gln Pro Pro Gly Asn Thr Lys
            20

<210> SEQ ID NO 140
<211> LENGTH: 23
<212> TYPE: PRT
<213> ORGANISM: Artificial Sequence
<220> FEATURE:
<223> OTHER INFORMATION: Synthetic peptide-first binding element
<220> FEATURE:
<221> NAME/KEY: MISC_FEATURE
<222> LOCATION: (23)..(23)
<223> OTHER INFORMATION: site of biotin attachment

<400> SEQUENCE: 140

Ser Ser Arg Pro Ile Tyr Pro Asn Glu Ser Met Ser Thr Ser Asn Val
1               5                   10                  15

Arg Gly Pro Tyr His Pro Lys
            20

<210> SEQ ID NO 141
<211> LENGTH: 25
<212> TYPE: PRT
<213> ORGANISM: Artificial Sequence
<220> FEATURE:
<223> OTHER INFORMATION: Synthetic peptide-first binding element
<220> FEATURE:
<221> NAME/KEY: MISC_FEATURE
<222> LOCATION: (25)..(25)
<223> OTHER INFORMATION: site of biotin attachment

<400> SEQUENCE: 141

Ser Ser Arg Pro His Asp Pro Asn His Leu Thr His Gln Ala Arg Thr
1               5                   10                  15

Ile Tyr Arg Asn Ala Asn His Thr Lys
            20                  25

<210> SEQ ID NO 142
<211> LENGTH: 25
<212> TYPE: PRT
<213> ORGANISM: Artificial Sequence
<220> FEATURE:
<223> OTHER INFORMATION: Synthetic peptide-first binding element
<220> FEATURE:
<221> NAME/KEY: MISC_FEATURE
<222> LOCATION: (25)..(25)
<223> OTHER INFORMATION: site of biotin attachment

<400> SEQUENCE: 142

Ser Ser Arg Pro Ala Pro Pro Thr Tyr Gln Thr Ala Ser Tyr Pro His
1               5                   10                  15

Asn Leu Pro Ser Lys Arg Lys Met Lys
            20                  25
```

```
<210> SEQ ID NO 143
<211> LENGTH: 25
<212> TYPE: PRT
<213> ORGANISM: Artificial Sequence
<220> FEATURE:
<223> OTHER INFORMATION: Synthetic peptide-first binding element
<220> FEATURE:
<221> NAME/KEY: MISC_FEATURE
<222> LOCATION: (25)..(25)
<223> OTHER INFORMATION: site of biotin attachment

<400> SEQUENCE: 143

Ser Ser Arg Pro Gln Val Pro Asp Tyr Leu Ser Pro Thr His Gln Lys
1               5                   10                  15

Lys Ala Phe Leu Glu Ile Pro Thr Lys
            20                  25

<210> SEQ ID NO 144
<211> LENGTH: 25
<212> TYPE: PRT
<213> ORGANISM: Artificial Sequence
<220> FEATURE:
<223> OTHER INFORMATION: Synthetic peptide-first binding element
<220> FEATURE:
<221> NAME/KEY: MISC_FEATURE
<222> LOCATION: (25)..(25)
<223> OTHER INFORMATION: site of biotin attachment

<400> SEQUENCE: 144

Ser Ser Arg Pro His Lys Asn Glu Asn Ile Met Gln Tyr Asn Val Asn
1               5                   10                  15

Asp Arg Trp His Ile Thr Pro Ala Lys
            20                  25

<210> SEQ ID NO 145
<211> LENGTH: 115
<212> TYPE: PRT
<213> ORGANISM: Artificial Sequence
<220> FEATURE:
<223> OTHER INFORMATION: Synthetic peptide composition

<400> SEQUENCE: 145

Pro His Ser Ser Arg Pro Thr Thr Tyr His Tyr Lys Asn Ile Tyr Gln
1               5                   10                  15

Glu Ser Tyr Gln Gln Arg Asn Pro Ala Val Gly Pro Glu Pro Glu Pro
            20                  25                  30

Glu Pro Glu Pro Ile Pro Glu Pro Pro Lys Glu Ala Pro Val Val Ile
        35                  40                  45

Glu Lys Pro Lys Pro Lys Pro Lys Pro Lys Pro Lys Pro Pro Ala Ser
    50                  55                  60

Ser Arg Pro Thr Thr Tyr His Tyr Lys Asn Ile Tyr Gln Glu Ser Tyr
65                  70                  75                  80

Gln Gln Arg Asn Pro Ala Val Gly Ser Ser Gly Pro Gly Ser Pro Lys
                85                  90                  95

Gln Pro Asn Lys Gln Pro Asn Lys Gln Pro Asn Lys Gln Pro Asn Lys
            100                 105                 110

Gln Pro Asn
        115

<210> SEQ ID NO 146
<211> LENGTH: 131
<212> TYPE: PRT
<213> ORGANISM: Artificial Sequence
<220> FEATURE:
<223> OTHER INFORMATION: Synthetic peptide composition
```

<400> SEQUENCE: 146

Pro His Ser Ser Arg Pro Thr Thr Tyr His Tyr Lys Asn Ile Tyr Gln
1               5                   10                  15

Glu Ser Tyr Gln Gln Arg Asn Pro Ala Val Gly Pro Glu Pro Glu Pro
            20                  25                  30

Glu Pro Glu Pro Ile Pro Glu Pro Pro Lys Glu Ala Pro Val Val Ile
        35                  40                  45

Glu Lys Pro Lys Pro Lys Pro Lys Pro Lys Pro Lys Pro Pro Ala Ser
    50                  55                  60

Ser Arg Pro Thr Thr Tyr His Tyr Lys Asn Ile Tyr Gln Glu Ser Tyr
65                  70                  75                  80

Gln Gln Arg Asn Pro Ala Val Gly Ser Ser Gly Pro Gly Ser Pro Lys
                85                  90                  95

Gln Pro Asn Lys Gln Pro Asn Lys Gln Pro Asn Lys Gln Pro Asn Lys
            100                 105                 110

Gln Pro Asn Lys Gln Pro Asn Lys Gln Pro Asn Lys Gln Pro Asn Lys
            115                 120                 125

Gln Pro Asn
    130

<210> SEQ ID NO 147
<211> LENGTH: 148
<212> TYPE: PRT
<213> ORGANISM: Artificial Sequence
<220> FEATURE:
<223> OTHER INFORMATION: Synthetic peptide composition

<400> SEQUENCE: 147

Pro His Ser Ser Arg Pro Thr Thr Tyr His Tyr Lys Asn Ile Tyr Gln
1               5                   10                  15

Glu Ser Tyr Gln Gln Arg Asn Pro Ala Val Gly Pro Glu Pro Glu Pro
            20                  25                  30

Glu Pro Glu Pro Ile Pro Glu Pro Pro Lys Glu Ala Pro Val Val Ile
        35                  40                  45

Glu Lys Pro Lys Pro Lys Pro Lys Pro Lys Pro Lys Pro Pro Ala Ser
    50                  55                  60

Ser Arg Pro Thr Thr Tyr His Tyr Lys Asn Ile Tyr Gln Glu Ser Tyr
65                  70                  75                  80

Gln Gln Arg Asn Pro Ala Val Gly Ser Ser Gly Pro Gly Ser Pro Lys
                85                  90                  95

Gln Pro Asn Lys Gln Pro Asn Lys Gln Pro Asn Lys Gln Pro Asn Lys
            100                 105                 110

Gln Pro Asn Lys Gln Pro Asn Lys Gln Pro Asn Lys Gln Pro Asn Pro
            115                 120                 125

Lys Gln Pro Asn Lys Gln Pro Asn Lys Gln Pro Asn Lys Gln Pro Asn
    130                 135                 140

Lys Gln Pro Asn
145

<210> SEQ ID NO 148
<211> LENGTH: 105
<212> TYPE: PRT
<213> ORGANISM: Artificial Sequence
<220> FEATURE:
<223> OTHER INFORMATION: Synthetic peptide composition

<400> SEQUENCE: 148

Pro His Ser Ser Arg Pro Thr Thr Tyr His Tyr Lys Asn Ile Tyr Gln
1               5                   10                  15

Glu Ser Tyr Gln Gln Arg Asn Pro Ala Val Gly Pro Glu Pro Glu Pro
            20                  25                  30

Glu Pro Glu Pro Ile Pro Glu Pro Pro Lys Glu Ala Pro Val Val Ile
        35                  40                  45

Glu Lys Pro Lys Pro Lys Pro Lys Pro Lys Pro Pro Ala Ser
    50                  55                  60

Ser Arg Pro Thr Thr Tyr His Tyr Lys Asn Ile Tyr Gln Glu Ser Tyr
65                  70                  75                  80

Gln Gln Arg Asn Pro Ala Val Gly Ser Ser Gly Pro Gly Ser Pro Gly
                85                  90                  95

Lys Gly Lys Gly Lys Gly Lys Gly Lys
            100                 105

<210> SEQ ID NO 149
<211> LENGTH: 113
<212> TYPE: PRT
<213> ORGANISM: Artificial Sequence
<220> FEATURE:
<223> OTHER INFORMATION: Synthetic peptide composition

<400> SEQUENCE: 149

Pro His Ser Ser Arg Pro Thr Thr Tyr His Tyr Lys Asn Ile Tyr Gln
1               5                   10                  15

Glu Ser Tyr Gln Gln Arg Asn Pro Ala Val Gly Pro Glu Pro Glu Pro
            20                  25                  30

Glu Pro Glu Pro Ile Pro Glu Pro Pro Lys Glu Ala Pro Val Val Ile
        35                  40                  45

Glu Lys Pro Lys Pro Lys Pro Lys Pro Lys Pro Pro Ala Ser
    50                  55                  60

Ser Arg Pro Thr Thr Tyr His Tyr Lys Asn Ile Tyr Gln Glu Ser Tyr
65                  70                  75                  80

Gln Gln Arg Asn Pro Ala Val Gly Ser Ser Gly Pro Gly Ser Pro Gly
                85                  90                  95

Lys Gly Lys Gly Lys Gly Lys Gly Lys Gly Lys Gly Lys Gly Lys Gly
            100                 105                 110

Lys

<210> SEQ ID NO 150
<211> LENGTH: 121
<212> TYPE: PRT
<213> ORGANISM: Artificial Sequence
<220> FEATURE:
<223> OTHER INFORMATION: Synthetic peptide composition

<400> SEQUENCE: 150

Pro His Ser Ser Arg Pro Thr Thr Tyr His Tyr Lys Asn Ile Tyr Gln
1               5                   10                  15

Glu Ser Tyr Gln Gln Arg Asn Pro Ala Val Gly Pro Glu Pro Glu Pro
            20                  25                  30

Glu Pro Glu Pro Ile Pro Glu Pro Pro Lys Glu Ala Pro Val Val Ile
        35                  40                  45

Glu Lys Pro Lys Pro Lys Pro Lys Pro Lys Pro Pro Ala Ser
    50                  55                  60

Ser Arg Pro Thr Thr Tyr His Tyr Lys Asn Ile Tyr Gln Glu Ser Tyr
65                  70                  75                  80

Gln Gln Arg Asn Pro Ala Val Gly Ser Ser Gly Pro Gly Ser Pro Gly

```
                    85                  90                  95
Lys Gly Lys Gly Lys Gly Lys Gly Lys Gly Lys Gly Lys Gly Lys Gly
                100                 105                 110
Lys Gly Lys Gly Lys Gly Lys Gly Lys
        115                 120

<210> SEQ ID NO 151
<211> LENGTH: 101
<212> TYPE: PRT
<213> ORGANISM: Artificial Sequence
<220> FEATURE:
<223> OTHER INFORMATION: Synthetic peptide composition

<400> SEQUENCE: 151

Pro His Ser Ser Arg Pro Thr Thr Tyr His Tyr Lys Asn Ile Tyr Gln
1               5                   10                  15

Glu Ser Tyr Gln Gln Arg Asn Pro Ala Val Gly Pro Glu Pro Glu Pro
            20                  25                  30

Glu Pro Glu Pro Ile Pro Glu Pro Lys Glu Ala Pro Val Val Ile
        35                  40                  45

Glu Lys Pro Lys Pro Lys Pro Lys Pro Lys Pro Lys Pro Pro Ala Ser
50                  55                  60

Ser Arg Pro Thr Thr Tyr His Tyr Lys Asn Ile Tyr Gln Glu Ser Tyr
65                  70                  75                  80

Gln Gln Arg Asn Pro Ala Val Gly Ser Ser Gly Pro Gly Ser Pro His
            85                  90                  95

His His His His His
            100

<210> SEQ ID NO 152
<211> LENGTH: 20
<212> TYPE: PRT
<213> ORGANISM: Artificial Sequence
<220> FEATURE:
<223> OTHER INFORMATION: Synthetic peptide-second binding element

<400> SEQUENCE: 152

Lys Gln Pro Asn Lys Gln Pro Asn Lys Gln Pro Asn Lys Gln Pro Asn
1               5                   10                  15

Lys Gln Pro Asn
            20

<210> SEQ ID NO 153
<211> LENGTH: 36
<212> TYPE: PRT
<213> ORGANISM: Artificial Sequence
<220> FEATURE:
<223> OTHER INFORMATION: Synthetic peptide-second binding element

<400> SEQUENCE: 153

Lys Gln Pro Asn Lys Gln Pro Asn Lys Gln Pro Asn Lys Gln Pro Asn
1               5                   10                  15

Lys Gln Pro Asn Lys Gln Pro Asn Lys Gln Pro Asn Lys Gln Pro Asn
            20                  25                  30

Lys Gln Pro Asn
        35

<210> SEQ ID NO 154
<211> LENGTH: 52
<212> TYPE: PRT
<213> ORGANISM: Artificial Sequence
<220> FEATURE:
```

-continued

<223> OTHER INFORMATION: Synthetic peptide-second binding element

<400> SEQUENCE: 154

Lys Gln Pro Asn Lys Gln Pro Asn Lys Gln Pro Asn Lys Gln Pro Asn
1               5                   10                  15

Lys Gln Pro Asn Lys Gln Pro Asn Lys Gln Pro Asn Lys Gln Pro Asn
            20                  25                  30

Lys Gln Pro Asn Lys Gln Pro Asn Lys Gln Pro Asn Lys Gln Pro Asn
        35                  40                  45

Lys Gln Pro Asn
    50

<210> SEQ ID NO 155
<211> LENGTH: 10
<212> TYPE: PRT
<213> ORGANISM: Artificial Sequence
<220> FEATURE:
<223> OTHER INFORMATION: Synthetic peptide-second binding element

<400> SEQUENCE: 155

Gly Lys Gly Lys Gly Lys Gly Lys Gly Lys
1               5                   10

<210> SEQ ID NO 156
<211> LENGTH: 18
<212> TYPE: PRT
<213> ORGANISM: Artificial Sequence
<220> FEATURE:
<223> OTHER INFORMATION: Synthetic peptide-second binding element

<400> SEQUENCE: 156

Gly Lys Gly Lys Gly Lys Gly Lys Gly Lys Gly Lys Gly Lys Gly Lys
1               5                   10                  15

Gly Lys

<210> SEQ ID NO 157
<211> LENGTH: 26
<212> TYPE: PRT
<213> ORGANISM: Artificial Sequence
<220> FEATURE:
<223> OTHER INFORMATION: Synthetic peptide-second binding element

<400> SEQUENCE: 157

Gly Lys Gly Lys Gly Lys Gly Lys Gly Lys Gly Lys Gly Lys Gly Lys
1               5                   10                  15

Gly Lys Gly Lys Gly Lys Gly Lys Gly Lys
            20                  25

<210> SEQ ID NO 158
<211> LENGTH: 8
<212> TYPE: PRT
<213> ORGANISM: Artificial sequence
<220> FEATURE:
<223> OTHER INFORMATION: Synthetic peptide linker

<400> SEQUENCE: 158

Gly Ser Ser Gly Pro Gly Ser Pro
1               5

<210> SEQ ID NO 159
<211> LENGTH: 5214
<212> TYPE: DNA
<213> ORGANISM: Artificial sequence
<220> FEATURE:
<223> OTHER INFORMATION: Vector

```
<400> SEQUENCE: 159
tacctgcctg  dacagcatgg  cctgcaacgc  gggcatcccg  atgccgccgg  aagcgagaag    60
aatcataatg  gggaaggcca  tccagcctcg  cgtcgcgaac  gccagcaaga  cgtagcccag   120
cgcgtcggcc  gccatgccgg  cgataatggc  ctgcttctcg  ccgaaacgtt  tggtggcggg   180
accagtgacg  aaggcttgag  cgagggcgtg  caagattccg  aataccgcaa  gcgacaggcc   240
gatcatcgtc  gcgctccagc  gaaagcggtc  ctcgccgaaa  atgacccaga  gcgctgccgg   300
cacctgtcct  acgagttgca  tgataaagaa  gacagtcata  agtgcggcga  cgatagtcat   360
gccccgcgcc  accggaagg   agctgactgg  gttgaaggct  ctcaagggca  tcggtcgatc   420
gacgctctcc  cttatgcgac  tcctgcatta  ggaagcagcc  cagtagtagg  ttgaggccgt   480
tgagcaccgc  cgccgcaagg  aatggtgcat  gcaaggagat  ggcgcccaac  agtccccgg    540
ccacggggcc  tgccaccata  cccacgccga  acaagcgct   catgagcccg  aagtggcgag   600
cccgatcttc  cccatcggtg  atgtcggcga  taggcgcc    agcaaccgca  cctgtggcgc   660
cggtgatgcc  ggccacgatg  cgtccggcgt  agaggatcga  gatctcgatc  ccgcgaaatt   720
aatacgactc  actataggga  gaccacaacg  gtttccctct  agaaataatt  ttgtttaact   780
ttaagaagga  gatatacata  tgcacactcc  agaacatatc  accgcagtag  tacagcgttt   840
tgtggcagct  ctgaacgcgg  gcgagctgga  aggtattgtg  gcgctgttcg  cggaagaagc   900
caccgtggaa  gaaccggtgg  gttctgaacc  gcgttccggc  accgcagcct  gccgtgaatt   960
ttacgcaaac  agcctgaagc  tgccgctggc  ggttgaactg  acccaagaat  gtcgtgcggt  1020
ggctaacgaa  gccgctttcg  cgttcaccgt  gtccttcgaa  taccagggtc  gtaagaccgt  1080
tgtgcgcca   tgcgaacact  ttcgtttcaa  cggcgcaggc  aaagtggttt  ccatccgcgc  1140
actgttcggt  gaaaagaaca  tccatgcttg  tcagggatcc  gaccctggta  tcccgtggtg  1200
gaacattcgc  gcacctctga  atgctggtgc  tggtattccg  tggtggaaca  tccgtgctcc  1260
tctgaacgcg  ggtggctccg  gtccgggctc  cggtggcaac  acgagccaac  tgagcaccgg  1320
tggtggcaac  acttcccagc  tgtccaccgg  cggtccgaaa  aagtaataag  gcgcgccgac  1380
ccagctttct  tgtacaaagt  ggttgattcg  aggctgctaa  caaagcccga  aggaagctg   1440
agttggctgc  tgccaccgct  gagcaataac  tagcataacc  ccttgggcc   tctaaacggg  1500
tcttgagggg  ttttttgctg  aaaggaggaa  ctatatccgg  atatccacag  gacgggtgtg  1560
gtcgccatga  tcgcgtagtc  gatagtggct  ccaagtagcg  aagcgagcag  gactgggcgg  1620
cggccaaagc  ggtcggacag  tgctccgaga  acgggtgcgc  atagaaattg  catcaacgca  1680
tatagcgcta  gcagcacgcc  atagtgactg  gcgatgctgt  cggaatggac  gatatcccgc  1740
aagaggcccg  gcagtaccgg  cataaccaag  cctatgccta  cagcatccag  ggtgacggtg  1800
ccgaggatga  cgatgagcgc  attgttagat  tcatacacg   gtgcctgact  gcgttagcaa  1860
tttaactgtg  ataaactacc  gcattaaagc  ttatcgatga  taagctgtca  aacatgagaa  1920
ttcttgaaga  cgaaagggcc  tcgtgatacg  cctatttta   taggttaatg  tcatgataat  1980
aatggtttct  tagacgtcag  gtggcacttt  tcggggaaat  gtgcgcggaa  ccctatttg   2040
tttattttc   taaatacatt  caaatatgta  tccgctcatg  agacaataac  cctgataaat  2100
gcttcaataa  tattgaaaaa  ggaagagtat  gagtattcaa  catttccgtg  tcgcccttat  2160
tccctttttt  gcggcatttt  gccttcctgt  ttttgctcac  ccagaaacgc  tggtgaaagt  2220
aaaagatgct  gaagatcagt  tgggtgcacg  agtgggttac  atcgaactgg  atctcaacag  2280
cggtaagatc  cttgagagtt  ttcgccccga  agaacgtttt  ccaatgatga  gcacttttaa  2340
```

```
agttctgcta tgtggcgcgg tattatcccg tgttgacgcc gggcaagagc aactcggtcg    2400
ccgcatacac tattctcaga atgacttggt tgagtactca ccagtcacag aaaagcatct    2460
tacggatggc atgacagtaa agaaattatg cagtgctgcc ataaccatga gtgataacac    2520
tgcggccaac ttacttctga caacgatcgg aggaccgaag gagctaaccg cttttttgca    2580
caacatgggg gatcatgtaa ctcgccttga tcgttgggaa ccggagctga atgaagccat    2640
accaaacgac gagcgtgaca ccacgatgcc tgcagcaatg gcaacaacgt tgcgcaaact    2700
attaactggc gaactactta ctctagcttc ccggcaacaa ttaatagact ggatggaggc    2760
ggataaagtt gcaggaccac ttctgcgctc ggcccttccg gctggctggt ttattgctga    2820
taaatctgga gccggtgagc gtgggtctcg cggtatcatt gcagcactgg ggccagatgg    2880
taagccctcc cgtatcgtag ttatctacac gacgggagt caggcaacta tggatgaacg    2940
aaatagacag atcgctgaga taggtgcctc actgattaag cattggtaac tgtcagacca    3000
agtttactca tatatacttt agattgattt aaaacttcat ttttaattta aaaggatcta    3060
ggtgaagatc cttttttgata atctcatgac caaaatccct taacgtgagt tttcgttcca    3120
ctgagcgtca gaccccgtag aaaagatcaa aggatcttct tgagatcctt ttttctgcg    3180 cgtaatctgc tgcttgcaaa caaaaaaacc accgctacca gcggtggttt gtttgccgga    3240
tcaagagcta ccaactcttt ttccgaaggt aactggcttc agcagagcgc agataccaaa    3300
tactgtcctt ctagtgtagc cgtagttagg ccaccacttc aagaactctg tagcaccgcc    3360
tacatacctc gctctgctaa tcctgttacc agtggctgct gccagtggcg ataagtcgtg    3420
tcttaccggg ttggactcaa gacgatagtt accggataag gcgcagcggt cgggctgaac    3480
ggggggttcg tgcacacagc ccagcttgga gcgaacgacc tacaccgaac tgagatacct    3540
acagcgtgag ctatgagaaa gcgccacgct tcccgaaggg agaaaggcgg acaggtatcc    3600
ggtaagcggc agggtcggaa caggagagcg cacgagggag cttccagggg gaaacgcctg    3660
gtatctttat agtcctgtcg ggtttcgcca cctctgactt gagcgtcgat ttttgtgatg    3720
ctcgtcaggg gggcggagcc tatggaaaaa cgccagcaac gcggcctttt tacggttcct    3780
ggccttttgc tggccttttg ctcacatgtt ctttcctgcg ttatcccctg attctgtgga    3840
taaccgtatt accgcctttg agtgagctga taccgctcgc cgcagccgaa cgaccgagcg    3900
cagcgagtca gtgagcgagg aagcggaaga gcgcctgatg cggtattttc tccttacgca    3960
tctgtgcggt atttcacacc gcatatatgg tgcactctca gtacaatctg ctctgatgcc    4020
gcatagttaa gccagtatac actccgctat cgctacgtga ctgggtcatg gctgcgcccc    4080
gacacccgcc aacacccgct gacgcgccct gacgggcttg tctgctcccg gcatccgctt    4140
acagacaagc tgtgaccgtc tccgggagct gcatgtgtca gaggttttca ccgtcatcac    4200
cgaaacgcgc gaggcagctg cggtaaagct catcagcgtg gtcgtgaagc gattcacaga    4260
tgtctgcctg ttcatccgcg tccagctcgt tgagtttctc cagaagcgtt aatgtctggc    4320
ttctgataaa gcgggccatg ttaagggcgg ttttttcctg tttggtcact gatgcctccg    4380
tgtaaggggg atttctgttc atgggggtaa tgataccgat gaaacgagag aggatgctca    4440
cgatacgggt tactgatgat gaacatgccc ggttactgga acgttgtgag ggtaaacaac    4500
tggcggtatg gatgcggcgg gaccagagaa aaatcactca gggtcaatgc cagcgcttcg    4560
ttaatacaga tgtaggtgtt ccacagggta gccagcagca tcctgcgatg cagatccgga    4620
acataatggt gcagggcgct gacttccgcg tttccagact ttacgaaaca cggaaaccga    4680
agaccattca tgttgttgct caggtcgcag acgttttgca gcagcagtcg cttcacgttc    4740
```

```
gctcgcgtat cggtgattca ttctgctaac cagtaaggca accccgccag cctagccggg    4800
tcctcaacga caggagcacg atcatgcgca cccgtggcca ggacccaacg ctgcccgaga    4860
tgcgccgcgt gcggctgctg gagatggcgg acgcgatgga tatgttctgc caagggttgg    4920
tttgcgcatt cacagttctc cgcaagaatt gattggctcc aattcttgga gtggtgaatc    4980
cgttagcgag gtgccgccgg cttccattca ggtcgaggtg gcccggctcc atgcaccgcg    5040
acgcaacgcg gggaggcaga caaggtatag ggcggcgcct acaatccatg ccaacccgtt    5100
ccatgtgctc gccgaggcgg cataaatcgc cgtgacgatc agcggtccag tgatcgaagt    5160
taggctggta agagccgcga gcgatccttg aagctgtccc tgatggtcgt catc          5214
```

<210> SEQ ID NO 160
<211> LENGTH: 8
<212> TYPE: PRT
<213> ORGANISM: artificial sequence
<220> FEATURE:
<223> OTHER INFORMATION: synthetic construct

<400> SEQUENCE: 160

Gly Ser Ser Gly Pro Gly Ser Ser
1               5

<210> SEQ ID NO 161
<211> LENGTH: 21
<212> TYPE: PRT
<213> ORGANISM: artificial sequence
<220> FEATURE:
<223> OTHER INFORMATION: synthetic construct
<220> FEATURE:
<221> NAME/KEY: MISC_FEATURE
<222> LOCATION: (21)..(21)
<223> OTHER INFORMATION: site of biotin attachment

<400> SEQUENCE: 161

Thr Thr Tyr His Tyr Lys Asn Ile Tyr Gln Glu Ser Tyr Gln Gln Arg
1               5                   10                  15

Asn Pro Ala Val Lys
            20

<210> SEQ ID NO 162
<211> LENGTH: 26
<212> TYPE: PRT
<213> ORGANISM: artificial sequence
<220> FEATURE:
<223> OTHER INFORMATION: synthetic construct

<400> SEQUENCE: 162

Thr Thr Tyr His Tyr Lys Asn Ile Tyr Gln Glu Ser Tyr Gln Gln Arg
1               5                   10                  15

Asn Pro Ala Val His His His His His His
            20                  25

<210> SEQ ID NO 163
<211> LENGTH: 74
<212> TYPE: PRT
<213> ORGANISM: artificial sequence
<220> FEATURE:
<223> OTHER INFORMATION: synthetic construct

<400> SEQUENCE: 163

Pro Ser Ser Ser Arg Pro Thr Thr Tyr His Tyr Lys Asn Ile Tyr Gln
1               5                   10                  15

Glu Ser Tyr Gln Gln Arg Asn Pro Ala Val Gly Pro Glu Glu Ala Ala

```
                  20                  25                  30
Lys Lys Glu Glu Ala Ala Lys Lys Pro Ala Ser Ser Arg Pro Thr Thr
            35                  40                  45
Tyr His Tyr Lys Asn Ile Tyr Gln Glu Ser Tyr Gln Gln Arg Asn Pro
        50                  55                  60
Ala Val Gly Pro His His His His His
65                  70

<210> SEQ ID NO 164
<211> LENGTH: 66
<212> TYPE: PRT
<213> ORGANISM: artificial sequence
<220> FEATURE:
<223> OTHER INFORMATION: synthetic construct

<400> SEQUENCE: 164

Pro Ser Ser Ser Arg Pro Thr Thr Tyr His Tyr Lys Asn Ile Tyr Gln
1               5                   10                  15
Glu Ser Tyr Gln Gln Arg Asn Pro Ala Val Gly Pro Glu Glu Ala Ala
                20                  25                  30
Lys Lys Glu Glu Ala Ala Lys Lys Pro Ala Ser Ser Arg Pro Thr Thr
            35                  40                  45
Tyr His Tyr Lys Asn Ile Tyr Gln Glu Ser Tyr Gln Gln Arg Asn Pro
        50                  55                  60
Ala Val
65

<210> SEQ ID NO 165
<211> LENGTH: 8
<212> TYPE: PRT
<213> ORGANISM: artificial sequence
<220> FEATURE:
<223> OTHER INFORMATION: synthetic construct

<400> SEQUENCE: 165

Gly Pro His His His His His His
1               5

<210> SEQ ID NO 166
<211> LENGTH: 117
<212> TYPE: PRT
<213> ORGANISM: artificial sequence
<220> FEATURE:
<223> OTHER INFORMATION: synthetic construct

<400> SEQUENCE: 166

Pro Ser Ser Arg Pro Thr Thr Tyr His Tyr Lys Asn Ile Tyr Gln Glu
1               5                   10                  15
Ser Tyr Gln Gln Arg Asn Pro Ala Val Gly Pro Glu Glu Ala Ala Lys
                20                  25                  30
Lys Glu Glu Ala Ala Lys Lys Pro Ala Ser Ser Arg Pro Thr Thr Tyr
            35                  40                  45
His Tyr Lys Asn Ile Tyr Gln Glu Ser Tyr Gln Gln Arg Asn Pro Ala
        50                  55                  60
Val Gly Ser Ser Gly Pro Gly Ser Ser Lys Gln Pro Asn Lys Gln Pro
65                  70                  75                  80
Asn Lys Gln Pro Asn Lys Gln Pro Asn Lys Gln Pro Asn Lys Gln Pro
                85                  90                  95
Asn Lys Gln Pro Asn Lys Gln Pro Asn Lys Gln Pro Asn Gly Pro His
                100                 105                 110
```

```
His His His His His
        115

<210> SEQ ID NO 167
<211> LENGTH: 65
<212> TYPE: PRT
<213> ORGANISM: artificial sequence
<220> FEATURE:
<223> OTHER INFORMATION: synthetic construct

<400> SEQUENCE: 167

Pro Ser Ser Arg Pro Thr Thr Tyr His Tyr Lys Asn Ile Tyr Gln Glu
1               5                   10                  15

Ser Tyr Gln Gln Arg Asn Pro Ala Val Gly Pro Glu Glu Ala Ala Lys
            20                  25                  30

Lys Glu Glu Ala Ala Lys Lys Pro Ala Ser Ser Arg Pro Thr Thr Tyr
        35                  40                  45

His Tyr Lys Asn Ile Tyr Gln Glu Ser Tyr Gln Gln Arg Asn Pro Ala
    50                  55                  60

Val
65

<210> SEQ ID NO 168
<211> LENGTH: 44
<212> TYPE: PRT
<213> ORGANISM: artificial sequence
<220> FEATURE:
<223> OTHER INFORMATION: synthetic construct

<400> SEQUENCE: 168

Lys Gln Pro Asn Lys Gln Pro Asn Lys Gln Pro Asn Lys Gln Pro Asn
1               5                   10                  15

Lys Gln Pro Asn Lys Gln Pro Asn Lys Gln Pro Asn Lys Gln Pro Asn
            20                  25                  30

Lys Gln Pro Asn Gly Pro His His His His His
        35                  40
```

PEPTIDE COMPOSITIONS FOR ORAL CARE SYSTEMS

This application claims the benefit of U.S. Provisional Patent Application No. 61/164,476 filed Mar. 30, 2009.

FIELD OF THE INVENTION

Provided herein are peptide-based compositions, oral care systems, and methods of applying particles to an oral surface.

BACKGROUND OF THE INVENTION

The cosmetic appearance of teeth is of great importance to many individuals. These individuals typically desire a "bright" smile and white teeth. Unfortunately, the surface color of teeth generally dulls and discolors over time due to the absorbent nature of dental material.

Tooth coloration is influenced by a combination of intrinsic, such as age and genetics, and extrinsic factors, such as staining caused by various foods, beverages, medications, and tobacco use. Even with regular brushing and flossing, exposure to staining and discoloring substances can cause noticeable discoloration. As such, there is a need for products and processes to quickly and safely whiten teeth.

One solution to the problem of tooth discoloration is the application of veneer facings made of porcelain, composites or ceramic. However, the application of veneer facings is expensive and requires the assistance of a trained dental professional.

Bleaching agents may be used to whiten teeth. The application of some bleaching agents may require the assistance of a dental professional (i.e., application of concentrated oxidizing agents) and/or multiple applications and may not achieve the desired degree of whitening. Over-the-counter bleaching products typically use lower concentrations of the bleaching agent(s) and often require multiple applications of the product to achieve the desired effect. However, the use of bleaching agents has been associated with several undesirable side effects including chemical burns, irritation to the gums, and an increase in tooth sensitivity.

White colorants may also be used to whiten teeth. The non-toxic colorants are typically white pigment or a combination of white pigments with other non-white pigments to achieve a more "natural" white appearance. However, the use of pigment particles to improve the cosmetic appearance of teeth generally lacks the required durability to achieve the desired cosmetic effect.

There have been various attempts to enhance the binding durability of tooth whitening agents. U.S. Patent Application Publication No. 2005-0069501 to Ibrahim et al. describes the use of a siloxane adhesive and a whitening particulate (hydroxyapatite powder) as a tooth whitening composition. PCT publication WO2006/068011 by Shimako et al. discloses a tooth whitening composition comprising (A) one or more pigments chosen from titanium dioxide, silicon dioxide, zinc oxide, aluminum oxide, magnesium oxide, and zirconium oxide, (B) pullulan, and (C) one or more members selected from lysozyme, cationized cellulose and poly lysine, wherein the components (B) and (C) are used to attach the metal oxide powder on the tooth surface. Neither reference discloses a tooth whitening system comprising a peptide-based reagent comprising a first binding element having strong affinity for a tooth surface and a second binding element capable of non-covalently binding to a ligand property of a particulate benefit agent, such as a white pigment.

Commonly owned U.S. Pat. No. 7,220,405 discloses peptide sequences that bind with high affinity to hair, skin and nails and peptide-based conditioners and colorants for hair, skin, and nails. Co-pending and commonly owned U.S. Application Publication Nos. 2005-0226839, 2008-0152600, and 2008-0280810 disclose several tooth-binding peptides identified by biopanning.

In addition to the use of pigments to whiten teeth, particles may be used to deliver a variety of other benefit agents to an oral surface. Non-limiting examples may include an enzyme, an anti-plaque agent, an anti-stain agent, an antimicrobial agent, an anti-caries agent, a flavoring agent, a coolant, or a salivating agent. As such there is a general need to provide compositions and methods to enhance the durability of particulate benefit agents to an oral surface, such as a tooth surface.

The problem to be solved is to provide oral care systems, oral care peptides, and methods of using such composition for peptide-mediated application or an oral care benefit agent to an oral surface.

SUMMARY OF THE INVENTION

Provided herein are oral care systems, oral care peptides, oral care compositions comprising oral care peptides, and methods for applying an oral care benefit agent to an oral surface.

Provided herein are oral care systems comprising:
(a) a peptide composition comprising
  (i) a first binding element having affinity for an oral surface with a $MB_{50}$ value of $10^{-5}$ molar or less; and
  (ii) a second binding element; and
(b) a composition comprising particles, said particles comprising
  (i) a benefit agent; and
  (ii) a ligand property; wherein said particles have an average particle size in the range of 0.01 micron to 10 microns; and
  wherein the second binding element and the ligand property associate with each other non-covalently or by chelation.

In one embodiment, the composition comprising particles is a stable dispersion of said particles. In some embodiments, the oral care systems provided have a stable dispersion wherein the stable dispersion is charge stabilized. Also provided are systems wherein the absolute value of the zeta potential of the stable dispersion is at least 25 mV. The stable dispersion may be sterically stabilized. The stable dispersion may comprise a dispersant, such as an ionic dispersant, a non-ionic dispersant or a combination thereof.

In one embodiment, the association between the second binding element and the ligand property is ionic-bond based, hydrogen-bond based, chelation-based, biological affinity-based, electrostatic-based or a combination thereof.

In one embodiment, the second binding element and the ligand property are selected from the group consisting of biotin and avidin, biotin and streptavidin, streptavidin tags and streptavidin, maltose binding protein and maltose, maltose binding protein and amylase, a polyhistidine tag and an affinity media comprising metal ions, glutathione S-transferase and glutathione, an epitope tag and an antibody, and combinations thereof.

In another embodiment, the first binding element comprises a plurality of oral surface-binding peptides, and in some aspects, the plurality of oral surface-binding peptides comprises more than one of the same oral surface-binding peptides.

In another embodiment, the oral surface is a tooth surface, and the tooth surface is enamel or pellicle. In some aspects, the first binding element has a greater binding affinity for an oral surface than it has for the particles.

In another embodiment, the benefit agent comprises a colorant, a whitening agent, an enzyme, an anti-plaque agent, an anti-stain agent, an antimicrobial agent, an anti-caries agent, a flavoring agent, a coolant, a salivating agent or any combination thereof.

In another embodiment, the benefit agent is a colorant, and the colorant may be a pigment, such as $TiO_2$. In some aspects, the peptide composition and the particles are provided in separate vessels.

In another embodiment, the oral care system comprises a peptide having an amino acid sequence selected from the group consisting of SEQ ID NOs: 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 96, 97, 98, 99, 100, 101, 102, 103, 104, 105, 106, 107, 108, 109, 110, 111, 112, 113, 114, 115, 120, 121, 122, 123, 125, 126, 127, 128, 129, 130, 131, 132, 133, 134, 135, 136, 137, 138, 139, 140, 141, 142, 143, and 144.

In another embodiment, the oral care system comprises a peptide having an amino acid sequence selected from the group consisting of SEQ ID NOs: 145, 146, 147, 148, 149, 150, and 151.

In another embodiment, peptide composition comprises a peptide having an amino acid sequence selected from the group consisting of SEQ ID NOs: 161, 162, 163, and 166.

In another embodiment, the peptide composition comprises a second binding element having an amino acid sequence selected from the group consisting of SEQ ID NOs: 116, 117, 119, 152, 153, 154, 155, 156, 157, 165, and 168.

Provided herein is a polypeptide comprising an amino acid sequence selected from the group consisting of SEQ ID NOs: 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 96, 97, 98, 99, 100, 101, 102, 103, 104, 105, 106, 107, 108, 109, 110, 111, 112, 113, 114, 115, 120, 121, 122, 123, 125, 126, 127, 128, 129, 130, 131, 132, 133, 134, 135, 136, 137, 138, 139, 140, 141, 142, 143, and 144.

In one aspect, a polypeptide is provided comprising an amino acid sequence selected from the group consisting of SEQ ID NOs: 161, 162, 163, and 166.

An oral care composition comprising one or more of the above polypeptides is also provided. A method is also provided herein for applying an oral care benefit agent to an oral surface comprising:

(a) providing an oral care system comprising
  (i) a peptide composition comprising
    (1) a first binding element having affinity for an oral surface with a $MB_{50}$ value of $10^{-5}$ molar or less; and
    (2) a second binding element; and
  (ii) a composition comprising particles, said particles comprising
    (1) a benefit agent; and
    (2) a ligand property; wherein said particles have an average particle size in the range of 0.01 micron to 10 microns;
    and wherein the second binding element and the ligand property associate with each other non-covalently or by chelation; and (b) contacting an oral surface with the oral care system of (a) whereby the benefit agent is applied to said oral surface.

In one embodiment of the present method, the oral surface is first contacted with the peptide composition and then contacted with the composition comprising particles.

In one embodiment of the present method, the composition comprising particles is a stable dispersion of said particles. In some embodiments, the stable dispersion is charge stabilized.

Also provided are oral care systems and methods wherein the absolute value of the zeta potential of the stable dispersion is at least 25 mV. The stable dispersion may be sterically stabilized. The stable dispersion may comprise a dispersant, such as an ionic dispersant, a non-ionic dispersant or a combination thereof.

BRIEF DESCRIPTION OF THE BIOLOGICAL SEQUENCES

The invention can be more fully understood from the following detailed description and the accompanying sequence descriptions which form a part of this application.

The following sequences conform to 37 C.F.R. 1.821-1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1-40 are the amino acid sequences of oral surface-binding peptides.

SEQ ID NOs: 41-44, 46, 48, 50-62, and 160 are the amino acid sequences of peptide linkers.

SEQ ID NOs: 45, 47, and 49 are blank.

SEQ ID NO: 63 is the nucleotide sequence of a primer.

SEQ ID NOs: 64-94 are the amino acid sequences of oral surface-binding peptides.

SEQ ID NO: 95 is the amino acid sequence of a synthetic peptide control.

SEQ ID NOs: 96-115 are the amino acid sequences of oral surface-binding peptides.

SEQ ID NO: 116 is the amino acid sequence of the histidine affinity tag "HAT" polypeptide.

SEQ ID NO: 117 is the amino acid sequence of a charged peptide block.

SEQ ID NO: 118 is the amino acid sequence of an N-terminal addition to several sequences as described in Example 10.

SEQ ID NO: 119 is a polyhistidine amino acid sequence.

SEQ ID NOs: 120-123 are the amino acid sequences of peptide compositions used to demonstrate peptide-mediated adhesion to Co—NTA polystyrene beads to enamel.

SEQ ID NO: 124 is the amino acid sequence of a silica-binding peptide.

SEQ ID NOs: 125-144 are the amino acid sequences of first binding elements comprising pellicle-binding peptides.

SEQ ID NOs: 145-151 are the amino acid sequences of pellicle-binding conjugates designed for electrostatic binding to negatively charged pigments.

SEQ ID NOs: 152-157 are the amino acid sequences of second binding elements.

SEQ ID NO: 158 is the amino acid sequence of a flexible, non-charged peptide linker.

SEQ ID NO: 159 is the nucleotide sequence of the vector pKSI(C4)E-HC77643.

SEQ ID NO: 161 is the amino acid sequence of peptide DenP03-C.

SEQ ID NO: 162 is the amino acid sequence of peptide DenP03-D.

SEQ ID NO: 163 is the amino acid sequence of peptide DE118.

SEQ ID NO: 164 is the amino acid sequence of the first binding element of peptide DE118.

SEQ ID NO: 165 is the amino acid sequence of the second binding element of peptide DE118.

SEQ ID NO: 166 is the amino acid sequence of peptide DE101.

SEQ ID NO: 167 is the amino acid sequence of the first binding element of peptide DE101.

SEQ ID NO: 168 is the amino acid sequence of the second binding element of peptide DE101.

DETAILED DESCRIPTION

Provided herein are compositions, oral care systems, and their uses for non-covalently coupling particles to an oral surface. The oral care systems described herein comprise peptide-based compositions to facilitate an interaction between the oral surface and the particles.

In this disclosure, a number of terms and abbreviations are used. The following definitions apply unless specifically stated otherwise.

As used herein, the articles "a", "an", and "the" preceding an element or component of the invention are intended to be nonrestrictive regarding the number of instances (i.e., occurrences) of the element or component. Therefore "a", "an" and "the" should be read to include one or at least one, and the singular word form of the element or component also includes the plural unless the number is obviously meant to be singular.

As used herein, the term "comprising" means the presence of the stated features, integers, steps, or components as referred to in the claims, but does not preclude the presence or addition of one or more other features, integers, steps, components or groups thereof. The term "comprising" is intended to include embodiments encompassed by the terms "consisting essentially of" and "consisting of". Similarly, the term "consisting essentially of" is intended to include embodiments encompassed by the term "consisting of".

As used herein, the term "about" modifying the quantity of an ingredient or reactant employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like.

As used herein, the term "oral care system" refers to a system comprising one or more peptide reagents that facilitate the application of (i.e., non-covalently bind) particles to an oral surface and a composition comprising particles. In a one embodiment, the composition comprising particles is a stable dispersion of the particles. Oral surfaces include those found within the oral cavity, including soft tissue such as gums, tongue, and cheeks. In one embodiment, the oral surfaces comprise tooth enamel, hydroxyapatite, tooth pellicle, and pellicle-coated hydroxyapatite. In a preferred embodiment, the oral surface comprises tooth enamel or tooth pellicle.

As used herein, the term "oral care composition" refers to a composition comprising the oral care system as well as components typically found in oral care products, such as an orally-acceptable carrier medium.

Contemplated herein is the application of particles to an oral surface to result in a desired effect on the surface. Such an effect can be considered a benefit, and thus the particles comprise "benefit agents". In one embodiment, the benefit is whitening. In a preferred embodiment, the particles comprise benefit agents which produce a whitening effect. Such benefit agents may be whitening agents or colorants. Preferred colorants include pigments such as $TiO_2$. In one embodiment, the benefit agent may be a particle comprising $TiO_2$ or silica-coated $TiO_2$ particle.

As used herein, the term "peptide-based portion of a system" refers to the peptidic component of the oral care system comprising at least one peptide having at least one first binding element coupled to at least one second binding element. In one embodiment, the peptide-based portion of the oral care system comprises a first binding element covalently coupled to a second binding element.

The term "peptide composition", as used herein, refers to a peptide-based portion of an oral care system. Peptide compositions preferably comprise a "first binding element" and a "second binding element". The "first binding element" is a single chain peptide that lacks a scaffold protein framework and lacks an immunoglobulin fold. As such, the first binding element does not include scaffold proteins, antibodies, antibody fragments ($F_{ab}$) as well as single chain variable fragments (scFv; a fusion of the variable regions of the heavy ($V_H$) and light chains ($V_L$) of immunoglobulins) and single domain camelid antibodies (Muyldermans, S., *Rev. Mol. Biotechnol.* (2001) 74:277-302). It is envisioned that for some embodiments, the first binding element and the second binding element are covalently attached to one another. For example, for certain embodiments described or exemplified herein, the peptide composition is a linear peptide comprised of the two binding elements with the proviso that the second binding element is not a biopanned peptide.

First Binding Element

The term "first binding element", as used herein, refers to a linear peptide comprising one or more oral surface-binding peptides having strong affinity for an oral surface. In one embodiment, the first binding element comprises a plurality of oral surface-binding peptides, such as tooth-binding peptides (e.g., peptides selected to having strong affinity for tooth enamel and/or pellicle).

As used herein, the term "oral surface-binding peptide" refers to a peptide that binds to an oral surface. In one embodiment, the oral surface-binding peptide is a non-naturally occurring peptide identified and/or obtained by biopanning a display library. In another embodiment, two or more oral surface-binding peptides obtained from biopanning may be combined to form the first binding element. The combination of two or more oral surface-binding peptides to form a longer binding region may be referred to herein as a "binding domain". In one embodiment, the oral surface-binding peptides are from 7 amino acids to 60 amino acids in length, more preferably, from 7 amino acids to 25 amino acids in length, most preferably from 7 to 20 amino acids in length. In a preferred embodiment, the oral-surface peptides are combinatorially-generated peptides.

The first binding element preferably comprises one or more oral surface-binding peptides identified by biopanning. Where the first binding element comprises a plurality of oral surface-binding peptides, they may be a plurality of peptides having identical sequences, or an assembly of peptides having different sequences, optionally separated by peptide spacers. Where a plurality of peptides having different sequences is used, they may all be selected to bind to the same oral-surface (e.g., all pellicle-binding peptides). However, it is also contemplated that peptides which bind to other surfaces or substrates may also be incorporated. In some embodiments, the first binding element comprises at least one "tooth-binding peptide", which is described hereafter. In some embodiments, the first binding element comprises or consists of a single oral surface-binding peptide.

The first binding element may range from 7 to 600 amino acids in length, preferably 14 to 600 amino acids in length, more preferably 7 to 200 amino acids in length, and most preferably 14 to 200 amino acids in length.

It will be appreciated that oral surface-binding peptides include "tooth-binding peptides", which are peptides that bind to a tooth surface. The term "tooth surface" refers to an oral surface comprised of tooth enamel (typically exposed after professional cleaning or polishing) or tooth pellicle (an acquired surface comprising salivary protein(s)). Hence, also included are "pellicle-binding peptides" or "enamel-binding peptides". Hydroxyapatite may be coated with salivary glycoproteins to mimic a natural tooth pellicle surface.

As used herein, the terms "pellicle" and "tooth pellicle" will refer to the thin film (typically ranging from about 20 nm to about 200 μm thick) derived from salivary glycoproteins which forms over the surface of the tooth crown. Daily tooth brushing tends to only remove a portion of the pellicle surface while abrasive tooth cleaning and/or polishing (typically by a dental professional) will expose more of the tooth enamel surface.

As used herein, the terms "enamel" and "tooth enamel" will refer to the highly mineralized tissue which forms the outer layer of the tooth. The enamel layer is composed primarily of crystalline calcium phosphate (i.e., hydroxyapatite) along with water and some organic material.

Examples of tooth-binding peptides having been disclosed in co-pending and co-owned U.S. Patent Application Publication No. 2008-0280810-A1 and are provided in Table A. Additional tooth-binding peptides are exemplified herein.

TABLE A

Examples of Oral Surface-Binding Peptides

| Target Surface | Peptide sequence | SEQ ID NO | Reference |
| --- | --- | --- | --- |
| Tooth (pellicle) | AHPESLGIKYALDGNSDPHA | 1 | US 2008-0280810 |
| Tooth (pellicle) | ASVSNYPPIHHLATSNTTVN | 2 | US 2008-0280810 |
| Tooth (pellicle) | DECMEPLNAAHCWR | 3 | US 2008-0280810 |
| Tooth (pellicle) | DECMHGSDVEFCTS | 4 | US 2008-0280810 |
| Tooth (pellicle) | DLCSMQMMNTGCHY | 5 | US 2008-0280810 |
| Tooth (pellicle) | DLCSSPSTWGSCIR | 6 | US 2008-0280810 |
| Tooth (pellicle) | DPNESNYENATTVSQPTRHL | 7 | US 2008-0280810 |
| Tooth (pellicle) | EPTHPTMRAQMHQSLRSSSP | 8 | US 2008-0280810 |
| Tooth (pellicle) | GNTDTTPPNAVMEPTVQHKW | 9 | US 2008-0280810 |
| Tooth (pellicle) | NGPDMVQSVGKHKNS | 10 | US 2008-0280810 |
| Tooth (pellicle) | NGPEVRQIPANFEKL | 11 | US 2008-0280810 |
| Tooth (pellicle) | NNTSADNPPETDSKHHLSMS | 12 | US 2008-0280810 |
| Tooth (pellicle) | NNTWPEGAGHTMPSTNIRQA | 13 | US 2008-0280810 |
| Tooth (pellicle) | NPTATPHMKDPMHSNAHSSA | 14 | US 2008-0280810 |
| Tooth (pellicle) | NPTDHIPANSTNSRVSKGNT | 15 | US 2008-0280810 |
| Tooth (pellicle) | NPTDSTHMMHARNHE | 16 | US 2008-0280810 |
| Tooth (pellicle) | QHCITERLHPPCTK | 17 | US 2008-0280810 |
| Tooth (pellicle) | TPCAPASFNPHCSR | 18 | US 2008-0280810 |
| Tooth (pellicle) | TPCATYPHFSGCRA | 19 | US 2008-0280810 |
| Tooth (pellicle) | WCTDFCTRSTPTSTSRSTTS | 20 | US 2008-0280810 |
| Tooth (enamel) | APPLKTYMQERELTMSQNKD | 21 | US 2008-0280810 |
| Tooth (enamel) | EPPTRTRVNNHTVTVQAQQH | 22 | US 2008-0280810 |

TABLE A-continued

Examples of Oral Surface-Binding Peptides

| Target Surface | Peptide sequence | SEQ ID NO | Reference |
|---|---|---|---|
| Tooth (enamel) | GYCLRGDEPAVCSG | 23 | US 2008-0280810 |
| Tooth (enamel) | LSSKDFGVTNTDQRTYDYTT | 24 | US 2008-0280810 |
| Tooth (enamel) | NFCETQLDLSVCTV | 25 | US 2008-0280810 |
| Tooth (enamel) | NTCQPTKNATPCSA | 26 | US 2008-0280810 |
| Tooth (enamel) | PSEPERRDRNIAANAGRFNT | 27 | US 2008-0280810 |
| Tooth (enamel) | THNMSHFPPSGHPKRTAT | 28 | US 2008-0280810 |
| Tooth (enamel) | TTCPTMGTYHVCWL | 29 | US 2008-0280810 |
| Tooth (enamel) | YCADHTPDPANPNKICGYSH | 30 | US 2008-0280810 |
| Tooth (enamel) | AANPHTEWDRDAFQLAMPPK | 31 | US 2008-0280810 |
| Tooth (enamel) | DLHPMDPSNKRPDNPSDLHT | 32 | US 2008-0280810 |
| Tooth (enamel) | ESCVSNALMNQCIY | 33 | US 2008-0280810 |
| Tooth (enamel) | HNKADSWDPDLPPHAGMSLG | 34 | US 2008-0280810 |
| Tooth (enamel) | LNDQRKPGPPTMPTHSPAVG | 35 | US 2008-0280810 |
| Tooth (enamel) | NTCATSPNSYTCSN | 36 | US 2008-0280810 |
| Tooth (enamel) | SDCTAGLVPPLCAT | 37 | US 2008-0280810 |
| Tooth (enamel) | TIESSQHSRTHQQNYGSTKT | 38 | US 2008-0280810 |
| Tooth (enamel) | VGTMKQHPTTTQPPRVSATN | 39 | US 2008-0280810 |
| Tooth (enamel) | YSETPNDQKPNPHYKVSGTK | 40 | US 2008-0280810 |

The first binding element may further comprise linkers ("L") and/or spacers ("S"). The spacer may be an organic spacer and/or a peptide spacer. In one embodiment, the spacer is selected from the group consisting of ethanolamine, ethylene glycol, polyethylene with a chain length of 6 carbon atoms, polyethylene glycol with 3 to 6 repeating units, phenoxyethanol, propanolamide, butylene glycol, butyleneglycolamide, propyl phenyl, ethyl alkyl chain, propyl alkyl chain, hexyl alkyl chain, steryl alkyl chains, cetyl alkyl chains, and palmitoyl alkyl chains. In another embodiment, the spacer is a peptide spacer. Suitable spacers and linkers have been described in the art, such as, for example, in U.S. Pat. No. 7,220,405 and U.S. Patent Application Publication Nos. 2005-0226839, 2007-0196305, 2006-0199206, 2007-0065387, 2008-0107614, 2008-0280810, 2007-0110686, 2006-0073111, 2006-0222609, 2008-0175798, and 2007-0265431. Some examples of suitable peptide linkers/spacers are provided in Table B.

TABLE B

Examples of Spacers and Linkers

| Spacer/linker name | Amino Acid Sequence | SEQ ID NO: |
|---|---|---|
| Example S/L 1 (caspase 3) | LESGDEVD | 41 |
| Example S/L 2 | TSTSKASTTTTSSKTTTTSSKTTTTTSKTSTTSSSST | 42 |
| Example S/L 3 | GQGGYGGLGSQGAGRGGLGGQG | 43 |
| Example S/L 4 | GPGGYGPGQQ | 44 |
| Example S/L 5 | GAG | N/A |
| Example S/L 6 | GGSGPGSGG | 46 |
| Example S/L 7 | GGG | N/A |
| Example S/L 8 | GGPKK | 48 |
| Example S/L 9 | GGP | N/A |
| Example S/L 10 | GPGVG | 50 |
| Example S/L 11 | GGGCGGG | 51 |
| Example S/L 12 | GGGC | 52 |
| Example S/L 13 | PHMASMTGGQQMGS | 53 |
| Example S/L 14 ("Lb2") | GPEEAAKKEEAAKKPA | 54 |
| Example S/L 15 | GSGGGGSGSGGGGS | 55 |

TABLE B-continued

Examples of Spacers and Linkers

| Spacer/linker name | Amino Acid Sequence | SEQ ID NO: |
|---|---|---|
| Example S/L 16 ("ton B") | GPEPEPEPEPIPEPPKEAPV VIEKPKPKPKPKPKPPA | 56 |
| Example S/L 17 | GSSGPGSS | 160 |

Also suitable are rigid peptide linkers as described in co-pending U.S. patent application Ser. No. 12/632,831 to Cheng et al.; incorporated herein by reference. Rigid linkers may include, but are not limited to, a salt bridge-stabilized α-helix forming sequences of the general formula: (Xaa1-Xaa1-Ala-Ala-Xaa2-Xaa2)$_d$ (SEQ ID NO: 57) or (Xaa1-Ala-Ala-Ala-Xaa2)$_d$ (SEQ ID NO: 58) or (Xaa1-Ala-Ala-Ala-Xaa2-Xaa3-Xaa3)$_d$ (SEQ ID NO: 59) wherein Xaa1=Glu or Asp; Xaa2=Lys or Arg; and Xaa3=Leu, Val, Ile, Phe, Trp, Met or Tyr; and wherein d=2 to 10. Also included are extended proline dipeptides of the formula: (Xaa4-Pro)$_e$ (SEQ ID NO: 60) or (Pro-Xaa4)$_e$ (SEQ ID NO: 61) or [(Xaa4-Pro)$_6$-Gly-Gly]$_e$ (SEQ ID NO: 62) wherein e=2 to 20 and Xaa4 is an acidic or basic amino acid.

Benefit Agents

As used herein, the term "benefit agent" is a general term applying to a compound or substance that provides a desired/beneficial effect or attribute to an oral surface. In one embodiment, benefit agents for oral surfaces may comprise colorants including, but not limited to, white pigments such as titanium dioxide and white minerals such as hydroxyapatite or zircon. In another embodiment, benefit agents may also include whitening agents and enzymes such as, for example, oxidases, peroxidases, proteases, lipases, glycosidases, esterases, and polysaccharide hydrolases. In another aspect, benefit agents may include anti-plaque agents, anti-stain agents, and anti-microbial agents. Antimicrobial agents may include, but are not limited to, antimicrobial peptides, magainins, cecropins, microbiocides, triclosan, chlorhexidine, cetylpyridinium chloride, quaternary ammonium compounds, chlorxylenol, chloroxyethanol, phthalic acid and its salts, thymol, and combinations thereof. Benefit agents may also include anti-caries agents, such as sodium fluoride or sodium monofluorophosphate, and flavoring agents such as oil of wintergreen, peppermint, or spearmint, or methyl salicylate, eucalyptol, or vanillin. Benefit agents may also include coolants, such as succinate-based coolant compounds, and salivating agents, to name a few. As is used herein, the term "salivating agent" refers to a material that promotes greater salivation in the user when present in the oral care composition. In one embodiment, the benefit agent is an orally-acceptable material approved for use in oral care products. In another embodiment, the orally-acceptable benefit agent is used to improve the cosmetic appearance of teeth.

In some embodiments the benefit agent may be particulate. In other embodiments the benefit agent may be associated with or loaded onto a particle which will then associate with the second binding element via the ligand property. In either case, whether the benefit agent is particulate in nature or is associated with a particle, it is preferred if the particle size remains within the average particle size range described above.

For the oral care systems described herein, it is preferred that the benefit agent is particulate with an average particle size of at least about 0.01 micron to about 10 microns. Even more preferred are benefit agents having average particle size of about 0.1 micron to about 10 microns or of about 0.1 micron to about 1 micron. Dynamic light scattering may be used to measure particle sizes less than about 10 microns.

"Average particle size" is a term of art and is used to describe a characteristic of a population of particles whether of uniform or irregular shape and dimension. Average particle sizes are determined by methods known in the art, such as a light scattering method. It will be understood by those skilled in the art that the "particle size" referenced herein will refer to the particle size measurements obtained using a light scattering methods such as laser diffraction (see ISO 13320-1:1996; International Organization for Standards, Geneva, Switzerland) and/or dynamic light scattering (see ISO 13321:1996) methodologies, both of which are known in the art. Exemplary systems are available from Malvern Instruments Ltd. Worcestershire, United Kingdom. In one embodiment, the particle size is measured using dynamic light scattering.

Second Binding Element and Ligand Property Affinity Pair

The term "second binding element", as used herein, refers to the portion of the peptide composition which has been selected as having an affinity for a ligand property of the benefit agent to be applied. While not bound by theory, the second binding element acts as "bait" to facilitate the interaction of the peptide composition with the particles via the "prey" ligand property. It is an object of the invention to provide a second binding element that binds to the particles via the ligand property without requiring selection by a biopanning process (phage display, mRNA display, etc.). The second binding element and the ligand property typically will have affinity for each other that is not based on biopanning against the particles or against the ligand property.

As used herein, the term "ligand property" refers to a property associated with the benefit agent (i.e., the "prey" component of the "bait and prey set") that associates the benefit agent with the second binding domain of the peptide composition (i.e., the "bait" component of the "bait and prey set"; also referred to herein as the "affinity set"). In some embodiments, the ligand property may be inherent to the benefit agent, for example, the benefit agent may be a negatively charged pigment and the second binding domain associates with the negative charge, or, as another example, the benefit agent may be a metal or metal ion and the second binding domain ("bait") associates with that metal or metal ion ("prey"). In other embodiments, the ligand property may be conferred upon the benefit agent, for example, the benefit agent may be covalently attached to streptavidin and the second binding domain is biotin which associates with the streptavidin ("prey"), or, the benefit agent may be itself coupled with a peptide fragment and the second binding domain ("bait") associates with the coupled peptide fragment ("prey"). It is preferred that the benefit agent retains an average particle size about 0.01 microns to about 10 microns even with an associated ligand property. Even more preferred is an average particle size of about 0.1 micron to about 1 micron.

Suitable second binding element and ligand property sets include those that interact through ionic bonds, hydrogen bonds, hydrophobic interactions, electrostatic interactions, chelation, or a combination thereof. Specifically excluded, by proviso, is the physical association of a second binding element and a ligand property via a covalent bond (i.e., the second element and the ligand property of the benefit agent are not associated with each other by a covalent bond). Therefore, suitable associations are ionic bond-based, hydrogen bond-based, hydrophobic bond-based, electrostatic-interaction based, or chelation-based components, or are based on a combination thereof. In some embodiments, the second binding element and ligand property set is based on the affinity of biotin to avidin, biotin to streptavidin, streptavidin tags to streptavidin, maltose binding protein to maltose, maltose binding protein to amylase, polyhistidine tag to a metal (e.g., a metal ion immobilized in a matrix such as an IMAC resin), glutathione S-transferase to glutathione, epitope tag to an antibody, or a combination thereof.

In one preferred aspect, the association between the second binding element and the ligand property of the benefit agent is chelation. As used herein, the term "chelation-based" pair refers to a coordinate covalent bonding complex of a Lewis acid and a Lewis base where the Lewis base donates two or more lone pairs of electrons to the Lewis acid. An example of chelation-based pairs is the interaction of various amino acid side chains and metal ions. Exemplary metals for use in chelation-based pairs include divalent metals, for example, nickel, copper, cobalt, and zinc.

Polyhistidine tags are often used to bind to immobilized metal ions such as nickel ($Ni^{2+}$), copper ($Cu^{2+}$), cobalt ($Co^{2+}$), or zinc ($Zn^{2+}$). The metal ion is typically incorporated into media/resin such as nitrilotriacetic acid (NTA)-agarose, HisPur cobalt resin, iminodiacetic acid (IDA) resin, carboxylmethylaspartate (CMA) resin, TALON® (or any other immobilized metal affinity chromatography (IMAC) resin). Metal affinity resins are commercially available from various vendors such as Thermo Fisher Scientific (Rockford, Ill.), EMD BioSciences (Madison, Wis.), and Clontech (Palo Alto, Calif.). The polyhistidine affinity tag may be synthetic or a naturally-occurring histidine affinity tag, such as the "HAT" tag (KDHLIHNVHKEFHAHAHNK; SEQ ID NO: 116) (Clontech Laboratories, Mountain View, Calif.). In one embodiment, the polyhistidine tag comprises 6 to 10 histidine residues, preferably 6 to 8 histidine residues, and most preferably 6 histidine residues. In another embodiment, the polyhistidine tag ranges from 6 to about 10, 6 about 8, or about 6 consecutive histidine residues in length.

In one embodiment, the peptidic component comprises at least one polyhistidine tag (e.g., the second binding element) capable of binding to an immobilized metal ion (i.e., the ligand property) on the surface of the particulate benefit agent. In another embodiment, the particulate benefit agent comprises an effective amount of an appropriate media (e.g., metal chelate resin) on the surface of the particle. The metal chelate resin may be applied as a partial or complete coating on the surface of the particulate benefit agent. In another embodiment, the resin applied to the surface of the particulate benefit agent comprises a tetradentate metal chelator (U.S. Pat. No. 5,962,641; herein incorporated by reference). In another embodiment, the affinity pair is a chelation pair that includes a polyhistidine-tag, i.e., an amino acid motif comprising an effective number of histidine residues capable of binding to a resin-immobilized metal ion with micromolar affinity. The polyhistidine tag is incorporated into the peptidic component acting as the second binding element and an immobilized metal ion is incorporated into the particulate benefit agent, wherein the metal ion is selected from the group consisting of nickel, copper, cobalt, zinc, and mixtures thereof.

In one embodiment, the second binding element and the ligand property of the benefit agent may be comprised of an ionic bond or electrostatic interaction. For example, affinity sets may include ionic-bond pairs. As used herein, the term "ionic bond" pair refers to an association complex of two moieties wherein one has a net positive charge and the other has a net negative charge. Electrostatic interactions are among the strongest bonds, comparable in strength to covalent bonds, and are of long-range, on the order of 50 nm.

(Isrealachvili, J. N., *Intermolecular and Surface Forces*, 2nd ed.; Academic Press: New York, N.Y. (1992) pp. 32-34).

Certain amino acids contain ionizable side groups, for example, the carboxyl groups in the side chains of aspartic and glutamic acids and the amino groups located at lysine, arginine, and histidine residues. Some peptides often contain net charges (positive or negative) and certain charge distributions when any of the charged amino acids are in the peptide sequence. The net charges of the whole or (a portion of) second binding element can induce electrostatic attraction with the oppositely charged ligand property on the benefit agent, or induce electrostatic repulsion with the similarly charged second part of the affinity pair on the benefit agent.

Examples of ionic (electrostatic) binding pairs include, but are not limited to, negatively charged peptides coupled to positively charged particulate benefit agents, negatively charged peptides coupled to particulate benefit agents comprised of or coated with a positively charged coating (e.g., anion exchange resins), positively charged peptides coupled to negatively charged particulate benefit agents (e.g., mica, silica), and positively charged peptides couple to particulate benefit agents comprising a coating that provides a negative charge (e.g., cationic exchange resins having groups such as $SO_4^{-2}$).

The charge and the charge density on the second part of the ligand property of the particulate benefit agent can be obtained and regulated with proper surface treatments and pH conditions. Charges could originate from: 1) ionization of surface functional groups such as amino, carboxyl, sulfonic, and hydroxyl groups or 2) specific adsorption of ions from solutions. In this context, "specific adsorption" implies that the adsorption is partly of non-electric nature so that the adsorbed ions can create net surface charges. For inert benefit agents, multiple surface treatment approaches in the art could be used to create ionizable functional groups: 1) using oxygen plasma to oxidize the surface or plasma polymerization of specialty gas to create surface hydroxyl and other groups (C. L. Rinsch et al, *Langmuir* (1996), 12 (2995-3002); 2) forming self-assembled monolayers with terminal function groups, such as aminopropyl silane forming siloxane monolayers on metal oxide surface (Xia, Y. N., and Whitesides, G. M., *Angew. Chem. Int. Ed.* (1998), 37:551-575); 3) using layer-by-layer assembly process to adsorb polyelectrolyte multilayer onto any surfaces to give charged surface with desired charge sign and charge density (Decher, G., *Science* (1997), 277:1232-1237); and 4) precipitation-coating of charged polymers or sol-gel. Surface charges of the particulate benefit agents could be characterized by its surface isoelectric point (IEP), the pH value at which the net surface charges are zero. So at pH lower than its IEP, the particulate benefit agent, in particular the second part of the affinity set on the particulate benefit agent, bears positive charges; while at pH greater than its IEP, the benefit agent bears negative charges.

Electrostatic interaction ranges can be further modulated with ionic strength: lower ionic strength provides longer interaction range, while higher ionic strength provides shorter interaction range. The modulation of the interaction range can be applied to obtaining stable peptide-benefit agent adduct at low ionic strength, but enhancing benefit agent delivery to oral surfaces at higher ionic strength.

The net charge of the first part of the affinity set may be negative or positive depending upon the pH of the system. In one embodiment, the net charge of the second binding domain is positive at a specified pH wherein the pH may range from 3.0 to about 10. In another embodiment, the net charge of the second binding domain is negative at a specified pH wherein the pH may range from 3.0 to about 10.

For example, the second binding element may be positively charged and comprise repeats of the sequence KQPN (SEQ ID NO: 117) or repeats of the sequence GK and may physically associate with a negatively charged pigment. In a preferred aspect, the negatively charged pigment is a silica-coated pigment. In a further aspect, the negatively charged particle is a siliceous particle, such as a mesoporous silica particle.

In a preferred embodiment, the second binding element is a domain of positively charged amino acids which is known to associate with a negatively charged pigment (coated or uncoated). It will be appreciated that for an electrostatic-based interaction, the second binding element and a ligand property should be oppositely charged.

In one aspect, second binding element and ligand property sets may be a biological pair as described herein and may include, but are not limited to, biotin:avidin, biotin:streptavidin, streptavidin tags:streptavidin, maltose binding protein (MBP):maltose or amylase, and glutathione S-transferase (GST):glutathione. The set may include an epitope tag:antibody pair so long as the second binding element of the peptidic component comprises the epitope tag and the particulate benefit agent comprises the corresponding antibody or antibody fragment. Examples of commercially available epitope tags include, but are not limited to, HA-tag, FLAG-tag, E-tag, S-tag, and myc-tag. In another embodiment, the second binding element and ligand property pair does not include an epitope tag:antibody pair.

In another embodiment, second binding elements and ligand properties may be interchanged in the systems described herein. For example, biotin may be considered either a second binding element or a ligand property, depending on whether it is associated with a peptide composition or a binding agent as described herein. Conversely, streptavidin may be considered the binding element or the ligand property, depending on its association.

For embodiments of the oral care systems described herein, the peptide composition and the benefit agent will bind to each other via the second binding domain and the ligand property, respectfully. It is preferred that the second-binding domain and ligand property association is the only association between the peptide composition and the benefit agent, and that, as described above for the second binding element and ligand property sets, the association is ionic bond-based, hydrogen bond-based, hydrophobic bond-based, electrostatic-based, or chelation-based, or a combination thereof.

In some embodiments, the first binding domain binds more strongly to an oral surface than it does to the particles which comprise a benefit agent having a ligand property. In some embodiments, the first binding domain binds an oral surface with an $MB_{50}$ value at least one order of magnitude lower (i.e., binds more strongly) than it does to the particles. In other embodiments, the $MB_{50}$ value of the first binding domain to an oral surface is at least two orders of magnitude lower than that of the first binding domain with the particles.

Stable Particle Dispersion and Zeta Potential

As used herein, "stable dispersion" refers to a matrix in which particles are dispersed, and wherein the average particle size remains fairly constant with time. For the purposes described herein, a sample (i.e., the particle dispersion) may be considered stably dispersed if the average particle size of the sample does not increase by more than 50% over several days. In another embodiment, the sample may be stably-dispersed if the average particle size of the particles in the sample does not increase by more than 50% over the initial particle size of the particles within 2 days after dispersion formation. In certain embodiments, there is no more than a 50% increase in average particle size within 3 days after dispersion formation. In another embodiment, there is no more than a 50% increase in average particle size within at least 5 days of dispersion formation. In still other embodiments, there is no more than a 50% increase in average particle size within 7 days of dispersion formation. In yet another embodiment, a particulate dispersion may be considered stable when the average particle size does not increase more than 50% over at least 7 days, without the detection of any agglomerates larger than 50 primary particles. One of skill in the art will recognize that stable particle dispersions may have some settling over time, so long as the particles can be re-dispersed easily with a minimal amount of energy (e.g., gentle manual shaking/agitation that is typically associated with manual mixing/shaking to reform a uniform dispersion of particles within the oral care composition or oral care system).

The stable dispersion may be achieved using techniques known in the art. In some embodiments, the stable dispersion is charge-stabilized or sterically-stabilized. In some embodiments, the stable dispersion comprises a dispersant. As used herein, the term "dispersant" refers to a substance that stabilizes the formation of a colloidal solution of solid pigment particles in a liquid medium. In some embodiments, the dispersant is an ionic dispersant or a non-ionic dispersant. Dispersants may include but are not limited to sodium lauryl sulfate, sodium methyl cocoyl taurate, poloxomer 407, sodium n-lauroyl sarcosinate, sodium dodecyl benzene sulfonate, PEG-40 castoroil, TWEEN® 20, cocamidopropyl betaine, sodium lauryl ether sulfate.

The stability of the dispersion can be related to the zeta potential. The zeta potential indicates the degree of repulsion between adjacent, similarly charged particles in a dispersion. Colloids with high zeta potential (negative or positive) are electrically stabilized while colloids with low zeta potentials tend to coagulate or flocculate ("Zeta Potential of Colloids in Water and Waste Water", ASTM Standard D 4187-82, American Society for Testing and Materials, 1985).

The zeta potential can be measured using methods/equipment known in the art. Briefly, a dispersion solution is measured in an applied electric field. The mobility of the dispersed particles in the electric field is measured using laser light scatting. The mobility is converted to zeta potential using known constants for the solution viscosity. In some embodiments, the absolute value of the zeta potential of an electrically stable dispersion is at least 25 mV. A high absolute zeta potential is indicative of a charge-stabilized dispersion that will resist aggregation and time-dependent growth of the average particle size.

Binding Affinity

The term "$MB_{50}$" refers to the concentration of the binding peptide that gives a signal that is 50% of the maximum signal obtained in an ELISA-based binding assay (see present Example 11 and U.S. Published Patent Application No. 2005-0226839). The $MB_{50}$ value provides an indication of the strength of the binding interaction or affinity of the components of the complex. The lower the $MB_{50}$ value, the stronger the interaction of the peptide with its corresponding substrate. The term "binding affinity" refers to the strength of the interaction of a binding peptide with a given substrate. The binding affinity is defined herein in terms of the $MB_{50}$ value, determined in an ELISA-based binding assay.

Peptides having an affinity for a target surface (i.e., target surface-binding peptides) may be selected using combinatorial methods that are well known in the art or may be empirically generated. It is preferred that the first binding element of the peptide composition whether it is comprised of one or a plurality of oral surface binding peptides binds to an oral surface with a binding affinity as measured by $MB_{50}$ values, of less than or equal to about $10^{-5}$ M, more preferably less than or equal to about $10^{-6}$ M, even more preferably less than or equal to about $10^{-7}$ M, and even more preferably less than or equal to about $10^{-8}$ M.

In one embodiment, the term "high affinity" or "strong affinity" will be used to describe oral surface-binding peptides having a binding affinity, as measured by an $MB_{50}$ value, less than or equal to about $10^{-5}$ M, preferably less than or equal to about $10^{-6}$ M, more preferably less than or equal to about $10^{-7}$ M, and even more preferably less than or equal to about $10^{-8}$ M.

Methods and Uses of Oral Care Systems

Provided and exemplified herein is a method of applying (i.e., non-covalently binding) particles to an oral surface comprising contacting an oral surface with a peptide composition and subsequently contacting the peptide composition with particles comprising a ligand property. In some embodiments, the particles also comprise an oral benefit agent. In one embodiment, the particles are the benefit agents. Colorants and whitening agents are preferred oral benefit agents. In a preferred aspect the whitening agent comprise the pigment $TiO_2$.

To carry out certain methods provided, it is necessary to provide a peptide composition and particles as described herein. The peptide composition may be applied to an oral surface and the particulate benefit agent is subsequently applied. The peptide composition and the composition comprising the particulate benefit agent may be provided in separate vessels. It will be appreciated that the peptide composition is preferably applied and contacts the oral surface for a time sufficient to bind to the oral surface prior to the application of the particulate benefit agent. The particulate benefit agent is itself preferably applied and contacts the oral surface for a time sufficient to bind to the peptide composition.

Peptide compositions and first binding domains provided may be used in oral care systems. In some embodiments, the peptide composition comprises a first binding element which binds to an oral surface with an $MB_{50}$ value of about $10^{-5}$ M or less and further comprises a second binding element. The oral care system may further comprise particles or a stable dispersion of particles, the particles comprising a benefit agent and a ligand property. In preferred systems, the peptide composition and the particles associate via the second binding element and the ligand property, respectively.

Biopanning and Identification of Oral Surface-Binding Peptides

In one embodiment, the oral surface-binding peptides are combinatorially-generated and range from 7 amino acids to 60 amino acids in length, more preferably, from 7 amino acids to 25 amino acids in length, most preferably from 7 to 20 amino acids in length. Due to their short length and linear nature, the oral surface-binding peptides of the present invention exclude, by proviso, target surface-binding antibodies and target surface-binding single chain antibodies. The oral surface-binding peptides may be generated randomly and then selected against the target surface (for example, a tooth surface selected from the group consisting of tooth enamel and tooth pellicle).

The generation of random libraries of peptides is well known and may be accomplished by a variety of techniques including, but not limited to, bacterial display (Kemp, D. J.; Proc. Natl. Acad. Sci. USA 78(7): 4520-4524 (1981); yeast display (Chien et al., Proc Natl Acad Sci USA 88(21): 9578-82 (1991)), combinatorial solid phase peptide synthesis (U.S. Pat. Nos. 5,449,754; 5,480,971; 5,585,275 and 5,639,603), phage display technology (U.S. Pat. Nos. 5,223,409; 5,403,484; 5,571,698; and 5,837,500), ribosome display (U.S. Pat. Nos. 5,643,768; 5,658,754; and 7,074,557), and mRNA display technology (PROFUSION™; U.S. Pat. Nos. 6,258,558; 6,518,018; 6,281,344; 6,214,553; 6,261,804; 6,207,446; 6,846,655; 6,312,927; 6,602,685; 6,416,950; 6,429,300; 7,078,197; and 6,436,665). Techniques to generate such biological peptide libraries are described in Dani, M., J. Receptor & Signal Transduction Res., 21(4):447-468 (2001). Additionally, phage display libraries are available commercially from companies such as New England BioLabs (Beverly, Mass.).

A preferred method to obtain target surface-binding peptides is by phage display. Phage display is an in vitro selection technique in which a peptide or protein is genetically fused to a coat protein of a bacteriophage, resulting in display of the fused peptide on the exterior of the phage virion, while the DNA encoding the fusion resides within the virion. This physical linkage between the displayed peptide and the DNA encoding it allows screening of vast numbers of variants of peptides, each linked to a corresponding DNA sequence, by a simple in vitro selection procedure called "biopanning". In its simplest form, biopanning is carried out by incubating the pool of phage-displayed variants with a target of interest that has been immobilized on a plate or bead, washing away unbound phage, and eluting specifically bound phage by disrupting the binding interactions between the phage and the target. The eluted phage is then amplified in vivo and the process is repeated, resulting in a stepwise enrichment of the phage pool in favor of the tightest binding sequences. After 3 or more rounds of selection/amplification, individual clones are characterized by DNA sequencing.

More specifically, after a suitable library of peptides has been generated or purchased, the library is then contacted with an appropriate amount of the test substrate. The library of peptides is dissolved in a suitable solution for contacting the target surface which is typically suspended in solution or may be immobilized on a plate or bead. A preferred solution is a buffered aqueous saline solution containing a surfactant. A suitable solution is Tris-buffered saline (TBS) with 0.5% TWEEN® 20. The solution may additionally be agitated by any means in order to increase the mass transfer rate of the peptides to the target sample/surface, thereby shortening the time required to attain maximum binding.

Thus, the following method for generating the target surface-binding peptides may be used. A library of combinatorially generated phage-peptides is contacted with the target surface of interest (i.e., an oral surface. such as a tooth surface), to form phage peptide-target surface complexes. The phage-peptide-target surface complex is separated from uncomplexed peptides and unbound substrate, and the bound phage-peptides from the phage-peptide-target surface complexes is eluted from the complex, preferably using an acidic solution. Then, the eluted phage-peptides are identified and sequenced. To identify peptide sequences that bind to one substrate but not to another, for example peptides that bind to another surface (i.e., a "non-target" surface; for example, another material surface such as hair, skin, nail, etc.), a subtractive panning step may be used. Specifically, the library of combinatorially generated phage-peptides is first contacted with the non-target surface to remove phage-peptides that bind to it. Then, the non-binding phage-peptides are contacted with the desired substrate and the above process is followed. Alternatively, the library of combinatorially-generated phage peptides may be contacted with the non-target and the desired substrate simultaneously. Then, the phage-peptide-target surface complexes are separated from the phagepeptide-non-target complexes and the method described above is followed for the desired phage-peptide-target surface complexes.

In one embodiment, a modified phage display screening method for isolating peptides with a higher affinity for the target surface may be used. In the modified method, the phage-peptide-target surface complexes are formed as described above. Then, these complexes are treated with an elution buffer. Any of the elution buffers described above may be used. Preferably, the elution buffer is an acidic solution. Then, the remaining, elution-resistant phage-peptide-target surface complexes are used to directly infect a bacterial host cell, such as E. coli ER2738. The infected host cells are grown in an appropriate growth medium, such as LB (Luria-Bertani) medium, and this culture is spread onto agar, containing a suitable growth medium, such as LB medium with IPTG (isopropyl β-D-thiogalactopyranoside) and S-GAL™. After growth, the plaques are picked for DNA isolation and are sequenced to identify the peptide sequences with a high binding affinity for the target surface of interest.

In another embodiment, PCR may be used to identify the elution-resistant phage-peptides from the modified phage display screening method, described above, by directly carrying out PCR on the phage-peptide-target surface complexes using the appropriate primers, as described by Janssen et al. in U.S. Patent Application Publication No. 2003-0152976,.

Peptide Production

The peptides described herein may be prepared using standard peptide synthesis methods, which are well known in the art (see for example Stewart et al., *Solid Phase Peptide Synthesis,* Pierce Chemical Co., Rockford, Ill., 1984; Bodanszky, *Principles of Peptide Synthesis,* Springer-Verlag, New York, 1984; and Pennington et al., *Peptide Synthesis Protocols,* Humana Press, Totowa, N.J., 1994). Additionally, many companies offer custom peptide synthesis services.

Alternatively, the peptides described herein may be prepared using recombinant DNA and molecular cloning techniques. Genes encoding the peptides may be produced in heterologous host cells, particularly in the cells of microbial hosts.

Preferred heterologous host cells for expression of the peptides of the present invention are microbial hosts that can be found broadly within the fungal or bacterial families and which grow over a wide range of temperature, pH values, and solvent tolerances. Because transcription, translation, and the protein biosynthetic apparatus are the same irrespective of the cellular feedstock, functional genes are expressed irrespective of carbon feedstock used to generate cellular biomass. Examples of host strains include, but are not limited to, fungal or yeast species from genera such as *Aspergillus, Trichoderma, Saccharomyces, Pichia, Candida, Yarrowia, Hansenula,* or bacterial species from genera such as *Salmonella, Bacillus, Acinetobacter, Rhodococcus, Streptomyces, Escherichia, Pseudomonas, Methylomonas, Methylobacter, Alcaligenes, Synechocystis, Anabaena, Thiobacillus, Methanobacterium,* and *Klebsiella.*

A variety of expression systems can be used to produce the peptides of the present invention. Such vectors include, but are not limited to chromosomal, episomal and virus-derived vectors, e.g., vectors derived from bacterial plasmids, from bacteriophage, from transposons, from insertion elements, from yeast episomes, from viruses such as baculoviruses, retroviruses and vectors derived from combinations thereof such as those derived from plasmid and bacteriophage genetic elements, such as cosmids and phagemids. The expression system constructs may contain regulatory regions that regulate as well as engender expression. In general, any system or vector suitable to maintain, propagate or express polynucleotide or polypeptide in a host cell may be used for expression in this regard. Microbial expression systems and expression vectors contain regulatory sequences that direct high level expression of foreign proteins relative to the growth of the host cell. Regulatory sequences are well known to those skilled in the art and examples include, but are not limited to, those which cause the expression of a gene to be turned on or off in response to a chemical or physical stimulus, including the presence of regulatory elements in the vector, for example, enhancer sequences. Any of these could be used to construct chimeric genes for production of the any of the binding peptides of the present invention. These chimeric genes could then be introduced into appropriate microorganisms via transformation to provide high level expression of the peptides.

Vectors or cassettes useful for the transformation of suitable host cells are well-known in the art. Typically the vector or cassette contains sequences directing transcription and translation of the relevant gene, one or more selectable markers, and sequences allowing autonomous replication or chromosomal integration. Suitable vectors comprise a region 5' of the gene, which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host. Selectable marker genes provide a phenotypic trait for selection of the transformed host cells such as tetracycline or ampicillin resistance in *E. coli.*

Initiation control regions or promoters which are useful to drive expression of the chimeric gene in the desired host cell are numerous and familiar to those skilled in the art. Virtually any promoter capable of driving the gene is suitable for producing the binding peptides of the present invention including, but not limited to: CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, pBAD, tet, trp, $IP_L$, $IP_R$, T7, tac, and trc (useful for expression in *Escherichia coli*) as well as the amy, apr, npr promoters and various phage promoters useful for expression in *Bacillus.*

Termination control regions may also be derived from various genes native to the preferred hosts. Optionally, a termination site may be unnecessary, however, it is most preferred if included.

The vector containing the appropriate DNA sequence, as well as an appropriate promoter or control sequence, may be employed to transform an appropriate host to permit the host to express the peptide of the present invention. Cell-free translation systems can also be employed to produce such peptides using RNAs derived from the DNA constructs of the present invention. Optionally it may be desired to produce the instant gene product as a secretion product of the transformed host. Secretion of desired proteins into the growth media has the advantages of simplified and less costly purification procedures. It is well known in the art that secretion signal sequences are often useful in facilitating the active transport of expressible proteins across cell membranes. The creation of a transformed host capable of secretion may be accomplished by the incorporation of a DNA sequence that codes for a secretion signal which is functional in the production host. Methods for choosing appropriate signal sequences are well known in the art (see for example European Patent EP546049 B1 and WO 93/24631).

Oral Care Compositions

Contemplated herein are oral care systems comprising an effective amount of one or more of the present peptide compositions and a composition comprising an effective amount of one or more particles comprising (or acting as) the benefit agent. As used here, the term "effective amount" is that amount of at least one of the present peptide compositions or that amount of at least one or more particles comprising benefit agent incorporated into the oral care composition to achieve the desired benefit, such as tooth whitening.

The oral care compositions may be in the form of powder, paste, gel, liquid, ointment, or tablet. Exemplary oral care compositions may include, but are not limited to, toothpaste, dental cream, gel or tooth powder, mouth wash, breath freshener, and dental floss. The oral care compositions comprise effective amounts of the peptide compositions of the invention in an orally acceptable carrier medium. Effective amounts of the peptide composition and the composition comprising particles (i.e., the oral care system) for use in an oral care composition may vary depending on the type of product. Typically, the effective amount of the oral care system is a proportion from about 0.01% to about 90% by weight relative to the total weight of the oral care composition. Additionally, a mixture of different oral care systems (comprising different benefit agents, for example) may be used in the oral care composition. It will be appreciated that the components in the mixture are chosen so that there is no interaction between the peptide compositions that mitigate the desired effect. Suitable mixtures of oral care systems disclosed herein may be determined by one skilled in the art using routine experimentation. If a mixture of oral care systems is used in the composition, the total concentration of the reagents (peptide compositions and particulate benefit agents) is about 0.01% to about 90% by weight relative to the total weight of the oral care composition.

Components of an orally-acceptable carrier medium are described by White et al. in U.S. Pat. No. 6,740,311; Lawler et al. in U.S. Pat. No. 6,706,256; Fuglsang et al. in U.S. Pat. No. 6,264,925; and Ibrahim et al., U.S. Patent Application Publication No. 2005-0069501, each of which are incorporated herein by reference in their entirety. For example, the oral care composition may comprise one or more of the following: abrasives, surfactants, antioxidants, chelating agents, fluoride sources, thickening agents, buffering agents, solvents, humectants, carriers, bulking agents, and oral benefit agents, such as enzymes, anti-plaque agents, anti-staining agents, antimicrobial agents, anti-caries agents, anti-inflammatory agents, desensitizing agents, sweetening agents, flavoring agents, breath-freshening agents, coolants, nutrients, and salivating agents.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any naturally-occurring amino acid (or as defined herein) | Xaa | X |

EXAMPLES

General Methods

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et. al., *Short Protocols in Molecular Biology*, 5th Ed., John Wiley and Sons, Inc., N.Y., 2002.

Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C., 1994, or by Thomas D. Brock in *Biotechnology: A Textbook of Industrial Microbiology*, Second Edition, Sinauer Associates, Inc., Sunderland, Mass., 1989. All reagents, restriction enzymes and materials used for the growth and maintenance of bacterial cells were obtained from Aldrich Chemicals (Milwaukee, Wis.), BD Diagnostic Systems (Sparks, Md.), Life Technologies (Rockville, Md.), or Sigma-Aldrich Chemical Company (St. Louis, Mo.), unless otherwise specified.

The meaning of abbreviations used is as follows: "min" means minute(s), "h" means hour(s), "µL" means microliter(s), "mL" means milliliter(s), "L" means liter(s), "nm" means nanometer(s), "mm" means millimeter(s), "cm" means centimeter(s), "µm" means micrometer(s), "mM" means millimolar, "µM" means micromolar, "M" means molar, "mmol" means millimole(s), "µmole" means micromole(s), "g" means gram(s), "µg" means microgram(s), "mg" means milligram(s), "g" means the gravitation constant, "RCF" means relative centrifugal force, "rpm" means revolution(s) per minute, and "pfu" means plaque forming unit(s).

Example 1

Selection of Tooth (Pellicle) Binding Peptides Using Standard Biopanning

The purpose of this Example was to identify phage peptides that bind tooth pellicle using standard phage display biopanning.

Compressed hydroxyapatite disks (HAP disk, 3 mm diameter) were used to form the pellicles by incubating the disks inside a human mouth for 1.5 hours followed by TBS rinse. The disks were then incubated in SUPERBLOCK® blocking buffer (Pierce Chemical Company, Rockford, Ill.; Prod. #37535) for 1 hour at room temperature, followed by 3 washes with TBST (TBS in 0.05% TWEEN® 20). Libraries of phage containing random peptide inserts ($10^{11}$ pfu) from 14 to 20 amino acids were added to each tube. After 60 minutes of incubation at room temperature and shaking at 50 rpm, unbound phages were removed by aspirating the liquid out of each well followed by 6 washes with 1.0 mL TBS containing the detergent TWEEN® 20 (TBST) at a final concentration of 0.05%.

The sample disks were then transferred to clean tubes and 200 µL of elution buffer consisting of 1 mg/mL BSA in 0.2 M glycine-HCl, pH 2.2, was added to each well and incubated for 10 min to elute the bound phages. Then, 32 µL of neutralization buffer consisting of 1 M Tris-HCl, pH 9.2, was added to each well. The phage particles, which were in the elution buffer as well as on the sample disks, were amplified by incubating with diluted E. coli ER2738 cells, from an overnight culture diluted 1:100 in LB medium, at 37° C. for 4.5 h. After this time, the cell culture was centrifuged for 30 s and the upper 80% of the supernatant was transferred to a fresh tube, ⅙ volume of PEG/NaCl (20% polyethylene glycol-800, 2.5 M sodium chloride) was added, and the phage was allowed to precipitate overnight at 4° C. The precipitate was collected by centrifugation at 10,000×g at 4° C. and the resulting pellet was resuspended in 1 mL of TBS. This was the first round of amplified stock. The amplified first round phage stock was then tittered according to the standard protocol. For the $2^{nd}$, $3^{rd}$ and $4^{th}$ round of biopanning, more than $2\times10^{11}$ pfu of phage stock from the previous round was used. The biopanning process was repeated for 2 more rounds under the same conditions as described above. The same biopanning condition was used for the $4^{th}$ round, except the washing solution was TBS with 0.5% TWEEN® 20 instead of 0.05% TWEEN® 20.

After the $4^{th}$ round of biopanning, 95 random single phage plaque lysates were prepared following the manufacture's instructions (New England Biolabs) and the single stranded phage genomic DNA was purified using the QIAprep Spin M13 Kit (Qiagen, Valencia, Calif.) and sequenced at the DuPont Sequencing Facility using −96 gIII sequencing primer (5'-CCCTCATAGTTAGCGTAACG-3'; SEQ ID NO: 63). The displayed peptide is located immediately after the signal peptide of gene III. Based on the peptide sequences present in the $3^{rd}$ and $4^{th}$ round analysis, 20 phage candidates were selected for further pellicle binding analysis.

Example 2

Characterization of Tooth (Pellicle) Binding Peptide Candidates on Pellicle Surface A total of 20 selected phage candidates (Example 1) were used in a phage ELISA experiment. Purified phage lysates were used for binding to pellicle-coated HAP disks using an anti-M13 phage antibody conjugated to horseradish-peroxidase, followed by the addition of chromogenic agent TMB (3,3',5,5'-tetramethylbenzidine), obtained from Pierce Biotechnology (Item #34021; Rockford, Ill.). The plates were read at $A_{450\ nm}$.

For each phage candidate to be tested, the pellicle-coated HAP disks (3 mm diameter) was incubated for 1 h at room temperature with 200 µL of blocking buffer, consisting of 2% non-fat dry milk (Schleicher & Schuell, Inc.) in TBS. The blocking buffer was removed by aspirating the liquid out of each tube. The tube was rinsed 6 times with wash buffer consisting of TBST-0.05%. The wells were filled with 200 µL of TBST-0.5% containing 1 mg/mL BSA (bovine serum albumin) and then 10 µL (over $10^{10}$ pfu) of purified phage stock was added. The samples were incubated at room temperature for 60 min with slow shaking. The non-binding phage were removed by washing 6 times with TBST-0.5%. Then, 100 µL of horseradish peroxidase/anti-M13 antibody conjugate (Amersham USA, Piscataway, N.J.), diluted 1:500 in the blocking buffer, was added and incubated for 1 h at room temperature. The conjugate solution was removed and was washed 6 times with TBST-0.5%. TMB substrate (200 µL) was added to each well and the color was allowed to develop for 5 to 30 min, typically for 10 min, at room temperature. Then, stop solution (200 µL of 2 M $H_2SO_4$) was added to each well and the solution was transferred to a 96-well plate and the $A_{450}$ was measured using a microplate spectrophotometer (Molecular Devices, Sunnyvale, Calif.). The resulting absorbance values are given in Table 1.

TABLE 1

Amino Acid Sequences of Tooth (Pellicle)-Binding Peptides

| Phage ID | Amino Acid Sequence | SEQ ID NO. | O.D.$_{450}$ |
|---|---|---|---|
| Control | No phage | — | 0.218 |
| Pell 1 | AHPESLGIKYALDGNSDPHA | 1 | 0.739 |
| Pell 2 | ASVSNYPPIHHLATSNTTVN | 2 | 0.75 |
| Pell 3 | DECMEPLNAAHCWR | 3 | 0.49 |
| Pell 4 | DECMHGSDVEFCTS | 4 | 0.664 |
| Pell 5 | DLCSMQMMNTGCHY | 5 | 0.83 |
| Pell 6 | DLCSSPSTWGSCIR | 6 | 0.735 |
| Pell 7 | DPNESNYENATTVSQPTRHL | 7 | 0.831 |
| Pell 8 | EPTHPTMRAQMHQSLRSSSP | 8 | 0.712 |
| Pell 9 | GNTDTTPPNAVMEPTVQHKW | 9 | 0.755 |
| Pell 10 | NGPDMVQSVGKHKNS | 10 | 0.729 |
| Pell 11 | NGPEVRQIPANFEKL | 11 | 0.607 |
| Pell 12 | NNTSADNPPETDSKHHLSMS | 12 | 0.521 |
| Pell 13 | NNTWPEGAGHTMPSTNIRQA | 13 | 0.598 |
| Pell 14 | NPTATPHMKDPMHSNAHSSA | 14 | 0.7 |
| Pell 15 | NPTDHIPANSTNSRVSKGNT | 15 | 0.567 |
| Pell 16 | NPTDSTHMMHARNHE | 16 | 0.578 |
| Pell 17 | QHCITERLHPPCTK | 17 | 0.614 |
| Pell 18 | TPCAPASFNPHCSR | 18 | 0.416 |
| Pell 19 | TPCATYPHFSGCRA | 19 | 0.731 |
| Pell 20 | WCTDFCTRSTPTSTSRSTTS | 20 | 0.715 |

Oral surfaces contemplated herein include tooth and, more specifically, pellicle. In one embodiment, the peptide composition or the first binding element comprise at least one peptide having the sequence of SEQ ID NO: 1, 2, 3, 4, 5, 6, 7, 8, 9, 10, 11, 12, 13, 14, 15, 16, 17, 18, 19, or 20. In some embodiments, the peptide composition or the first binding element comprise a plurality of peptides, wherein at least one of the peptides has the sequence of SEQ ID NO: 1, 2, 3, 4, 5, 6, 7, 8, 9, 10, 11, 12, 13, 14, 15, 16, 17, 18, 19, or 20.

Example 3

Selection of Tooth (Enamel) Binding Peptides Using Standard Biopanning

The purpose of this example was to identify phage peptides that bind tooth enamel using standard phage display biopanning.

The unpolished bovine enamel blocks from incisors (3 mm squares) and polished bovine enamel disks from the incisors (3 mm diameter disks) were embedded in wax to form a well with only the intended surfaces exposed. The enamel surfaces were then incubated in SUPERBLOCK® blocking buffer (Pierce Chemical Company, Rockford, Ill.; Prod. #37535) for 1 hour at room temperature (~22° C.), followed by 3 washes with TBST (TBS in 0.05% TWEEN® 20). Libraries of phage containing random peptide inserts ($10^{11}$ pfu) from 14 to 20 amino acids were added to the enamel well for 10 minutes pre-absorption to titrate the wax surface, unbound phages were removed by aspirating the liquid out of each well. Then, 100 µL of the same phage library ($10^{11}$ pfu) was added to the enamel well for 60 min incubation at room temperature with slow 50 rpm shaking, followed by 6 washes with 1.0 mL TBS containing the detergent TWEEN® 20 (TBST) at a final concentration of 0.05%.

The enamel blocks were then cut out of the wax well and transferred to a clean tube and 200 µL of elution buffer consisting of 1 mg/mL BSA in 0.2 M glycine-HCl, pH 2.2, was added to each well and incubated for 10 min to elute the bound phages. Then, 32 µL of neutralization buffer consisting of 1 M Tris-HCl, pH 9.2, was added to each tube. The phage particles, which were in the elution buffer as well as on the enamel blocks, were amplified by incubating with diluted *E. coli* ER2738 cells, from an overnight culture diluted 1:100 in LB medium, at 37° C. for 4.5 h. After this time, the cell culture was centrifuged for 30 s and the upper 80% of the supernatant was transferred to a fresh tube, ⅙ volume of PEG/NaCl (20% polyethylene glycol-800, 2.5 M sodium chloride) was added, and the phage was allowed to precipitate overnight at 4° C. The precipitate was collected by centrifugation at 10,000×g at 4° C. and the resulting pellet was resuspended in 1 mL of TBS. This was the first round of amplified stock. The amplified first round phage stock was then tittered according to the standard protocol. For the $2^{nd}$ round of biopanning, more than $2\times10^{11}$ pfu of phage stock from the previous round was used. The biopanning process was repeated for 1 more round under the same conditions as described above. The same biopanning condition was used for the $3^{rd}$ round, except the washing solution was TBS with 0.5% TWEEN® 20 instead of 0.05% TWEEN® 20.

After the $3^{rd}$ round of biopanning, 95 random single phage plaque lysates were prepared following the manufacture's instructions (New England Biolabs) and the single stranded phage genomic DNA was purified using the QIAprep Spin M13 Kit (Qiagen, Valencia, Calif.) and sequenced at the DuPont Sequencing Facility using −96 gIII sequencing primer (5'-CCCTCATAGTTAGCGTAACG-3'), given as SEQ ID NO:63. The displayed peptide is located immediately after the signal peptide of gene III. Based on the peptide sequences, 20 phage candidates were selected for further pellicle binding analysis (Table 2). "BoEn" means bovine enamel and "BoEn P" means polished bovine enamel.

TABLE 2

Bovine Enamel Tooth-Binding Peptide Sequences

| Phage ID | Amino Acid Sequence | SEQ ID NO: |
|---|---|---|
| BoEn P1 | APPLKTYMQERELTMSQNKD | 21 |
| BoEn P2 | EPPTRTRVNNHTVTVQAQQH | 22 |
| BoEn P3 | GYCLRGDEPAVCSG | 23 |
| BoEn P4 | LSSKDFGVTNTDQRTYDYTT | 24 |
| BoEn P5 | NFCETQLDLSVCTV | 25 |
| BoEn P6 | NTCQPTKNATPCSA | 26 |
| BoEn P7 | PSEPERRDRNIAANAGRFNT | 27 |
| BoEn P8 | THNMSHFPPSGHPKRTAT | 28 |
| BoEn P9 | TTCPTMGTYHVCWL | 29 |
| BoEn P10 | YCADHTPDPANPNKICGYSH | 30 |
| BoEn 1 | AANPHTEWDRDAFQLAMPPK | 31 |
| BoEn 2 | DLHPMDPSNKRPDNPSDLHT | 32 |
| BoEn 3 | ESCVSNALMNQCIY | 33 |
| BoEn 4 | HNKADSWDPDLPPHAGMSLG | 34 |
| BoEn 5 | LNDQRKPGPPTMPTHSPAVG | 35 |
| BoEn 6 | NTCATSPNSYTCSN | 36 |
| BoEn 7 | SDCTAGLVPPLCAT | 37 |
| BoEn 8 | TIESSQHSRTHQQNYGSTKT | 38 |
| BoEn 9 | VGTMKQHPTTTQPPRVSATN | 39 |
| BoEn 10 | YSETPNDQKPNPHYKVSGTK | 40 |

Oral surfaces contemplated herein include tooth and, more specifically, enamel. In one embodiment, the peptide composition or the first binding element comprise at least one peptide having the sequence of SEQ ID NO: 21, 22, 23, 24, 25, 26, 27, 28, 29, 30, 31, 32, 33, 34, 35, 36, 37, 38, 39, or 40. In some embodiments, the peptide composition or the first binding element comprise a plurality of peptides, wherein at least one of the peptides has the sequence of SEQ ID NO: 21, 22, 23, 24, 25, 26, 27, 28, 29, 30, 31, 32, 33, 34, 35, 36, 37, 38, 39, or 40.

Example 4

Characterization of Tooth (Enamel)-Binding Peptide Candidates on Enamel Surface A total of 11 selected phage candidates (Example 3) was used in a phage ELISA experiment. Purified phage lysates were used for binding to the enamel blocks using an anti-M13 phage antibody conjugated to horseradish-peroxidase, followed by the addition of chromogenic agent TMB. The plates were read at $A_{450\ nm}$.

For each phage candidate to be tested, the polished and unpolished enamel blocks were incubated for 1 h at room temperature with 200 µL of blocking buffer, consisting of 2% non-fat dry milk (Schleicher & Schuell, Inc.) in TBS. The blocking buffer was removed by aspirating the liquid out of each tube. The tube was rinsed 6 times with wash buffer consisting of TBST-0.05%. The wells were filled with 200 µL of TBST-0.5% containing 1 mg/mL BSA and then 10 μL (over $10^{10}$ pfu) of purified phage stock was added. The samples were incubated at room temperature for 60 min with slow shaking. The non-binding phage was removed by washing 6 times with TBST-0.5%. Then, 100 μL of horseradish peroxidase/anti-M13 antibody conjugate (Amersham USA, Piscataway, N.J.), diluted 1:500 in the blocking buffer, was added and incubated for 1 h at room temperature. The conjugate solution was removed and was washed 6 times with TBST-0.5%. TMB substrate (200 μL) was added to each well and the color was allowed to develop for 5 to 30 min, typically for 10 min, at room temperature. Then, stop solution (200 μL of 2 M $H_2SO_4$) was added to each well and the solution was transferred to a 96-well plate and the $A_{450}$ was measured using a microplate spectrophotometer (Molecular Devices, Sunnyvale, Calif.). The resulting absorbance values are given in Tables 3 and 4. BoEn P means bovine polished enamel and BoEn means bovine enamel.

TABLE 3

Phage ELISA Results on Bovine Polished Enamel-Binding Assay of Selected Phage Candidates

| Phage ID | Amino Acid Sequence | SEQ ID NO. | $O.D._{450}$ |
|---|---|---|---|
| Control | no phage | — | 0.112 |
| BoEn P2 | EPPTRTRVNNHTVTVQAQQH | 22 | 0.641 |
| BoEn P3 | GYCLRGDEPAVCSG | 23 | 0.665 |
| BoEn P5 | NFCETQLDLSVCTV | 25 | 0.797 |
| BoEn P6 | NTCQPTKNATPCSA | 26 | 0.83 |
| BoEn P8 | THNMSHFPPSGHPKRTAT | 28 | 2.02 |

TABLE 4

Phage ELISA Results on Bovine Enamel-Binding Assay of Selected Phage Candidates

| Phage ID | Amino Acid Sequence | SEQ ID NO. | $O.D._{450}$ |
|---|---|---|---|
| Control | no phage | — | 0.193 |
| BoEn 1 | AANPHTEWDRDAFQLAMPPK | 31 | 1.402 |
| BoEn 5 | LNDQRKPGPPTMPTHSPAVG | 35 | 0.944 |
| BoEn 6 | NTCATSPNSYTCSN | 36 | 2.38 |
| BoEn 7 | SDCTAGLVPPLCAT | 37 | 0.892 |
| BoEn 9 | VGTMKQHPTTTQPPRVSATN | 39 | 0.568 |
| BoEn 10 | YSETPNDQKPNPHYKVSGTK | 40 | 3.942 |

Oral surfaces contemplated herein include tooth and, more specifically, enamel or polished enamel. In one embodiment, the peptide composition or the first binding element comprise at least one peptide having the sequence of SEQ ID NO: 22, 23, 25, 26, or 28. In some embodiments, the peptide composition or the first binding element comprise a plurality of peptides, wherein at least one of the peptides has the sequence of SEQ ID NO: 22, 23, 25, 26, or 28. In one embodiment, the peptide composition or the first binding element comprise at least one peptide having the sequence of SEQ ID NO: 31, 35, 36, 37, 39, or 40. In some embodiments, the peptide composition or the first binding element comprise a plurality of peptides, wherein at least one of the peptides has the sequence of SEQ ID NO: 31, 35, 36, 37, 39, or 40.

Example 5

Selection of Tooth (Pellicle)-Binding Peptides Using Standard Biopanning

The purpose of this Example was to identify phage peptides that bind tooth pellicle formed in vivo on bovine enamel using standard phage display biopanning.

Bovine enamel incisors were obtained from SE Dental (Baton Rouge, La.). The teeth were cut to approx. 5 mm squares and polished to remove surface debris. Enamel blocks were sterilized and sewn into intra-oral retainers in order to expose the enamel surface to the human oral environment. A retainer with 2 to 4 enamel blocks was worn in the human mouth for 30 min to form a pellicle layer on the enamel. After incubation, the enamel blocks were removed from the retainer, rinsed with water and embedded in a well plate contained molding material so as to only expose the pellicle coated enamel surface in the well. The plate was sterilized with UV light for 10 minutes.

The substrates were then incubated in blocking buffer for 1 hour at room temperature (~22° C.; 1 mg/mL Bovine Serum Albumin in Phosphate Buffered Saline pH 7.2 (Pierce BUPH™ #28372) with 0.1% TWEEN®20 (PBST), followed by 2 washes with PBST. Libraries of phage containing random peptide inserts ($10^{11}$ pfu) from 15 to 20 amino acids were added to each well. After 30 minutes of incubation at 37° C. and shaking at 50 rpm, unbound phage were removed by aspirating the liquid out of each well followed by 6 washes with 1.0 mL PBST.

The enamel blocks were then transferred to clean tube and 1 mL of elution buffer consisting of 1 mg/mL BSA in 0.2 M glycine-HCl, pH 2.2, was added to each well and incubated for 10 min to elute the bound phages. Then, 167 μL of neutralization buffer consisting of 1 M Tris-HCl, pH 9.1, was added to each well. The phage particles, which were in the elution buffer as well as on the enamel blocks, were amplified by incubating with 20 mL diluted *E. coli* ER2738 cells, from an overnight culture diluted 1:100 in LB medium, at 37° C. for 4.5 h. After this time, the cell culture was centrifuged for 2 min and the upper 15 mL of the supernatant was transferred to a fresh tube, 2.5 mL of PEG/NaCl (20% polyethylene glycol-800, 2.5 M sodium chloride) was added, and the phage was allowed to precipitate overnight at 4° C. The precipitate was collected by centrifugation at 10,000×g at 4° C. and the resulting pellet was resuspended in 1 mL of PBS. This was the first round of amplified stock. The amplified first round phage stock was then titered according to the standard protocol. For subsequent rounds of biopanning, more than $2 \times 10^{11}$ pfu of phage stock from the previous round was used. Each additional round after the first also included additional washes with 0.5% sodium lauryl sulfate in water (Spectrum), two washes with carbonate buffer pH 9.4 (Pierce BUPHTM Carbonate-Bicarbonate Buffer #28382) and 2 washes with 50 mM phosphate buffer, pH 2.5.

The biopanning process was repeated an additional 3 more rounds under the same conditions as described above with an additional exposure of the phage stock to oral soft tissue. The phage stock amplified from the $2^{rd}$ round was exposed first to EPIORAL™ and EPIGINGIVAL™ soft tissues (MatTek Corp, Ashland, Mass.) by incubating 8 μL of the $2^{nd}$ round phage stock+42 μL of blocking buffer (PBST+1 mg/mL BSA) for 60 min. The solution was removed from the tissue and an additional 50 μL of PBS was incubated with the tissue for 30 min. The solutions were combined and used in additional rounds of biopanning as described above.

After the 3rd round of biopanning and each subsequent round, 95 random single phage plaques were isolated and the single stranded phage genomic DNA was prepared using the Illustra Templiphi 500 Amplification Kit (GE Healthcare, Piscataway, N.J.) and sequenced at the DuPont Sequencing Facility using −96 gIII sequencing primer (5'-CCCTCATAGTTAGCGTAACG-3'; SEQ ID NO: 63). The displayed peptide is located immediately after the signal peptide of gene III. Based on the peptide sequences, 31 phage candidates were identified for further pellicle binding analysis.

TABLE 5

Tooth-binding Peptides Identified from Biopanning on 30 min in vivo Pellicle

| Peptide ID | Amino Acid Sequence | SEQ ID NO: |
|---|---|---|
| DenP 01 | NGNNHTDIPNRSSYTGGSFA | 64 |
| DenP 02 | TMTNHVYNSYTEKHSSTHRS | 65 |
| DenP 03 | TTYHYKNIYQESYQQRNPAV | 66 |
| DenP 04 | VEPATKNMREARSSTQMRRI | 67 |
| DenP 05 | YLLPKDQTTAPQVTPIVQHK | 68 |
| DenP 06 | ASNLDSTFTAINTPACCT | 69 |
| DenP 07 | EFPYYNDNPPNPERHTLR | 70 |
| DenP 08 | GMPTRYYHNTPPHLTPKF | 71 |
| DenP 09 | HKNAIQPVNDATTLDTTM | 72 |
| DenP 10 | AVVPADLNDHANHLS | 73 |
| DenP 11 | DLGTFPNRTLKMAAH | 74 |
| DenP 12 | FDGIGLGTATRHQNR | 75 |
| DenP 13 | QAAQVHMMQHSRPTT | 76 |
| DenP 14 | SEARARTFNDHTTPMPII | 77 |
| DenP 15 | ELDHDSRHYMNGLQRKVT | 78 |
| DenP 16 | GPQHVLMQDTHQGYAFDN | 79 |
| DenP 17 | TTGSSSQADTSASMSIVPAH | 80 |
| DenP 18 | KAPIANMLQPHSYQYSVA | 81 |
| DenP 19 | TYQGVPSWPAVIDDAIRR | 82 |
| DenP 20 | VNPNWVETQALHQPPGNT | 83 |
| DenP 21 | DHNNRQHAVEVRENKTHTAR | 84 |
| DenP 22 | IYPNESMSTSNVRGPYHP | 85 |
| DenP 23 | HDPNHLTHQARTIYRNANHT | 86 |
| DenP 24 | SNATMYNIQSHSHHQ | 87 |
| DenP 25 | ANELSTYAQTNPGSG | 88 |
| DenP 26 | DTIHPNKMKSPSSPL | 89 |
| DenP 28 | APPTYQTASYPHNLPSKRKM | 90 |
| DenP 29 | QVPDYLSPTHQKKAFLEIPT | 91 |

TABLE 5-continued

Tooth-binding Peptides Identified from Biopanning on 30 min in vivo Pellicle

| Peptide ID | Amino Acid Sequence | SEQ ID NO: |
|---|---|---|
| DenP 30 | TNDLHANPFTGTYIAPDPTS | 92 |
| DenP 32 | HKNENIMQYNVNDRWHITPA | 93 |
| DenP 33 | IDGPHHSPVHRYHTPSIT | 94 |

Oral surfaces contemplated herein include tooth and, more specifically, pellicle. In one embodiment, the peptide composition or the first binding element comprise at least one peptide having the sequence of SEQ ID NO: 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, or 94. In some embodiments, the peptide composition or the first binding element comprise a plurality of peptides, wherein at least one of the peptides has the sequence of SEQ ID NO: 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, or 94.

Example 6

Characterization of Tooth (Pellicle)-Binding Candidates on Pellicle Surface

A total of 29 selected phage candidates from Table 5 were used in phage ELISA Experiment to determine binding affinity and coverage of each phage on pellicle substrates. Purified phage lysates were used for binding to pellicle coated bovine enamel using an anti-M13 phage antibody conjugated to horseradish-peroxidase, followed by the addition of chromogenic agent TMB. The plates were read at $A_{450\,nm}$.

Enamel substrates were cut to approximately 7 mm squares and mounted on wax mounting for incubation in the mouth for 30 min to form a pellicle coated surface. The pellicle coated enamel substrates were removed from the wax backing and placed in well plates with the pellicle surface exposed as in Example 5. Each pellicle-coated substrate was incubated for 1.5 h at room temperature with 1 mL of blocking buffer, consisting of 1 mg/mL BSA in PBST (Pierce BUPH™ #28372 with 0.1% TWEEN®20). The blocking buffer was removed by aspirating the liquid out of each well. The tube was rinsed 2 times with wash buffer consisting of PBST. The wells were filled with 1 mL of $10^{11}$ pfu purified phage stock which was prepared by diluting in blocking buffer. The samples were incubated for 30 min with slow shaking at 37° C. The non-binding phage was removed by washing 5 times with PBST. Then, 500 μL of horseradish peroxidase/anti-M13 antibody conjugate (Amersham USA, Piscataway, N.J.), diluted 1:500 in the blocking buffer, was added and incubated for 1 h at room temperature (~22° C.). The conjugate solution was removed and was washed 3 times with PBST. Each enamel substrate was removed from the well and washed again in a 15-mL test tube with 5 mL of PBST. Each enamel substrate was then mounted in a clean well plate with only the enamel surface exposed. A 1:1 solution of TMB substrate and $H_2O_2$ (200 μL) was added to each well and the color was allowed to develop for between 5 to 30 min, typically for 10 min, at room temperature (~22° C.). Then, stop solution (100 μL of 2 M $H_2SO_4$) was added to each well and the solution was transferred to a 96-well plate and the $A_{450}$ was measured using a microplate spectrophotometer (Molecular Devices, Sunnyvale, Calif.). The resulting absorbance values, are given in Table 6. The analysis of all 30 pellicle-binding candidates was completed over the course of two days and the results were normalized to an internal control.

TABLE 6

Phage ELISA Results for Pellicle-binding Peptide Candidates Obtained from Biopanning

| Peptide ID | Amino Acid Sequences | SEQ ID NO: | O.D.$_{450}$ (normalized) |
|---|---|---|---|
| Control | IPWWNIRAPLNAGGG | 95 | 1.000 |
| DenP1 | NGNNHTDIPNRSSYTGGSFA | 64 | 1.002 |
| DenP2 | TMTNHVYNSYTEKHSSTHRS | 65 | 1.951 |
| DenP3 | TTYHYKNIYQESYQQRNPAV | 66 | 2.495 |
| DenP4 | VEPATKNMREARSSTQMRRI | 67 | 1.421 |
| DenP5 | YLLPKDQTTAPQVTPIVQHK | 68 | 1.087 |
| DenP7 | EFPYYNDNPPNPERHTLR | 70 | 1.500 |
| DenP8 | GMPTRYYHNTPPHLTPKF | 71 | 1.182 |
| DenP9 | HKNAIQPVNDATTLDTTM | 72 | 1.364 |
| DenP10 | AVVPADLNDHANHLS | 73 | 1.619 |
| DenP11 | DLGTFPNRTLKMAAH | 74 | 1.663 |
| DenP12 | FDGIGLGTATRHQNR | 75 | 2.079 |
| DenP13 | QAAQVHMMQHSRPTT | 76 | 0.845 |
| DenP14 | SEARARTFNDHTTPMPII | 77 | 2.498 |
| DenP15 | ELDHDSRHYMNGLQRKVT | 78 | 1.112 |
| DenP16 | GPQHVLMQDTHQGYAFDN | 79 | 2.190 |
| DenP17 | TTGSSSQADTSASMSIVPAH | 80 | 0.971 |
| DenP18 | KAPIANMLQPHSYQYSVA | 81 | 1.143 |
| DenP19 | TYQGVPSWPAVIDDAIRR | 82 | 1.052 |
| DenP20 | VNPNWVETQALHQPPGNT | 83 | 1.298 |
| DenP21 | DHNNRQHAVEVRENKTHTAR | 84 | 0.728 |
| DenP22 | IYPNESMSTSNVRGPYHP | 85 | 1.420 |
| DenP23 | HDPNHLTHQARTIYRNANHT | 86 | 1.236 |
| DenP24 | SNATMYNIQSHSHHQ | 87 | 0.979 |
| DenP25 | ANELSTYAQTNPGSG | 88 | 0.909 |
| DenP26 | DTIHPNKMKSPSSPL | 89 | 1.039 |
| DenP28 | APPTYQTASYPHNLPSKRKM | 90 | 1.203 |
| DenP29 | QVPDYLSPTHQKKAFLEIPT | 91 | 0.976 |
| DenP30 | TNDLHANPFTGTYIAPDPTS | 92 | 1.082 |
| DenP32 | HKNENIMQYNVNDRWHITPA | 93 | 1.441 |

Oral surfaces contemplated herein include tooth and, more specifically, pellicle. In one embodiment, the peptide composition or the first binding element comprise at least one peptide having the sequence of SEQ ID NO: 64, 65, 66, 67, 68, 70, 71, 72, 73, 74, 75, 76, 77, 78, 79, 80, 81, 82, 83, 84, 85, 86, 87, 88, 89, 90, 91, 92, or 93. In some embodiments, the peptide composition or the first binding element comprise a plurality of peptides, wherein at least one of the peptides has the sequence of SEQ ID NO: 64, 65, 66, 67, 68, 70, 71, 72, 73, 74, 75, 76, 77, 78, 79, 80, 81, 82, 83, 84, 85, 86, 87, 88, 89, 90, 91, 92, or 93.

Example 7

Selection of Pellicle-Binding Peptides Using Standard Biopanning

The purpose of this Example was to identify phage peptides that bind tooth pellicle created with long term exposure in the mouth using standard phage display biopanning.

Bovine enamel incisors were obtained from SE Dental (Baton Rouge, La.). The teeth were cut to approximately 7 mm squares and polished to remove surface debris. Enamel blocks were sterilized and sewn into intra-oral retainers in order to expose the enamel surface to the human oral environment. A retainer with 4 enamel blocks was worn in a human mouth for approximately 8 hours. The retainer was removed from the subject and each enamel block was manually brushed with toothpaste and a soft bristle brush under water. The retainer was reinserted into the subject's mouth for an additional 1 min. The enamel blocks were removed from the retainer, rinsed with water and embedded in a well plate contained molding material so as to only expose the pellicle coated enamel surface in the well. The plate was sterilized with UV light for 10 minutes.

The substrates were then incubated in blocking buffer for 1 hour at room temperature (~22° C.) (1 mg/mL Bovine Serum Albumin in Phosphate Buffered Saline pH 7.2 (Pierce BUPH™ #28372) with 0.1% TWEEN®20 (PBST)), followed by 2 washes with PBST (PBS in 0.1% TWEEN® 20). Libraries of phage containing random peptide inserts ($10^{11}$ pfu) from 16 to 20 amino acids were added to each well. After 30 minutes of incubation at 37° C. and shaking at 50 rpm, unbound phage were removed by aspirating the liquid out of each well followed by 2 washes with 1.0 mL PBST.

The enamel blocks were then transferred to clean tube and 1 mL of elution buffer consisting of 1 mg/mL BSA in 0.2 M glycine-HCl, pH 2.2, was added to each well and incubated for 10 min to elute the bound phages. Then, 167 µL of neutralization buffer consisting of 1 M Tris-HCl, pH 9.1, was added to each well. The phage particles, which were in the elution buffer as well as on the enamel blocks, were amplified by incubating with 20 mL diluted *E. coli* ER2738 cells, from an overnight culture diluted 1:100 in LB medium, at 37° C. for 4.5 h. After this time, the cell culture was centrifuged for 2 min and the upper 15 mL of the supernatant was transferred to a fresh tube, 2.5 mL of PEG/NaCl (20% polyethylene glycol-800, 2.5 M sodium chloride) was added, and the phage was allowed to precipitate overnight at 4° C. The precipitate was collected by centrifugation at 10,000×g at 4° C. and the resulting pellet was resuspended in 1 mL of PBS. This was the first round of amplified stock. The amplified first round phage stock was then titered according to the standard protocol. For the $2^{nd}$, $3^{rd}$, $4^{th}$ and $5^{th}$ rounds of biopanning, more than $2\times10^{11}$ pfu of phage stock from the previous round was used. In these subsequent rounds, additional washes processes were included after the initial incubation of the phage. These washes included a 0.5% sodium lauryl sulfate in water (Spectrum), two washes with carbonate buffer pH 9.4 (Pierce BUPH™ Carbonate-Bicarbonate Buffer #28382) and 2 washes with 50 mM phosphate buffer, pH 2.5 followed by 5 washes with PBST.

After the 3rd round of biopanning and each subsequent round, 95 random single phage plaques were isolated and the single stranded phage genomic DNA was prepared using the Illustra Templiphi 500 Amplification Kit (GE Healthcare, Piscataway, N.J.) and sequenced at the DuPont Sequencing Facility using −96 gIII sequencing primer (5'-CCCTCAT-AGTTAGCGTAACG-3'; SEQ ID NO: 63). The displayed peptide is located immediately after the signal peptide of gene III. Based on the peptide sequences, 23 phage candidates were selected for further pellicle binding analysis. These candidates included 3 sequences previously discovered in panning in Example 5.

TABLE 7

Binding Sequences Identified from Biopanning on Brushed, 8 hr in vivo Pellicle.

| Peptide ID | Amino Acid Sequence | SEQ ID NO |
|---|---|---|
| DenP101 | AIEYQHSATTPWTMRTRLPP | 96 |
| DenP102 | EFYPFAEVPPEKSGIGRQVF | 97 |
| DenP103 | GVHQYSRPTVPSYLWTSGQH | 98 |
| DenP104 | GYQPHYVDHTIGWQPMIRPN | 99 |
| DenP105 | QFNQTSHSFMHGTSGYVPGK | 100 |
| DenP106 | SFSWHRGDWELGHQSKTMGM | 101 |
| DenP107 | SMWHDITKRYRNPSEMVSAY | 102 |
| DenP108 | THGNKHQSWTYPSEINHKNY | 103 |
| DenP109 | WHEPHQFSGENTDYSSSMGT | 104 |
| DenP110 | THGNKHQSWTYPSEINHKNY | 105 |
| DenP111 | DGYKLQTSLDWQMWNP | 106 |
| DenP112 | FPSKWYNHHRHITGHV | 107 |
| DenP113 | GGMGALESYRQWNHLA | 108 |
| DenP114 | GINKGQRPPWESWHEN | 109 |
| DenP115 | GYGQYVSQQTWAHSNK | 110 |
| DenP116 | HDHLSWWGQFDRQNLL | 111 |
| DenP117 | MPGHQESIKVQNWNRV | 112 |
| DenP118 | NLHSPWPSHAAHHWST | 113 |
| DenP119 | NQQMKLVPQHWHRAQP | 114 |
| DenP120 | SEKWFNPGPWPKLATQ | 115 |
| DenP11 | DLGTFPNRTLKMAAH | 74 |
| DenP07 | EFPYYNDNPPNPERHTLR | 70 |
| DenP08 | GMPTRYYHNTPPHLTPKF | 71 |

Oral surfaces contemplated herein include tooth and, more specifically, pellicle, and, even more specifically, brushed pellicle. In one embodiment, the peptide composition or the first binding element comprise at least one peptide having the sequence of SEQ ID NO: 96, 97, 98, 99, 100, 101, 102, 103, 104, 105, 106, 107, 108, 109, 110, 111, 112, 113, 114, 115, 74, 70, or 71. In some embodiments, the peptide composition or the first binding element comprise a plurality of peptides, wherein at least one of the peptides has the sequence of SEQ ID NO: 96, 97, 98, 99, 100, 101, 102, 103, 104, 105, 106, 107, 108, 109, 110, 111, 112, 113, 114, 115, 74, 70, or 71.

Example 8

Characterization of Tooth Pellicle-Binding Candidates on Pellicle Surface

A total of 18 selected phage candidates were used in a phage ELISA Experiment. Purified phage lysates were used for binding to pellicle coated bovine enamel using an anti-M13 phage antibody conjugated to horseradish-peroxidase, followed by the addition of chromogenic agent TMB. The plates were read at $A_{450\ nm}$.

Enamel substrates were cut to approximately 4 mm squares, cleaned, sterilized and mounted on wax mounting for incubation in the mouth for 30 min to form a pellicle coated surface. The pellicle coated enamel substrates were removed from the wax backing and placed in well plates with the pellicle surface exposed as in Example 5. Each pellicle coated substrate was incubated for 1 h at room temperature (~22° C.) with 0.5 mL of blocking buffer, consisting of 1 mg/mL BSA in PBST pH 7.2 (Pierce BUPH™ #28372 with 0.1% TWEEN®20). The blocking buffer was removed by aspirating the liquid out of each well. The wells were rinsed 2 times with wash buffer consisting of PBST. The wells were filled with 1 mL of $10^{11}$ pfu purified phage stock which was prepared by diluting in blocking buffer. The samples were incubated for 30 min with slow shaking at 37° C. The non-binding phage was removed by washing 5 times with PBST. Then, 500 µL of horseradish peroxidase/anti-M13 antibody conjugate (Amersham USA, Piscataway, N.J.), diluted 1:500 in the blocking buffer, was added and incubated for 45 min at room temperature. The conjugate solution was removed and was washed 5 times with PBST. Each enamel substrate was removed from the well and washed again in a 15-mL test tube with 10 mL of PBST. Each enamel substrate was then mounted in a clean well plate with only the enamel surface exposed. A 1:1 solution of TMB substrate and $H_2O_2$ (200 µL) was added to each well and the color was allowed to develop for between 5 to 30 min, typically for 10 min, at room temperature. Then, stop solution (100 µL of 2 M $H_2SO_4$) was added to each well and the solution was transferred to a 96-well plate and the $A_{450}$ was measured using a microplate spectrophotometer (Molecular Devices, Sunnyvale, Calif.). The resulting absorbance values, are given in Table 8. The analysis of all 18 pellicle binding candidates was completed over the course of two days and the results were normalized to the result of DenP3 which was measured on both days.

TABLE 8

Phage ELISA Results for Pellicle-binding Peptide Candidates Obtained from Biopanning on Brushed 8 hr pellicle, Screened with 30 min in vivo Pellicle

| ID | Amino Acid Sequences | SEQ ID NO | O.D._{450} (normalized) |
|---|---|---|---|
| Control | No Phage | — | 0.094 |
| DenP3 | TTYHYKNIYQESYQQRNPAV | 66 | 1.000 |
| DenP101 | AIEYQHSATTPWTMRTRLPP | 96 | 0.467 |
| DenP102 | EFYPFAEVPPEKSGIGRQVF | 97 | 0.520 |
| DenP103 | GVHQYSRPTVPSYLWTSGQH | 98 | 0.879 |
| DenP104 | GYQPHYVDHTIGWQPMIRPN | 99 | 0.790 |
| DenP105 | QFNQTSHSFMHGTSGYVPGK | 100 | 0.470 |

TABLE 8-continued

Phage ELISA Results for Pellicle-binding Peptide Candidates Obtained from Biopanning on Brushed 8 hr pellicle, Screened with 30 min in vivo Pellicle

| ID | Amino Acid Sequences | SEQ ID NO | O.D.$_{450}$ (normalized) |
|---|---|---|---|
| DenP106 | SFSWHRGDWELGHQSKTMGM | 101 | 1.524 |
| DenP107 | SMWHDITKRYRNPSEMVSAY | 102 | 0.726 |
| DenP108 | THGNKHQSWTYPSEINHKNY | 103 | 1.149 |
| DenP109 | WHEPHQFSGENTDYSSSMGT | 104 | 0.716 |
| DenP111 | DGYKLQTSLDWQMWNP | 106 | 1.051 |
| DenP112 | FPSKWYNHHRHITGHV | 107 | 0.413 |
| DenP113 | GGMGALESYRQWNHLA | 108 | 1.348 |
| DenP114 | GINKGQRPPWESWHEN | 109 | 0.703 |
| DenP115 | GYGQYVSQQTWAHSNK | 110 | 0.501 |
| DenP116 | HDHLSWWGQFDRQNLL | 111 | 1.055 |
| DenP117 | MPGHQESIKVQNWNRV | 112 | 0.433 |
| DenP118 | NLHSPWPSHAAHHWST | 113 | 0.641 |
| DenP119 | NQQMKLVPQHWHRAQP | 114 | 1.051 |

Oral surfaces contemplated herein include tooth and, more specifically, pellicle. In one embodiment, the peptide composition or the first binding element comprise at least one peptide having the sequence of SEQ ID NO: 66, 96, 97, 98, 99, 100, 101, 102, 103, 104, 106, 107, 108, 109, 110, 111, 112, 113, or 114. In some embodiments, the peptide composition or the first binding element comprise a plurality of peptides, wherein at least one of the peptides has the sequence of SEQ ID NO: 66, 96, 97, 98, 99, 100, 101, 102, 103, 104, 106, 107, 108, 109, 110, 111, 112, 113, or 114.

Example 9

Peptide-Mediated Adhesion of Co-NTA Polystyrene Beads to Bovine Enamel

Peptide compositions were designed that incorporated oral surface (enamel)-binding peptides discovered by phage display panning on bovine enamel (see Examples 3 and 4) and a sequence of six histidines (hereinafter also referred to as "His6"; SEQ ID NO: 119) which has an affinity to metal chelated nitrilotriacetic acid (NTA). The general design of the enamel binding domain included a short N-terminus sequence followed by two or more oral surface-binding domains separated by a peptide linker. The polyhistidine sequence was located at the C-terminus. Sequences used to assemble peptide-based reagents are listed in Table 9. Peptide samples were produced via fermentation (as described in Example 15). Peptide "Soti13" has the sequence LNSMSD-KHHGHQNTATRNQH (SEQ ID NO: 124) and was identified by biopanning against silica coated TiO$_2$ (see U.S. patent application Ser. No. 12/632,829 to Fahnestock et al.).

TABLE 9

Peptide Compositions

| Peptide ID | Sequence Description | Sequence of Peptide Composition | SEQ ID NO: | Enamel Binding Domains | Second binding element |
|---|---|---|---|---|---|
| DE045 | PGSGGGGSP-BoEn10-GPEEAAKKEEAAK KPA-BoEn10-GPGGHHHHHH | PGSGGGGSPYSETP NDQKPNPHYKVSGT KGPEEAAKKEEAAK KPAYSETPNDQKPN PHYKVSGTKGPGGH HHHHH | 120 | BoEn10-BoEn10 | HHHHHH |
| DE046 | PGSGGGGSP-BoEn10-TonB-BoEn10-GPGGHHHHHH | PGSGGGGSPYSETP NDQKPNPHYKVSGT KGPEPEPEPEPIPEP PKEAPVVIEKPKPKP KPKPKPPAYSETPN DQKPNPHYKVSGTK GPGGHHHHHH | 121 | BoEn10-BoEn10 | HHHHHH |
| DE047 | PGSGGGGSP-BoEn10-GGG-BoEn10-GGG-BoEn10-GPGGHHHHHH | PGSGGGGSPYSETP NDQKPNPHYKVSGT KGGGYSETPNDQKP NPHYKVSGTKGGGY SETPNDQKPNPHYK VSGTKGPGGHHHH HH | 122 | BoEn10-BoEn10-BoEn10 | HHHHHH |
| DE008 | P-HM-T7Tag-S-BoEn10-GPEEAAKKEEAAK KPA-BoEn10-GSGGGGSGSGGG GS-Soti13-GGG-Soti13-GGHHHHHH | PHMASMTGGQQMG SYSETPNDQKPNPH YKVSGTKGPEEAAK KEEAAKKPAYSETP NDQKPNPHYKVSGT KGSGGGGSGSGGG GSLNSMSDKHHGH QNTATRNQHGGGL NSMSDKHHGHQNT ATRNQHGGHHHHHH | 123 | BoEn10-BoEn10 | HHHHHH |

Bovine enamel incisors were obtained from SE Dental (Baton Rouge, La.). Teeth were sectioned and cut into enamel slabs approx. 5 mm on each side using a DREMEL® rotary (Robert Bosch LLC, Farmington Hills, Mich.) saw with a diamond blade. The enamel slabs were cleaned and embedded in a well plate contained molding material so as to only expose the enamel surface in the well.

Polystyrene beads with cobalt-NTA coating (DYNABEADS® TALON®) were obtained from Invitrogen (item#101.02D) as a slurry of 40 mg/mL. The slurry (50 µL; 2 mg beads) was resuspended and washed with 700 µL of binding buffer (50 mM sodium phosphate, pH 8.0, 300 mM NaCl, 0.01% TWEEN® 20) in preparation for His6 binding.

Peptides were dissolved in phosphate buffered saline (Pierce, pH 7.2) at a concentration of 20 µM. Peptide solution (500 µL) was placed in each well containing an enamel slab. Enamel slabs exposed to only PBS in this step were used as a control. Samples were incubated with peptide solution with gentle agitation for 30 min. The peptide solution and PBS were removed from the well plate and each well was rinsed 3 times with repeated additions of PBS. TALON® beads (50 µL) were added to each well and incubated with gentle agitation for 30 min. The TALON® solution was removed and the samples were washed three times with the same binding buffer.

Each enamel sample was removed from the well plate and rinsed again with buffer. Observation following bead binding showed a light brown color on each enamel surface except of the no peptide control and DE045. The enamel slabs were further examined by Electron Microscopy (Hitachi TM-1000 Tabletop SEM Microscope) at 1000×, 2500× and 5000× magnification. Each peptide exposed substrate showed substantial coverage of 1 µm particles across the field of view. The substrate exposed to DE045 also showed bead binding at a lower degree than the other samples. Little to no beads were found on the no peptide control. DE008, which is designed to also bind silica in addition to the polystyrene beads with cobalt-NTA coating, had similar results to those peptides designed with only enamel binding sequences. Table 10 describes particle coverage for each peptide and the no peptide control. The excellent coverage of beads across the enamel surface demonstrate the affinity of the peptide compositions for both the enamel surface and the Co-NTA beads.

TABLE 10

Peptide-mediated Deposition of Co-NTA beads on a Bovine Enamel Surface

| Peptide ID | Particles per um$^2$ at 5000X |
| --- | --- |
| None | <0.01 |
| DE045 (SEQ ID NO: 120) | 0.17 |
| DE046 (SEQ ID NO: 121) | 0.39 |
| DE047 (SEQ ID NO: 122) | 0.44 |
| DE008 (SEQ ID NO: 123) | 0.31 |

Also demonstrated is a peptide composition comprising a first binding element and a second binding element, wherein the second binding element is polyhistidine. Also demonstrated is the association of the second binding element with a particle having a ligand property (cobalt-NTA coated polystyrene beads). In one embodiment, the peptide composition comprises SEQ ID NO: 120, 121, 122 or 123. In another embodiment, the peptide composition comprises SEQ ID NO: 121, 122, or 123.

Example 10

Characterization of Tooth Pellicle-Binding Candidates on Pellicle Surface

The purpose of this example is to confirm the binding of peptide compositions on pellicle surfaces using synthetically produced peptides.

A total of 20 synthetic peptides were manufactured using sequences obtained from Table 6. Peptides were obtained from SynBioSci Corp. (Livermore, Calif.) and included an additional sequence (SSRP; SEQ ID NO: 118) at the N-terminus and biotin labeled lysine at the C-terminus.

Enamel substrates were cut into approximately 7 mm squares and mounted on wax mounting for incubation in the mouth for 30 min to form a pellicle coated surface. The pellicle coated enamel substrates were removed from the wax backing and placed in well plates with the pellicle surface exposed as in Example 5. Each pellicle coated substrate was incubated for 1 h at room temperature (~22° C.) with 1 mL of blocking buffer, consisting of 1 mg/mL BSA in PBST (Pierce BUPH™ #28372 with 0.1% TWEEN® 20). The blocking buffer was removed by aspirating the liquid out of each well. The tube was rinsed 2 times with wash buffer consisting of PBST. The wells were filled with 500 µL of 20 µM peptide solution which was prepared by diluting in blocking buffer. The samples were incubated for 30 min with slow shaking at 37° C. The non-binding peptide was removed by washing 6 times with PBST. Then, 500 µL of horseradish peroxidase/streptavidin conjugate (Pierce #22127), diluted 1:2000 in PBST, was added and incubated for 1 h at room temperature (~22° C.). The conjugate solution was removed and was washed 4 times with PBST.

Each enamel substrate was removed from the well and washed again in a 15-mL test tube with 10 mL of PBST. Each enamel substrate was then mounted in a clean well plate with only the enamel surface exposed. A 1:1 solution of TMB substrate and $H_2O_2$ (200 µL) was added to each well and the color was allowed to develop for between 10 to 20 min, typically for 15 min, at room temperature (~22° C.). Then, 100 µL of solution from each well was transferred to a 96 well reading plate containing stop solution (100 µL of 2 M $H_2SO_4$) in each well. The $A_{450}$ was measured using a microplate spectrophotometer (Molecular Devices, Sunnyvale, Calif.). The resulting absorbance values are given in Table 11. The analysis of 20 pellicle binding candidates was completed over the course of two days and the results were normalized to the best binding candidate from day 1 (DenP03). Each sequence was tested with three replicate enamel coated pellicle substrates.

TABLE 11

Synthetic Peptide ELISA Results for Pellicle-binding Candidates Obtained from Biopanning.

| Peptide ID | Amino Acid Sequence | O.D.$_{450}$ (normalized) | SEQ ID NO |
|---|---|---|---|
| No peptide | — | -0.001 | — |
| DenP1-A | SSRPNGNNHTDIPNRSSYTGGSFAK(biotin) | 0.154 | 125 |
| DenP2-A | SSRPTMTNHVYNSYTEKHSSTHRSK(biotin) | 0.273 | 126 |
| DenP3-A | SSRPTTYHYKNIYQESYQQRNPAVK(biotin) | 1.000 | 127 |
| DenP4-A | SSRPVEPATKNMREARSSTQMRRIK(biotin) | 0.803 | 128 |
| DenP5-A | SSRPYLLPKDQTTAPQVTPIVQHKK(biotin) | 0.462 | 129 |
| DenP7-A | SSRPEFPYYNDNPPNPERHTLRK(biotin) | 0.356 | 130 |
| DenP11-A | SSRPDLGTFPNRTLKMAAHK(biotin) | 0.454 | 131 |
| DenP12-A | SSRPFDGIGLGTATRHQNRK(biotin) | 0.475 | 132 |
| DenP13-A | SSRPQAAQVHMMQHSRPTTK(biotin) | 0.699 | 133 |
| DenP14-A | SSRPSEARARTFNDHTTPMPIIK(biotin) | 0.269 | 134 |
| DenP15-A | SSRPELDHDSRHYMNGLQRKVTK(biotin) | 0.460 | 135 |
| DenP16-A | SSRPGPQHVLMQDTHQGYAFDNK(biotin) | 0.309 | 136 |
| DenP17-A | SSRPTTGSSSQADTSASMSIVPAHK(biotin) | 0.143 | 137 |
| DenP19-A | SSRPTYQGVPSWPAVIDDAIRRK(biotin) | 0.712 | 138 |
| DenP20-A | SSRPVNPNWVETQALHQPPGNTK(biotin) | 0.590 | 139 |
| DenP22-A | SSRPIYPNESMSTSNVRGPYHPK(biotin) | 0.354 | 140 |
| DenP23-A | SSRPHDPNHLTHQARTIYRNANHTK(biotin) | 0.850 | 141 |
| DenP28-A | SSRPAPPTYQTASYPHNLPSKRKMK(biotin) | 0.811 | 142 |
| DenP29-A | SSRPQVPDYLSPTHQKKAFLEIPTK(biotin) | 0.468 | 143 |
| DenP32-A | SSRPHKNENIMQYNVNDRWHITPAK(biotin) | 1.135 | 144 |

Provided are peptide compositions comprising a pellicle binding peptide and biotin. In one embodiment, the first binding element of a peptide composition comprises a pellicle binding peptide or a peptide comprising the sequence of SEQ ID NO: 125, 126, 127, 128, 129, 130, 131, 132, 133, 134, 135, 136, 137, 138, 139, 140, 141, 142, 143, or 144. In one embodiment, the second binding element comprises biotin.

Example 11

Determination of the Peptide Binding Affinity on Pellicle Surface

The purpose of this Example was to determine the affinity and specificity of the pellicle-binding peptides and peptide compositions comprising the pellicle-binding peptides identified in Example 10, measured as MB$_{50}$ values, using an ELISA assay.

Pellicle-binding peptides, DenP3 and DenP32 as described in Table 11, were synthesized using standard solid phage synthesis method and were biotinylated at the C-terminus lysine residue of binding sequence for detection purposes.

Enamel substrates were cut into approximately 4 mm squares and mounted on wax mounting for incubation in the mouth for 30 min to form a pellicle coated surface. The pellicle coated enamel substrates were removed from the wax backing and placed in well plates with the pellicle surface exposed as in Example 5. Each pellicle coated substrate was incubated for 1 h at room temperature with 1 mL of blocking buffer, consisting of 1 mg/mL BSA in PBST (Pierce BUPH™ #28372 with 0.1% TWEEN® 20). The blocking buffer was removed by aspirating the liquid out of each well. The tube was rinsed twice with wash buffer consisting of PBST. The wells were filled with 500 µL of peptide solution which was prepared by diluting in blocking buffer across a range of concentrations. The samples were incubated for 30 min with slow shaking at 37° C. The non-binding peptide was removed by washing 6 times with PBST. Then, 500 µL of alkaline phosphatase/streptavidin conjugate (Pierce), diluted 1:2500 in PBST, was added and incubated for 1 h at room temperature. The conjugate solution was removed and was washed 4 times with PBST.

Each enamel substrate was removed from the well and washed again in a 15-mL test tube with 10 mL of PBST. Each enamel substrate was then mounted in a clean well plate with only the enamel surface exposed. Methyl umbelliferone 4-phosphate (4-MUP) (150 µL) substrate (Sigma) was added to each well and incubated for 30 min protected from ambient light. Then, 100 μL of solution from each well was transferred to a 96 well reading plate. Fluorescence was read using a microplate spectrophotometer (Molecular Devices, Sunnyvale, Calif.). The results were plotted as relative fluorescence units versus the concentration of peptide using GraphPad Prism 4.0 (GraphPad Software, Inc., San Diego, Calif.). The $MB_{50}$ values were calculated from Scatchard plots and are shown Table 12.

TABLE 12

Summary of $MB_{50}$ Values for Pellicle-Binding Peptides Against Pellicle Surface.

| Peptide ID | SEQ ID NO: | Amino Acid Sequence | $MB_{50}$ (M) |
|---|---|---|---|
| DenP3-A | 127 | SSRPTTYHYKNIYQESYQQRNPAVK(biotin) | $2.8 \times 10^{-5}$ |
| DenP32-A | 144 | SSRPHKNENIMQYNVNDRWHITPAK(biotin) | $2.5 \times 10^{-5}$ |

In one embodiment, the peptide composition comprises SEQ ID NO: 127 or 144. In another embodiment, the peptide composition comprises a pellicle-binding peptide and biotin. In one embodiment, the peptide composition binds to a pellicle surface with an $MB_{50}$ of about $10^{-5}$M.

Example 12

Prophetic

Determination of the Peptide Binding Affinity on Benefit Agent Surface

The purpose of this example is to confirm the binding preference of binding elements on pellicle surfaces versus the surface of the benefit agent containing a ligand property. A biotinylated peptide with a known affinity for pellicle surface is tested against beads designed to bind to a polyhistidine moiety (e.g., 6 histidine residues).

Polystyrene beads with a cobalt-NTA coating (DYNABEADS® TALON®) are obtained from Invitrogen (item#101.02D) as a slurry of 40 mg/mL. Approximately 50 μL of the slurry (2 mg beads) are resuspended and washed with 700 μL of PBST. The beads are incubated for 1 hour at room temperature (~22° C.) in blocking buffer (1 mg/mL BSA in PBST). A magnet is used to retain the beads in the bottom of the test tube while the blocking buffer is removed. The beads are washed two times with PBST and resuspended in solution by agitation after removing the magnet. Peptide solution (500 μL) is prepared by diluting in blocking buffer across a range of concentrations. The samples are incubated for 30 min with slow shaking at 37° C. The non-binding peptide is removed by washing 6 times with PBST. Then, 500 μL of alkaline phosphatase/streptavidin conjugate (Pierce), diluted 1:2500 in PBST, is added and incubated for 1 h at room temperature. The conjugate solution is removed and the beads are washed 4 times with PBST. The beads are transferred to a clean test tube. Methyl umbelliferone 4-phosphate (4-MUP) substrate (Sigma) is added to each test tube and incubates for 30 min protected from ambient light. The beads are again held at the bottom of the tube with a magnet and 100 uL of solution from each test tube is transferred to a 96 well reading plate. Fluorescence is read using a microplate spectrophotometer (Molecular Devices, Sunnyvale, Calif.). The results are plotted as relative fluorescence units versus the concentration of peptide using GraphPad Prism 4.0 (GraphPad Software, Inc., San Diego, Calif.). The $MB_{50}$ values are calculated from Scatchard plots. In some embodiments, the $MB_{50}$ values show that the affinity for the Co—NTA coated beads is at least about an order of magnitude higher than that measured against the pellicle surface, thus, the binding element has a greater affinity for the pellicle surface than for the particles.

Example 13

Peptide-Mediated Adhesion of Streptavidin-Coated Gold Particles to Bovine Enamel Peptides were designed that incorporated binding domains discovered by phage display panning on tooth surfaces (see Example 3) and a second binding element biotin conjugated to the C-terminus which has a known affinity to streptavidin and avidin proteins. Peptide samples were produced via standard synthetic solid phage methods. As a control, a non-biotinylated peptide that included the same binding domain for the tooth surface was also tested.

TABLE 13

Peptides Designed for Peptide-mediated Adhesion of Streptavidin-coated Particles.

| Peptide ID | Description | Sequence | SEQ ID NO: | Enamel Binding Domain(s) | Second Binding Element |
|---|---|---|---|---|---|
| DenP03-C | DenP03-K(biotin) | TTYHYKNIYQ ESYQQRNPA VK(biotin) | 161 | DenP03 | biotin |
| DenP03-D (control) | DenP03-H6 | TTYHYKNIYQ ESYQQRNPA VHHHHHH | 162 | DenP03 | HHHHHH (SEQ ID NO: 119) |

Bovine enamel incisors were obtained from SE Dental (Baton Rouge, La.). Teeth are sectioned and cut into enamel slabs approx. 5 mm on each side using a DREMEL® saw with a diamond blade. The enamel blocks are cleaned and place each in a plastic microcentrifuge tube.

Each enamel block was incubated for 45 min in phosphate buffered saline with 0.1% TWEEN® 20 (PBST) and 1 mg/mL bovine serum albumin (BSA) at room temperature (22° C.). All blocks were rinsed with PBST twice while vortexing in the microcentrifuge tube. The peptides were first diluted to 10 mM in water and then a working concentration of 20 µM was prepared in PBST with 1 mg/mL BSA. Each sample was exposed to the peptide solution or a no peptide buffer control for 30 min at room temperature. The samples were slowly rotated during incubation. The enamel blocks were removed from the peptide solution and washed four times with PBST with vortexing.

50 nm gold nanoparticles functionalized with streptavidin were obtained from Nanocs Inc (New York, N.Y.) and diluted to 0.006% wt in PBST with 1 mg/mL BSA. All enamel samples were then exposed to the gold nanoparticle solution for 1 hr at room temperature with slow rotation. The samples were rinsed 3 times with water and allowed to dry prior to analysis.

Each enamel sample was examined with Electron Microscopy. To reduce electronic charging, each sample was coated with carbon prior to analysis. Images were collected on a Hitachi S4700 FESEM at 1000×, 10000× and 30000× magnification. Particles were counted per micrograph and the density of particle coverage was compared (Table 14).

TABLE 14

Peptide-mediated Adhesion of Streptavidin-coated Particles on Enamel

| Peptide ID | Second Binding Element | Particles per µm² at 10000X |
|---|---|---|
| None | None | 0.37 |
| DenP03-C (SEQ ID NO: 161) | Biotin | 1.75 |
| DenP03-D (SEQ ID NO: 162) (control) | HHHHHH (SEQ ID NO: 119) | 0.23 |

The higher coverage of streptavidin particles on the enamel surface first coated with the biotin containing sequence demonstrate the affinity of the designed peptides for both the enamel surface and the streptavidin coated particles.

In some embodiments, the peptide composition comprises an amino acid sequence selected from the group consisting of SEQ ID NOs: 161 and 162.

Example 14

Tooth Whitening with Sequentially-Applied Peptide and Pigments

A peptide composition was designed to include pellicle-binding domains discovered in biopanning and a second binding element designed to bind to negatively charged pigment, such as silica-coated titanium dioxide. The pellicle-binding domain includes two pellicle-binding elements DenP03 (SEQ ID NO: 66) and a linker, "Lb2", SEQ ID NO. 54. A flexible, non-charged linker (GSSGPGSS, SEQ ID NO: 160) connects the two binding elements. As a control a second peptide was designed that incorporated the same pellicle-binding domains, but did not include the additional domain to bind to a negatively charged pigment. Peptides were produced by fermentation such as is described in Example 16.

TABLE 15

Pellicle-binding conjugates with and without electrostatic binding element

| Peptide ID | Sequence | SEQ ID NO: | First Binding Element | SEQ ID NO | Second Binding Element | SEQ ID NO | Second Binding Element Charge at pH 7.2 |
|---|---|---|---|---|---|---|---|
| DE118 | PSSSRPTTYHYK NIYQESYQQRN PAVGPEEAAKK EEAAKKPASSRP TTYHYKNIYQES YQQRNPAVGPH HHHHH | 163 | P-SSSRP-DenP03-Lb2-SSRP-DenP03 | 164 | GPHHHH HH | 165 | 1.0 |
| DE101 | PSSRPTTYHYKN IYQESYQQRNPA VGPEEAAKKEE AAKKPASSRPTT YHYKNIYQESYQ QRNPAVGSSGP GSSKQPNKQPN KQPNKQPNKQP NKQPNKQPNKQ PNKQPNGPHHH HHH | 166 | P-SSRP-DenP03-Lb2-SSRP-DenP03 | 167 | (KQPN)9-GPHHHH HH | 168 | 10.0 |

Silica-coated rutile titanium dioxide (Luce II WW) was obtained from US Cosmetics Corp. (Dayville, Conn.). A 12 wt % solution of the pigment was prepared with Millipore water. The solution was dispersed by horn sonication using a Branson Sonifier 150 at 10 W. The solution was sonicated in an ice bath for 6 min total, with 2 min sonication intervals. A working solution of 1 wt % in 10 mM sodium phosphate buffer at pH7.2 was made for application to peptide coated enamel. A 0.01% solution of this dispersion diluted in the same buffer was measured on a Malvern Zetasizer Nano dynamic light scattering instrument. The dispersion had an average particle diameter (Z-avg) of 445 nm and a zeta potential of −57 mV.

Bovine enamel incisors were obtained from SE Dental (Baton Rouge, La.). Teeth were sectioned and cut into enamel slabs approx. 7 mm on each side using a DREMEL® saw with a diamond blade. The enamel slabs were cleaned and lightly polished to remove surface debris. The enamel was pretreated with a mixture of coffee and tea in order to stain to a color similar to human stained teeth. Each enamel block was then mounted on wax mounting and sterilized with ethylene oxide. Mounted enamel bocks were incubated in the mouth for 30 min to form a pellicle-coated surface. The mounted enamel blocks were brushed with a toothbrush and a 1:2 dilution of COLGATE® MAXFRESH® toothpaste (Colgate-Palmolive Co., New York, N.Y.) and then reinserted into the mouth for 1 minute. The pellicle-coated enamel substrates were removed from the wax backing, rinsed with water and placed in well plates. Each pellicle coated enamel slab was measured for color using a Konica-Minolta 2600d integrating sphere spectrophotometer.

Peptides listed in Table 15 were dissolved into pH 7.2 PBS buffer at a concentration of 20 µM. Three replicate teeth were used for each experimental condition. Each tooth was incubated with peptide solution for 30 min or buffer alone as a control. The enamel blocks were removed from the peptide solution and rinsed with PBS buffer. The enamel blocks were then incubated in the 1% solution of silica-coated $TiO_2$ for 30 min. The enamel blocks were removed, rinsed with 10 mM phosphate buffer and blotted dry. Each substrate was measured for color (L, a*, b*, C*, h) values. The total color difference, Delta $E^*_{ab}$ and the Metric Hue Difference, Delta $H^*_{ab}$, for the whitening process were calculated using equations (1) and (2) below:

$$\text{Delta } E^*_{ab} = ((L^*_1 - L^*_2)^2 + (a^*_1 - a^*_2)^2 + (b^*_1 - b^*_2)^2)^{1/2} \quad (1)$$

$$\text{Delta } H^*_{ab} = (2(C^*_1 C^*_2 - a^*_1 a^*_2 - b^*_1 b^*_2))^{1/2} \quad (2)$$

where L*=the lightness variable, a* and b* are the chromaticity coordinates and C* is the chroma of CIELAB colorspace as defined by the International Commission of Illumination (CIE) and described in ASTM D2244-09b and subscript 1 denotes the initial color value and subscript 2 denotes the final color value. The color measurements are provided in Table 16.

TABLE 16

Whitening Performance of Peptide-mediated Deposition of a Negatively Charged $TiO_2$ on Pellicle

| | Delta $E^*_{ab}$ | | Delta $H^*_{ab}$ | |
|---|---|---|---|---|
| Peptide | Avg | Stdev | Avg | Stdev |
| None | 7.40 | 3.26 | 1.09 | 0.45 |
| DE118 | 6.78 | 0.34 | 1.60 | 0.35 |
| DE101 | 10.70 | 1.43 | 2.93 | 0.60 |

The color measurements in Table 16 demonstrate that a peptide sequence containing both a pellicle-binding element and a second binding element designed for electrostatic interaction with the negatively charged silica-coated titanium dioxide resulted in improved particle deposition as indicated by a larger color difference measurement when compared to a no peptide control and a peptide not containing the second binding element.

In some embodiments, the peptide composition comprises a first binding element having an amino acid sequence selected from the group consisting of SEQ ID NOs: 164 and 167.

In some embodiments, the peptide composition comprises a second binding element having an amino acid sequence selected from the group consisting of SEQ ID NOs: 165 and 168.

In some embodiments, the peptide composition comprises an amino acid sequence selected from the group consisting of SEQ ID NOs: 163 and 166.

Example 15

Prophetic

Tooth Whitening with Sequentially Applied Peptide and Pigments

Peptide compositions are designed to include pellicle-binding domains discovered in biopanning and an additional domain designed to bind to negatively charged pigment such as silica-coated titanium dioxide (Table 17). A flexible, non-charged linker (GSSGPGSP, SEQ ID NO: 158) connects the two binding elements. Peptides are produced by fermentation such as is described in Example 16.

TABLE 17

Pellicle-binding Conjugates Designed for Electrostatic Binding to Negatively Charged Pigments

| Peptide ID | Amino Acid Sequence | SEQ ID NO: | Description: Pellicle binding domain(s) and linkers | Binding Element | Binding Element SEQ ID NO: |
|---|---|---|---|---|---|
| Estat1 | PHSSRPTTYHYKNIYQESYQQRNP AVGPEPEPEPEPIPEPPKEAPVVIE KPKPKPKPKPKPPASSRPTTYHYK NIYQESYQQRNPAVGSSGPGSPK QPNKQPNKQPNKQPNKQPN | 145 | DenP03-TonB-DenP03 | $(KQPN)_5$ | 152 |

TABLE 17-continued

Pellicle-binding Conjugates Designed for Electrostatic Binding to Negatively Charged Pigments

| Peptide ID | Amino Acid Sequence | SEQ ID NO: | Description: Pellicle binding domain(s) and linkers | Binding Element | Binding Element SEQ ID NO: |
|---|---|---|---|---|---|
| Estat2 | PHSSRPTTYHYKNIYQESYQQRNP AVGPEPEPEPEPIPEPPKEAPVVIE KPKPKPKPKPKPPASSRPTTYHYK NIYQESYQQRNPAVGSSGPGSPK QPNKQPNKQPNKQPNKQPNKQP NKQPNKQPNKQPN | 146 | DenP03-TonB-DenP03 | (KQPN)$_9$ | 153 |
| Estat3 | PHSSRPTTYHYKNIYQESYQQRNP AVGPEPEPEPEPIPEPPKEAPVVIE KPKPKPKPKPKPPASSRPTTYHYK NIYQESYQQRNPAVGSSGPGSPK QPNKQPNKQPNKQPNKQPNKQP NKQPNKQPNPKQPNKQPNKQPN KQPNKQPN | 147 | DenP03-TonB-DenP03 | (KQPN)$_{13}$ | 154 |
| Estat4 | PHSSRPTTYHYKNIYQESYQQRNP AVGPEPEPEPEPIPEPPKEAPVVIE KPKPKPKPKPKPPASSRPTTYHYK NIYQESYQQRNPAVGSSGPGSPG KGKGKGKGK | 148 | DenP03-TonB-DenP03 | (GK)$_5$ | 155 |
| Estat5 | PHSSRPTTYHYKNIYQESYQQRNP AVGPEPEPEPEPIPEPPKEAPVVIE KPKPKPKPKPKPPASSRPTTYHYK NIYQESYQQRNPAVGSSGPGSPG KGKGKGKGKGKGKGK | 149 | DenP03-TonB-DenP03 | (GK)$_9$ | 156 |
| Estat6 | PHSSRPTTYHYKNIYQESYQQRNP AVGPEPEPEPEPIPEPPKEAPVVIE KPKPKPKPKPKPPASSRPTTYHYK NIYQESYQQRNPAVGSSGPGSPG KGKGKGKGKGKGKGKGKGKG KGK | 150 | DenP03-TonB-DenP03 | (GK)$_{13}$ | 157 |
| DE082 | PHSSRPTTYHYKNIYQESYQQRNP AVGPEPEPEPEPIPEPPKEAPVVIE KPKPKPKPKPKPPASSRPTTYHYK NIYQESYQQRNPAVGSSGPGSPH HHHHH | 151 | DenP03-TonB-DenP03 | HHHHHH | 119 |

Silica-coated titanium dioxide is prepared with rutile titanium dioxide (DuPont, Wilmington, Del.) that is first coated with silica by a process described in U.S. Pat. No. 2,885,366 to Iler with a 3% silica loading. A stable dispersion is made with approximately 10 g of the silica-coated titanium dioxide combined with 25 g 0.5 mm zirconia-silica beads and 40 g water in a SPEEDMIXER™ DAC150 FVZ-K (FlackTek Inc., Landrum, S.C.). The mixture is processed for a total of 20 minutes. Following mixing, the solution is filtered to remove the zirconia-silica beads. The resulting pigment dispersion is an opaque white solution and stable dispersion with a negative zeta potential. A 0.5% (solids weight) solution of silica-coated titanium dioxide is prepared in 10 mM phosphate buffer, pH 7.2.

Enamel substrates are cut into approximately 7 mm squares from bovine incisors obtained from SE Dental (Baton Rouge, La.). Each enamel block is first treated with a combination of tea and coffee for 2 days to stain the blocks to a color similar to natural human tooth shades. The substrates are polished, sterilized and mounted on wax mounting for incubation in the mouth for 30 min to form a pellicle-coated surface. The pellicle-coated enamel substrates are removed from the wax backing and color is measured (L, a*, b*) on each substrate using an integrating sphere spectrophotometer (Minolta CM2600d).

Peptides are dissolved into pH 7.2 PBS buffer at concentration 10 µM. Each tooth is incubated with peptide solution for 30 min or buffer alone as a control. The enamel blocks are removed from the peptide solution and rinsed with PBS buffer. The enamel blocks are then incubated in the 0.5% solution of silica-coated TiO$_2$ for 30 min. The enamel blocks are removed, rinsed with 10 mM phosphate buffer and blotted dry. Each substrate was measured for color (L, a*, b*, C*, h) values and color change calculated as described in Example 14. In preferred embodiments, peptide-mediated color deposition is noted by a calculated delta E significantly greater than the no peptide control.

In some embodiments, the peptide composition comprises a second binding element having an amino acid sequence selected from the group consisting of SEQ ID NOs: 152, 153, 154, 155, 156, and 157.

In some embodiments, the peptide composition comprises an amino acid sequence selected from the group consisting of SEQ ID NO: 145, 146, 147, 148, 149, 150, and 151.

Example 16

Biological Production of Peptides by Fermentation
Construction of Production Strains DNA sequences were designed to encode a given peptide sequence using favorable codons for *E. coli* and to avoid sequence repeats and mRNA secondary structure. The gene sequence was designed by DNA 2.0, Inc. (Menlo Park, Calif.) using proprietary software which is described by Gustafsson et al. (*Trends in Biotechnol.*, (2004) 22(7):346-355). The DNA sequence encoding the amino acid sequence was followed by two termination codons and a recognition site for endonuclease AscI.

The genes were assembled from synthetic oligonucleotides and cloned into a standard plasmid cloning vector by DNA 2.0, Inc. The sequences were then verified by DNA sequencing by DNA 2.0, Inc. The synthetic gene was excised from the cloning vector with the endonuclease restriction enzymes BamHI and AscI and ligated into an expression vector using standard recombinant DNA methods. The vector pKSI(C4)E-HC77643 (SEQ ID NO: 159) (U.S. Patent Application Publication No. 2009-0029420-A1; hereby incorporated by reference) was used to express the gene encoding the peptide. Vector pKSI(C4)E-HC77643 is a derivative of expression vector pKSIC4-HC77623. Specifically, the 5 acid labile aspartic acid residues in the KSI(C4) inclusion body tag were replaced with glutamic acid in order to make the tag more acid resistant.

Plasmid pKSIC4-HC77623 was derived from the commercially available vector pDEST17 (Invitrogen, Carlsbad, Calif.). Construction of this vector has been previously described in U.S. Pat. No. 7,285,264 to O'Brien et al., hereby incorporated by reference. It includes sequences derived from the commercially available vector pET31b (Novagen, Madison, Wis.) that encode a fragment of the enzyme ketosteroid isomerase (KSI). The KSI fragment was included as a fusion partner to promote partition of the peptides into insoluble inclusion bodies in *E. coli*. The KSI-encoding sequence from pET31b was modified using standard mutagenesis procedures (QuickChange II, Stratagene, La Jolla, Calif.) to include three additional Cys codons, in addition to the one Cys codon found in the wild type KSI sequence.

The DNA sequence encoding the desired peptide was inserted into pKSI(C4)E-HC77643 by substituting for sequences in the vector between the BamHI and AscI sites. Plasmid DNA containing the peptide encoding sequence and vector DNA was digested with endonuclease restriction enzymes BamHI and AscI, then the peptide-encoding sequence and vector DNA were mixed and ligated by phage T4 DNA ligase using standard DNA cloning procedures. The correct construct, in which the sequence encoding the peptide was inserted into pKSI(C4)E-HC77643, was identified by restriction analysis and was verified by DNA sequencing. In this construct, the sequence encoding the peptide conjugate was substituted for those encoding HC77643. The sequence was operably linked to the bacteriophage T7 gene 10 promoter and was expressed as a fusion protein, fused with the variant KSI partner.

To test the expression of the peptide, the expression plasmid was transformed into the BL21-AI *E. coli* strain (Invitrogen, catalog no. C6070-03). To produce the recombinant fusion peptide, 50 mL of LB-ampicillin broth (10 g/L bacto-tryptone, 5 g/L bacto-yeast extract, 10 g/L NaCl, 100 mg/L ampicillin, pH 7.0) was inoculated with the transformed bacteria and the culture was shaken at 37° C. until the $OD_{600}$ reached 0.6. The expression was induced by adding 0.5 mL of 20 wt % L-arabinose to the culture and shaking was continued for another 4 h.

Growth Conditions

The *E. coli* BL21-AI cells containing the expression plasmid encoding the peptide were grown for 20 hours at 37° C. with agitation (200 rpm) in 2.8-L Fernbach flasks containing 1-L of modified ZYP-5052 auto-induction media (Studier, F. W, (2005) *Protein Expression and Purification* 41:207-234). The media composition per liter was as follows: 10 g/L Tryptone, 5 g/L Yeast Extract, 5 g/L NaCl, 50 mM $Na_2HPO_4$, 50 mM $KH_2PO_4$, 25 mM $(NH_4)_2SO_4$, 3 mM $MgSO_4$, 0.75% glycerol, 0.075% glucose and 0.05% L-arabinose (inducer for *E. coli* BL21 AI T7 system). Under these conditions about 20 g/L wet weight of cells was obtained per liter.

Inclusion Body Isolation

The following process was performed in one 500-mL bottle. Cells were separated from the growth media by centrifugation and washed with 200-mL (10 g cell paste/100-mL buffer) 20 mM Tris buffer and 10 mM EDTA at pH 8.0. The cell paste was resuspended in 200 mL of 20 mM Tris buffer and 10 mM EDTA at pH 8.0 with added lysozyme (5 mg/200 mL) and taken through at lease one freeze-thaw cycles to facilitate lysis. Lysis was completed by sonication and the inclusion body paste is recovered by centrifugation (9000 RCF for 20 minutes at 4° C.). Each additional wash step included resuspension of the inclusion body paste, followed by sonication and centrifugation (9000 RCF for 20 minutes at 4° C.). Wash steps included a high pH wash (50 mM Tris HCL pH 9.0) followed by additional washes with 20 mM Tris-HCl pH 8.0. Typically 5 g/L inclusion body paste was recovered.

Acid Cleavage

The recovered inclusion body paste was resuspended in 100-mL of pure water and the pH of the mixture adjusted to 2.2 using HCl. The acidified suspension was heated to 70° C. for 14 hours with agitation to complete cleavage of the aspartyl-prolyl (DP) site separating the fusion peptide from the product peptide.

Oxidative Cross-Linking to Separate the IBT from the Peptide of Interest

The product was cooled to ~5° C. then the pH neutralized to 5.3 using NaOH and cooled for an additional 1 hour at ~5° C. to facilitate precipitation of cysteine cross-linked KSI (C4)E tag. The mixture was then centrifuged at 10000 RCF for 30 minutes at 4° C. The pellet contained the inclusion body fusion partner KSI (C4)E.

Results After Oxidative Cross-Linking:

SDS-PAGE gel analysis of both the precipitate paste and the remaining soluble fraction showed the presence of KSI (C4)E in the insoluble paste with the desired peptide remaining in the soluble fraction.

The supernatant containing the peptide was analyzed by HPLC to confirm the presence of peptide. Further analysis of isolated peptide by LCMS confirmed the absence of contaminating KSI fragments seen with the KSI (C4) version which contains 5 potential internal acid cleavable "D" sequence and 1 preferred acid cleavage site (Asp-Pro).

What is claimed is:

1. An oral care system comprising:
   (a) a polypeptide comprising:
      (i) a first binding element having affinity for an oral surface with a $MB_{50}$ value of $10^{-5}$ molar or less comprising the amino acid sequence of SEQ ID NO: 66; and
      (ii) a second binding element; and
   (b) a composition comprising particles, said particles comprising a benefit agent, wherein said particles have an average particle size in the range of 0.01 micron to 10 microns; and the second binding element associates non-covalently with the particles.

2. The oral care system of claim 1 wherein said composition comprising particles is a stable dispersion of said particles.

3. The oral care system of claim 1, wherein the polypeptide comprises a plurality first binding elements.

4. The oral care system of claim 1 wherein the oral surface is a tooth surface.

5. The oral care system of claim 4 wherein the tooth surface is enamel.

6. The oral care system of claim 4 wherein the tooth surface is pellicle.

7. The oral care system of claim 1 wherein the first binding element has a greater binding affinity for the oral surface relative to an affinity for the particles.

8. The oral care system of claim 1 wherein the association between the second binding element and the particles is electrostatic-based.

9. The oral care system of claim 1 wherein the benefit agent comprises a colorant.

10. The oral care system of claim 9, wherein the colorant is a pigment.

11. The oral care system of claim 10, wherein the pigment comprises $TiO_2$.

12. The oral care system of claim 2, wherein the stable dispersion is charge stabilized.

13. The oral care system of claim 2 wherein the stable dispersion comprises a zeta potential having an absolute value of at least 25 mV.

14. The oral care system of claim 2 wherein the stable dispersion comprises a dispersant.

15. The oral care system of claim 14 wherein the dispersant is an ionic dispersant or a non-ionic dispersant.

16. The oral care system of claim 1 wherein the polypeptide comprises an amino acid sequence selected from the group consisting of SEQ ID NOs: 145, 146, 147, 148, 149, 150 and 151.

17. The oral care system of claim 1 wherein the polypeptide comprises amino acid sequence SEQ ID NO: 166.

18. The oral care system of claim 1 wherein the polypeptide comprises a second binding element comprising an amino acid sequence selected from the group consisting of SEQ ID NOs: 152, 153, 154, 155, 156, 157 and 168.

19. A method for applying an oral care benefit agent to an oral surface comprising:
(a) providing the oral care system of claim 1; and
(b) contacting an oral surface with the oral care system of (a) whereby the benefit agent is applied to said oral surface.

20. The method of claim 19 wherein the peptide composition of the oral care system is contacted with the oral surface prior to contacting the composition comprising particles.

21. The method of claim 19 wherein the peptide composition of the oral care system and the composition comprising particles are applied to the oral surface concomitantly.

* * * * *